US010335569B2

(12) United States Patent
Beard et al.

(10) Patent No.: US 10,335,569 B2
(45) Date of Patent: Jul. 2, 2019

(54) OXYGEN FACE MASK AND COMPONENT SYSTEM

(71) Applicant: Monitor Mask Inc., Seattle, WA (US)

(72) Inventors: John W. Beard, Seattle, WA (US); Stanton D. Batchelor, Cary, NC (US); Thomas R. Blackburn, III, Fuquay-Varina, NC (US); Edward P. Browka, Oneida, NY (US); David S. Reid, V, Winston-Salem, NC (US)

(73) Assignee: Monitor Mask Inc., Seattle, WA (US)

( * ) Notice: Subject to any disclaimer, the term of this patent is extended or adjusted under 35 U.S.C. 154(b) by 917 days.

(21) Appl. No.: 14/823,272

(22) Filed: Aug. 11, 2015

(65) Prior Publication Data

US 2016/0038709 A1 Feb. 11, 2016

Related U.S. Application Data

(63) Continuation of application No. PCT/US2014/015405, filed on Feb. 7, 2014.
(Continued)

(51) Int. Cl.
*A61M 16/08* (2006.01)
*A61M 16/06* (2006.01)
(Continued)

(52) U.S. Cl.
CPC ......... *A61M 16/0816* (2013.01); *A61B 5/097* (2013.01); *A61M 16/06* (2013.01);
(Continued)

(58) Field of Classification Search
CPC .............. A61M 16/06; A61M 16/0611; A61M 16/0622; A61M 16/0627; A61M 16/0633; A61M 16/08; A61M 16/0816; A61M 16/0833; A61M 16/0841; A61M 16/085; A61M 16/208; A61M 2202/0208;
(Continued)

(56) References Cited

U.S. PATENT DOCUMENTS 3,572,660 A 3/1971 Mahon et al.
4,201,205 A 5/1980 Bartholomew
(Continued)

FOREIGN PATENT DOCUMENTS

WO 91/14469 A1 10/1991
WO 98/29153 A1 7/1998
(Continued)

*Primary Examiner* — Jan Christopher L Merene
*Assistant Examiner* — Joseph D. Boecker
(74) *Attorney, Agent, or Firm* — Seed IP Law Group LLP

(57) ABSTRACT

An oxygen face mask and component system is provided, the mask is designed to cover a user's nose and at least partially cover a user's mouth, the mask having lateral ports. Systems and assemblies including such a face mask and additional components are further provided, including a colorimetric $CO_2$ detector, a sealing cap with or without a resilient sealing flap, a capnography gas analysis unit, a non-rebreather valve, a pulmonary function module, nebulizer, a gas scavenging system, a gas reservoir system, a gas filter, sample lines that are either straight or at an angle, and an aerosol mask platform; and methods of making and using such a face mask are also provided.

13 Claims, 44 Drawing Sheets

Related U.S. Application Data

(60) Provisional application No. 61/763,404, filed on Feb. 11, 2013, provisional application No. 61/880,849, filed on Sep. 21, 2013, provisional application No. 61/917,685, filed on Dec. 18, 2013.

(51) Int. Cl.
| | | |
|---|---|---|
| *A61M 16/10* | (2006.01) | |
| *A61B 5/097* | (2006.01) | |
| *A61B 5/083* | (2006.01) | |
| *A61M 16/20* | (2006.01) | |

(52) U.S. Cl.
CPC ...... *A61M 16/0833* (2014.02); *A61M 16/105* (2013.01); *A61B 5/0836* (2013.01); *A61M 16/085* (2014.02); *A61M 16/0825* (2014.02); *A61M 16/1065* (2014.02); *A61M 16/208* (2013.01); *A61M 2202/0208* (2013.01); *A61M 2205/0227* (2013.01); *A61M 2205/18* (2013.01); *A61M 2205/6045* (2013.01); *A61M 2209/06* (2013.01); *A61M 2230/43* (2013.01); *A61M 2230/432* (2013.01)

(58) Field of Classification Search
CPC ...... A61M 2202/0225; A61M 2230/43; A61M 2230/432; A61B 5/0836; A61B 5/097; A62B 18/00; A62B 18/02; A62B 18/04; A62B 18/06; B64D 2231/025
See application file for complete search history.

(56) References Cited

U.S. PATENT DOCUMENTS

| | | | |
|---|---|---|---|
| 4,328,797 A * | 5/1982 | Rollins, III | A61M 16/06 128/202.15 |
| 4,475,559 A | 10/1984 | Horn | |
| 5,280,780 A | 1/1994 | Abel | |
| 5,400,781 A | 3/1995 | Davenport | |
| 5,431,158 A | 7/1995 | Tirotta | |
| 5,474,060 A * | 12/1995 | Evans | A61B 5/097 128/204.22 |
| 5,511,541 A | 4/1996 | Dearstine | |
| 5,857,460 A | 1/1999 | Popitz | |
| 6,247,470 B1 | 6/2001 | Ketchedjian | |
| 6,263,874 B1 | 7/2001 | LeDez et al. | |
| 6,379,312 B2 | 4/2002 | O'Toole | |
| 6,386,196 B1 | 5/2002 | Culton | |
| 6,386,198 B1 | 5/2002 | Rugless | |
| 6,439,234 B1 | 8/2002 | Curti et al. | |
| 6,659,102 B1 * | 12/2003 | Sico | A61M 16/06 128/201.22 |
| 6,849,049 B2 | 2/2005 | Starr et al. | |
| 6,892,729 B2 * | 5/2005 | Smith | A61M 16/06 128/202.27 |
| 7,004,168 B2 | 2/2006 | Mace et al. | |
| 7,146,980 B2 | 12/2006 | Loncar | |
| 7,152,604 B2 | 12/2006 | Hickle et al. | |
| 7,305,988 B2 | 12/2007 | Acker et al. | |
| 7,559,323 B2 | 7/2009 | Hacke et al. | |
| 7,607,433 B2 | 10/2009 | Silva et al. | |
| 7,621,272 B2 | 11/2009 | Orr | |
| 8,365,734 B1 | 2/2013 | Lehman | |
| 2003/0024533 A1 * | 2/2003 | Sniadach | A61M 16/06 128/205.25 |
| 2003/0079751 A1 * | 5/2003 | Kwok | A61M 16/06 128/206.15 |
| 2004/0040556 A1 * | 3/2004 | Fillyaw | A61M 16/0488 128/202.16 |
| 2005/0257791 A1 | 11/2005 | Biederman | |
| 2006/0081248 A1 | 4/2006 | McDonald | |
| 2006/0102185 A1 * | 5/2006 | Drew | A61M 16/06 128/207.13 |
| 2007/0023040 A1 | 2/2007 | Nashed | |
| 2007/0107733 A1 | 5/2007 | Ho et al. | |
| 2007/0125384 A1 * | 6/2007 | Zollinger | A61M 16/06 128/206.24 |
| 2008/0053449 A1 | 3/2008 | Lindblom et al. | |
| 2008/0196715 A1 * | 8/2008 | Yamamori | A61B 5/0836 128/203.12 |
| 2009/0211574 A1 * | 8/2009 | Sniadach | A61M 16/0488 128/200.26 |
| 2010/0051034 A1 * | 3/2010 | Howard | A61M 16/06 128/206.27 |
| 2010/0154798 A1 * | 6/2010 | Henry | A61M 16/06 128/206.24 |
| 2010/0258133 A1 | 10/2010 | Todd et al. | |
| 2011/0100368 A1 | 5/2011 | Taylor-Kennedy | |
| 2011/0148097 A1 * | 6/2011 | Ping | A61M 16/08 285/125.1 |
| 2012/0172740 A1 | 7/2012 | Hu | |
| 2012/0271187 A1 * | 10/2012 | McNeill | A61M 16/04 600/532 |
| 2013/0060157 A1 | 3/2013 | Beard | |
| 2013/0152369 A1 * | 6/2013 | Kwok | A61M 16/06 29/451 |
| 2014/0158136 A1 * | 6/2014 | Romagnoli | A61M 16/0683 128/206.24 |
| 2014/0196726 A1 * | 7/2014 | Mallek | A61M 16/0816 128/861 |
| 2014/0230821 A1 * | 8/2014 | Warters | A61M 16/06 128/205.25 |
| 2014/0243698 A1 | 8/2014 | Koch | |
| 2014/0332005 A1 * | 11/2014 | Kunz | A61M 16/0666 128/205.25 |
| 2015/0217075 A1 | 8/2015 | Nair | |
| 2016/0067438 A1 * | 3/2016 | Rollins, III | A61M 16/0605 128/203.29 |
| 2017/0189635 A1 * | 7/2017 | Beard | A61M 16/01 |

FOREIGN PATENT DOCUMENTS

| | | |
|---|---|---|
| WO | 98/32411 A1 | 7/1998 |
| WO | 2012/030721 A1 | 3/2012 |
| WO | 2012/094730 A1 | 7/2012 |
| WO | WO 2013021172 A1 * | 2/2013 ........... A61B 5/0836 |
| WO | 2014/124323 A1 | 8/2014 |

* cited by examiner

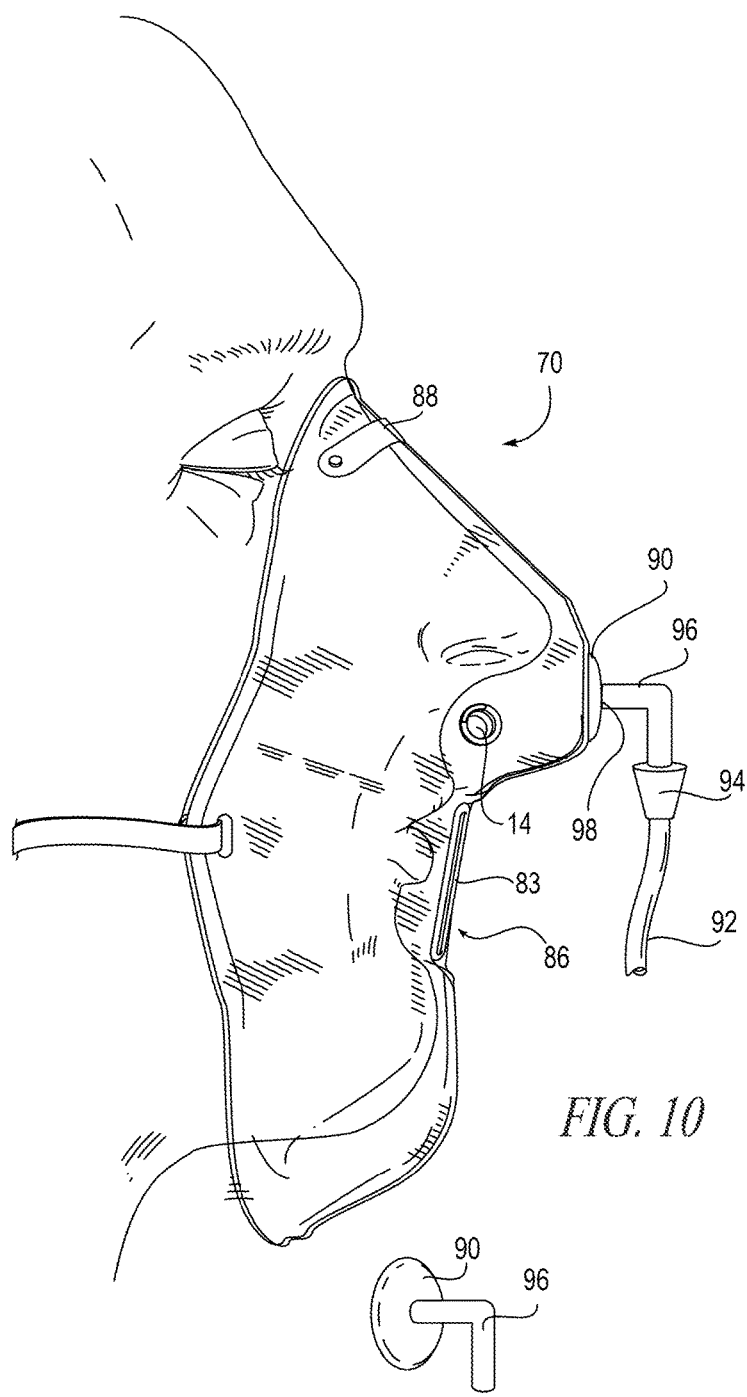

OXYGEN FACE MASK AND COMPONENT SYSTEM

BACKGROUND

Technical Field

The present disclosure pertains to medical face masks for delivering oxygen to a patient and, more particularly, to components, systems, and methods using oxygen delivering face masks to monitor selected patient conditions.

Description of the Related Art

A steady inflow of oxygen is required to sustain human life. A short interruption or reduction in a person's oxygen supply can rapidly lead to brain or body damage, or death. An individual with too little oxygen in his blood (hypoxemia) or at risk for developing hypoxemia may be given oxygen. An individual able to breathe on his own may be given supplemental oxygen therapy for various reasons and in various places. Oxygen may be given to an individual who has shortness of breath or COPD (chronic obstructive pulmonary disease). Supplemental oxygen may be delivered to a patient who has suffered trauma or an acute myocardial infarction (heart attack). Supplemental oxygen may be given during certain surgical interventions or during post-anesthesia recovery after a surgical intervention. Supplemental oxygen may be given anywhere. It may be given, for example, in a person's home, in a clinic or in a hospital such as in a trauma center, an emergency room, an operating room, a recovery room, or an intensive care unit. A person who is receiving supplemental oxygen therapy is generally weak, injured, or compromised in some way. Such a person is prone to stop breathing briefly or altogether. In order to determine if a person receiving supplemental oxygen is continuing to breathe, an assay may be performed. A non-invasive, expiratory gas sampling device may be used to determine if the person is exhaling as evidence he is continuing to breathe. Commonly, the expiratory gas sampled is carbon dioxide.

Both face masks and nasal cannula have been used to deliver supplemental oxygen and to sample carbon dioxide. U.S. Pat. No. 5,400,781 to Davenport discloses an oxygen mask with two openings in the floor of the chamber in front of the mouth that lead to an oxygen source and a carbon dioxide monitor. U.S. Pat. No. 5,474,060 to Evans describes an oxygen mask with an inlet for directing a flow of gas (oxygen) to the interior of the mask, and a port for allowing the exhaled air to flow through and a tube for directing the exhaled air to a monitoring apparatus. U.S. Pat. No. 6,247,470 to Ketchedjian uses a flexible lever arm near the face and connected to tubing to deliver oxygen and sample exhaled gases. U.S. Pat. No. 6,439,234 to Curti describes a nasal cannula with two prongs, with the first prong for delivering oxygen and the second prong for sampling carbon dioxide. WO 91/14469 teaches a nasal gas cannula and an oral gas capture member for delivering and capturing carbon dioxide.

Although these face masks and cannulas attempt to solve some of the problems with delivering oxygen to an individual and determining if he is breathing, none provides an easy to use, universal device that can deliver oxygen and sample an expiratory gas in a variety of circumstances. The present disclosure is directed to meeting these, as well as other, needs.

BRIEF SUMMARY

Described herein are devices, methods, systems, and kits useful for administering oxygen or sampling gases from a mammalian body. The devices are particularly useful for sampling carbon dioxide, though they may be used as a part of any appropriate treatment procedure. Also described are connectors that can be used, for example, with a face mask and face mask assemblies as well as methods for making face masks assemblies and methods of attaching a connector to a face mask along with various components for controlling gas flow between the interior and exterior of the face mask and into and out of components attached to the face mask connector.

One aspect of the disclosure provides a face mask to cover a user's nose and at least partially cover a user's mouth. In some embodiments, the face mask includes two or more lateral ports on opposing sides of a midline of the face mask and is configured to deliver oxygen to a user. In some embodiments, the face mask includes an oxygen inlet port having a center, and at least one of the ports is at least about 20 mm away from the center of the oxygen inlet port. In some embodiments, the face mask includes a conduit coupled to a port on only one side of the face mask.

In some embodiments, the face mask includes at least one vent configured to release gas from the face mask. In some embodiments the vent has a vent center and a center of the port is within about 15 mm of the vent center. In some embodiments, the face mask includes a plurality of vents and the plurality of vents is arranged around one of the ports.

In some embodiments, the face mask includes a mask reservoir portion for containing a pocket of gas and a lateral port is in the mask reservoir portion. In some embodiments, the face mask is configured to removably connect with a user's face to create a mask sealing portion configured to retain gas in the face mask.

In some embodiments, the face mask includes a first removable cap configured to seal a sensor port on an anesthesia breathing machine. In some embodiments, the first removable cap is disposed on a first of the two lateral ports, and in other embodiments a second removable cap is configured to be disposed on a second of the two lateral samplings ports.

Another aspect of the disclosure provides a breathing mask system including a face mask and a sensor and the face mask includes one and preferably at least two lateral ports on opposing sides of a midline of the face mask. The breathing mask may be configured to cover a user's nose and at least partially cover a user's mouth. The sensor may be coupled to a lateral port. In some embodiments, the sensor is configured to detect an expiratory gas. In some embodiments, the system may include an alarm configured to provide a signal when a level of an expiratory gas detected by the sensor is different from a threshold amount. In some embodiments, the sensor is configured to detect a carbon dioxide pressure (e.g., a carbon dioxide partial pressure). In some embodiments, the face mask may include an oxygen inlet port.

Another aspect of the disclosure provides a method of using an oxygen face mask having at least one and preferably two lateral ports on opposing sides of a midline of the face mask to sample an expiratory gas, the method including the steps of choosing one lateral port; and coupling a conduit with the port. In some embodiments, the method includes the additional step of coupling an expiratory gas sensor to the conduit. In some embodiments, the expiratory gas sensor is configured to assay carbon dioxide and the method includes the step of assaying a partial pressure of carbon dioxide.

In some embodiments, the method includes the step of venting expiratory gas through a vent in the face mask. In some embodiments, the method includes the step of administering at least one of a nebulizer treatment and an aerosol treatment. In some embodiments, the method includes the step of providing at least about 60% oxygen. In some embodiments, the method includes expelling expiratory gas through a one-way valve.

Another aspect of the disclosure provides a kit including a face mask having at least one and preferably two lateral ports on opposing sides of a midline of the face mask. The face mask may be configured to provide oxygen. In some embodiments, the kit may additionally include one or more instructions for use, a sampling conduit, a sensor, an oxygen conduit, a rebreather reservoir, and a one way valve.

Another aspect of the disclosure provides a method of using a face mask and an anesthesia breathing circuit, the face mask including at least one port to sample an expiratory gas from a user and the anesthesia breathing circuit configured to provide an anesthetic agent and positive pressure ventilation to the user, the method including the steps of removing a cap from a port on the face mask, removing a sampling conduit from a sensor port on the anesthesia breathing circuit to thereby expose an opening on the sensor port, coupling the cap to the sensor port to thereby close the opening on the sensor port, and coupling the sampling conduit to the port on the face mask.

In some embodiments, the method includes the step of coupling a gas sensor to the sampling conduit. In some embodiments, the method includes the step of analyzing an expiratory gas using the gas sensor (e.g., analyzing a level of carbon dioxide).

In some embodiments, the method includes the step of administering at least one of a nebulized treatment and an aerosol treatment. In some embodiments, the method includes the step of providing a gas including at least about 60% oxygen.

Another aspect of the disclosure provides a face mask to deliver an oxygen gas to a user, the face mask including a connector for connecting a gas conduit with a port on the face mask, wherein the connector is configured to move with at least two degrees of freedom. In some embodiments, the connector is configured to move with at least two degrees of freedom relative to a point on the port. In some embodiments, the connector is configured to move with at least two degrees of freedom when the gas conduit is connected with the connector.

In some embodiments, at least a portion of the gas conduit is configured to move with the connector when the gas conduit is connected with the connector.

In some embodiments, the connector is configured to rotate with at least two degrees of freedom. In some embodiments, the connector includes a rounded portion mating with a mating piece on the face mask, such as, for example a ball-shaped end mating with the mating piece on the face mask.

In some embodiments, the face mask includes an opening in the connector, the opening configured to allow a gas to pass therethrough.

In some embodiments, the face mask includes a hold mechanism configured to hold at least one of the connector and the gas conduit in a preferred location.

In some embodiments, the gas conduit includes a stiff region within about two inches from the connector that is stiffer than a stiffness of another portion of the gas conduit. In some embodiments, an elbow in the stiff region defines an angle between about 90 degrees and about 150 degrees.

In some embodiments, the face mask is configured to cover the user's nose and at least partially cover the user's mouth. Some embodiments include an adhesive material configured to removably attach an outer portion of the face mask to the user's face.

In some embodiments, the face mask includes at least one port. In some embodiments, the face mask includes two lateral ports on opposing sides of a midline of the face mask.

In some embodiments, a material of the face mask includes a flame resistant material, such as, for example, polyvinyl fluoride.

Another aspect of the disclosure provides face mask configured to deliver oxygen to a user, including a superior mask portion having two opposing lateral sides and a bottom side, wherein the superior mask portion is adapted to cover the user's nose and the bottom side is adapted to be superior to the user's mouth when the face mask is in position on the user; an inferior mask frame portion connected with the superior mask portion and surrounding a generally central open portion, wherein the generally central open portion is adapted to be over the user's mouth when the face mask is in use on the and wherein a material of the inferior mask frame portion is sufficiently stiff to maintain the generally central open portion in a particular size and a particular shape during face mask use on a user; and an oxygen port for delivering oxygen to the user.

In some embodiments, an area of the generally central open portion is larger than the user's mouth. In some embodiments, an area of the generally central open portion is larger than about 4 $cm^2$.

Some embodiments include at least one port. Some embodiments include two lateral ports on opposing sides of a midline of the face mask. In some embodiments, the oxygen port is in the superior mask portion.

Some embodiments include a gas conduit coupled with the oxygen port wherein the gas conduit includes a stiff region within about two inches from the oxygen port that is stiffer than a stiffness of another portion of the gas conduit. In some embodiments, the stiff region defines an angle between about 80 degrees and about 150 degrees, such as, for example, an angle of about 90 degrees. In some embodiments, the stiff region is configured to rotate while the face mask is in use on the user, such as, for example, up to 360 degrees.

In some embodiments the two opposing lateral sides of the superior mask portion and the inferior mask frame portion are shaped to contact the user's face when the mask is in use on the user. Some embodiments include a strap coupled with the two opposing lateral sides of the superior mask portion configured to wrap around the head of the user and thereby hold the face mask in place when the face mask is in use by the user.

In some embodiments, at least a part of the inferior mask frame portion includes a material with a stiffness greater than a stiffness of a material in the superior mask portion. In some embodiments, a material of the inferior mask frame portion is configured to maintain the generally central open portion in a particular size and a particular shape in the absence of an applied opposing force.

Another aspect of the disclosure provides method of using a face mask, the face mask including a superior mask portion having two opposing lateral sides and a bottom side, wherein the superior mask portion is adapted to cover the user's nose and the bottom side is adapted to be superior to the user's mouth when the face mask is in position on the user, and an inferior mask frame portion connected with the superior mask portion, including a mask frame around a generally central open portion, wherein the generally central open portion is adapted to be over the user's mouth when the face mask is in use on the user and has an initial size and an initial shape, the method including the steps of positioning the face mask on a user; and inserting a device through the generally central open portion while maintaining the initial size and the initial shape of the generally central open portion.

Another aspect of the disclosure provides a face mask assembly, including a face mask to cover a user's nose and at least partially cover a user's mouth and configured to deliver oxygen to a user, the face mask including a port having a non-circular cross-sectional shape, the face mask further comprising an engagement portion surrounding the port in a wall of the mask; and a mask connector connected with the port, the mask connector configured to connect with a mating connector and having a first end, an external flange distal to the first end, a neck region distal to the external flange, and a second end distal to the neck region, and a first longitudinal channel continuous from the first end to the second end, wherein the first end is external to the mask, the external flange apposes an outer surface of the wall of the mask, and the neck region passes through the port and apposes the engagement portion.

In some embodiments, the face mask assembly includes an internal flange distal to the neck region of the mask connector wherein the internal flange apposes a portion of the inside of the mask wall and is configured to minimize outward longitudinal movement of the first mask connector relative to the rest of the mask. In some such embodiments, the neck region includes a non-circular cross-sectional shape and the internal flange includes a non-circular cross-sectional shape. In some such embodiments, the port, the neck region and the internal flange include substantially ellipsoid cross-sectional shapes. In other such embodiments, an outer footprint of the internal flange is smaller than an outer footprint of the port and wherein the neck region does not substantially rotate relative to the mask when the connector is in place in the port.

In some embodiments, the face mask assembly includes an adhesive material holding the external flange of the first connector and an outer wall portion of the mask together.

In some embodiments, the port is a first port and the mating connector is a first mating connector, the face mask further includes a second port connected with a second mask connector, the second mask connector configured to connect with a second mating connector, wherein the second port and second mask connector are on an opposing side of a midline of the face mask from the first port and first mask connector, and the second mask connector has a first end, an external flange distal to the first end, a neck region distal to the external flange, and a second end distal to the neck region, and a first longitudinal channel continuous from the first end to the second end, wherein the first end is external to the mask, the external flange apposes an outer surface of the wall of the mask, and the neck region passes through the port and apposes the engagement portion.

In some embodiments, wherein the mask connector includes a first luer connector, the assembly further includes a mating luer connector having a second longitudinal channel, wherein the first luer connector and the mating luer connector are connected to thereby form a continuous longitudinal channel from the first longitudinal channel to the second longitudinal channel.

Another aspect of the disclosure provides a method of attaching a mask connector to a face mask including the steps of: passing an internal flange of a mask connecter through a port in a wall of the face mask wherein the connector includes a first end, an external flange distal to the first end, a neck region distal to the external flange, the internal flange distal to the neck region, a second end distal to the internal flange, and a longitudinal channel continuous from the first end to the second end and configured to sample a respiratory gas when the mask is in place on the user, the face mask further including an engagement portion surrounding the port and having a non-circular cross-sectional shape; rotating the connector to thereby appose the internal flange with an inside wall portion of the face mask and thereby limit outward longitudinal movement of the connector relative to the face mask; apposing the neck region to the engagement portion to thereby limit rotational movement of the connector relative to the face mask; and apposing the external flange with an outside wall portion of the face mask to thereby limit inward longitudinal movement of the connector relative to the face mask.

In some embodiments, the passing step includes passing the internal flange of the mask connector through a port in a wall of the face mask without deforming either the internal flange or the port. In some embodiments, the method further includes the step of creating the port (such as, e.g., by punching a hole) in the wall of the face mask prior to the passing step.

In some embodiments, the creating step includes creating the port in a lateral region of the face mask. In some embodiments wherein the port is a first port, the method further including creating a second port in a lateral region of the face mask on an opposing side of a midline of the face mask from the first port, and repeating the passing, rotating, apposing the neck region, and apposing the external flange steps on the second port to thereby attach the second connector with the second port in the face mask.

In some embodiments, the passing step includes passing the connector through a lateral region of the face mask and surrounding the connector with a plurality of exhalation vents.

In some embodiments, the method further includes the step of adhering the external flange surface to the outside portion of the wall of the face mask with an adhesive material.

Another aspect of the disclosure provides a method of attaching a mask connector to a face mask including the steps of: passing an internal flange of a mask connecter through a port in a wall of the face mask wherein the connector includes a first end, an external flange distal to the first end, a neck region distal to the external flange, the internal flange distal to the neck region, a second end distal to the internal flange, and a longitudinal channel continuous from the first end to the second end and configured to sample an expiratory gas when the mask is in place on the user, the face mask further including an engagement portion surrounding the port wherein passing includes elastically deforming at least one of the internal flange and the engagement surface; apposing the internal flange with an inside wall portion of the face mask to thereby limit outward longitudinal movement of the connector relative to the face mask; and apposing the external flange with an outside wall portion of the face mask to thereby limit inward longitudinal movement of the connector relative to the face mask.

Another aspect of the disclosure provides a first luer connector including a first end with a mating portion configured to mate with a second luer connector; an external flange distal to the first end having a substantially flat distal surface and defining an external flange footprint; a neck region distal to the external flange having a non-circular cross-sectional shape and a neck region footprint wherein the external flange footprint is larger than the neck region footprint; an internal flange distal to the neck region and having a substantially flat proximal surface; a second end distal to the internal flange; and a longitudinal channel continuous from the first end to the second end.

In some embodiments, the neck region cross-sectional shape defines a first ellipsoidal shape and a cross-sectional shape of the internal flange defines a second ellipsoidal shape wherein the first ellipsoidal shape is in a rotated position relative to the second ellipsoidal shape. In some embodiments, a neck region non-circular total cross-sectional area is within 10% of an external flange total cross-sectional area.

Another aspect of the disclosure provides first luer connector including: a first proximal end including a mating portion configured to mate with a second luer connector; an external flange distal to the first proximal end and configured to encircle a port and oppose a portion of an external face mask wall proximal to the port in an oxygen face mask when the first luer connector is in place on the mask and to thereby limit inward longitudinal movement of the connector relative to the face mask; a neck region distal to the external flange, the neck region having a non-circular cross-sectional shape and configured to appose an engagement surface of the port when the luer is in place on the mask and the neck region spans the port, the neck region configured to limit rotational movement of the connector relative to the face mask; an internal flange distal to the neck region wherein the internal flange is configured to oppose an internal portion of a face mask wall in proximity to the port to thereby limit outward longitudinal movement of the connector relative to the face mask; a second end distal to the internal flange; and a longitudinal channel continuous from the first end to the second end.

Another aspect of the disclosure provides face mask to cover a user's nose and at least partially cover a user's mouth and configured to deliver oxygen to a user, the face mask including a port having a non-circular cross-sectional shape. In some such embodiments wherein the port includes a first port, the face mask further includes a second port having a non-circular cross-sectional shape, wherein the first and second ports are on opposing sides of a midline of the face mask. The ports may be of same thickness as the mask wall and serve to allow passage of the end of a component, such as a gas sample line, and hold that component in place through their geometry without a connector system such as a luer. The ports may of greater or lesser thickness that the mask wall and be created at the time of the manufacturing of the mask such as during an injection molding process.

In accordance with another aspect of the present disclosure, a face mask for delivering oxygen is provided that includes at least one port with a connector, preferably of the Luer type, and a component system having at least one component for attachment to the connector. The at least one component includes one or more from among a colorimetric $CO_2$ detector, a sealing cap with or without a resilient sealing flap, a capnography gas analysis unit, a non-rebreather valve, a pulmonary function module, nebulizer, a gas scavenging system, a gas reservoir system, a gas filter, sample lines that are either straight or at an angle, and an aerosol mask platform. In addition, alternative methods of attaching the mask fitting to the mask are also presented.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein:

FIG. 10 shows a side view of a face mask such as the one shown in FIG. 9;

FIGS. 11A-B show a swivel mechanism for a gas conduit for use on a face mask;

DETAILED DESCRIPTION

The present disclosure is directed to a universal oxygen face mask and related component system and methods for delivering oxygen and sampling a respiratory gas for use in a variety of clinical scenarios for an individual able to breathe on his own, but requiring some supplemental oxygen. Respiratory gas (e.g., carbon dioxide) may be monitored using the face mask to ensure that the individual continues to breathe. Ensuring that the individual is breathing may be especially important when an individual is under sedation or has recently experienced a status change such as a surgical procedure or trauma. The face mask may have one, two or more lateral ports for ventilation or \sampling ports for sampling a respiratory gas.

It is to be understood that the location and configuration of the port assembly (e.g., male Luer lock port, vent openings, and circumscribing raised border) relative to other features of the mask include ornamental aspects, such as number and placement relative to other features for symmetry and balance, radius of curvature of the port and vent openings, relative sizes and location of the port and the vent openings as well as the circumscribing raised border around the port and vent openings on the face mask. The aesthetic aspects of the face mask with side port assemblies will make this an attractive feature and will be one element to distinguish the present disclosure from competitive products in the market place.

Figure 1:
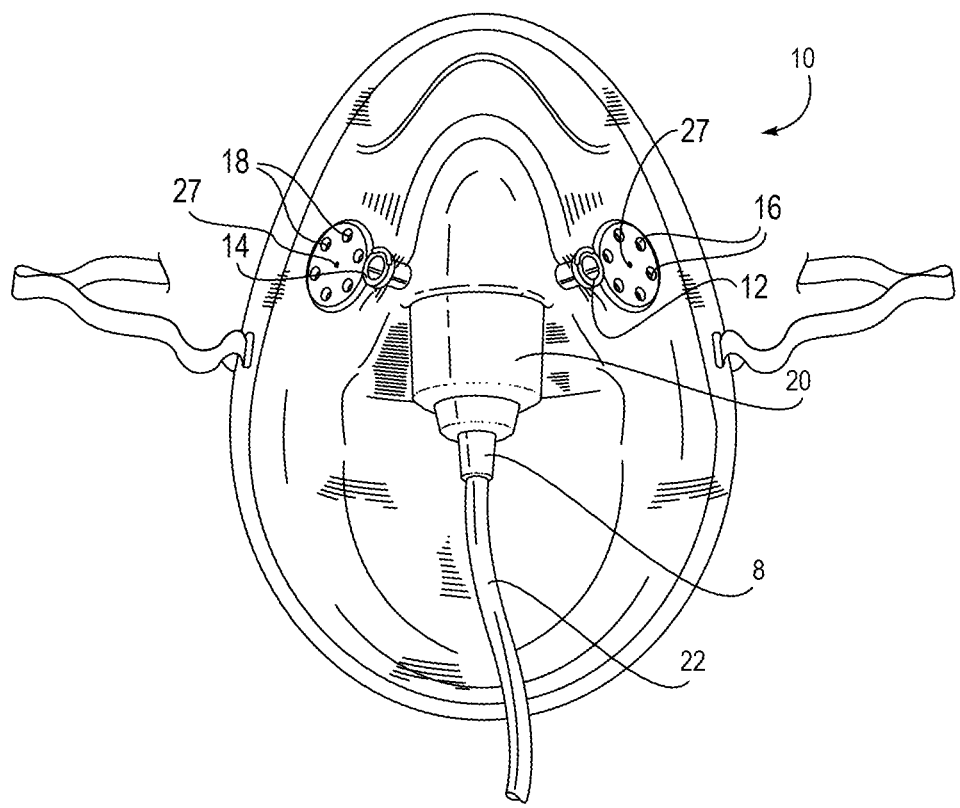
FIG. 1 is a front view of an oxygen face mask with lateral ports according to one aspect of the disclosure.

Each sampling port assembly (referred to at times as "port" or "ports") may be located between a level of the nose and a level of the mouth when the face mask is in use on one or both sides of the mask. The exact location is a matter of design choice for appearance and appeal. FIG. 1 (front view) and FIG. 2 (side view) show a face mask 10 embodying features of the disclosure including left lateral port 12 and right lateral port 14. Having two lateral ports makes the face mask easier to use and allows for better samples to be taken. This may be the case even though, in practice, a sample may be taken from only one of the ports. A second (or additional ports beyond the second) lateral port may be unused. A face mask with two lateral ports allows the mask to be used in nearly all clinical scenarios; face mask manufacturing can be streamlined and the best mask for almost any situation is readily available. A face mask with at least two lateral ports eliminates the need to have a series of different masks for different purposes or reduces the number of different types of masks that may be needed. A face mask having two lateral ports may be the standard for use with most or all patients, and the use of interchangeable components coupled with the face mask for specific clinical scenarios may be the care path.

A face mask according to the disclosure may be useful for a variety of clinical purposes in a variety of settings. A face mask may be used while a person needing oxygen is supine, lateral or prone; while a person's face is covered with a drape; during nebulizer therapy; during use of a non-rebreather mask; during use of an oxygen calibration device (e.g., a Venturi device); or during high flow oxygen therapy. In addition, a face mask could be used for administering oxygen and monitoring an aspect(s) of respiratory physiology, such as end tidal $CO_2$ and respiratory rate during a test of athletic endurance or cardiovascular health.

Ports high on the mask and lateral to the midline of the mask are more accessible. The lateral ports are easy to access in order to attach a sampling conduit (e.g., tubing) in a variety of patient positions and patient-caregiver physical arrangements. If a monitoring port is low on the mask, it may be difficult to gain access to the port. First, accessing a port if the port is in the immediate proximity to the oxygen port is challenging and there is limited space available to manipulate (e.g., attach and detach) a conduit. This could be of particular importance in a small pediatric mask. Secondly, a port located near the oxygen inflow is out of view and cumbersome to reach in the most common operating room scenario, for which the anesthesia provider is positioned at the head of the patient's bed. Any difficulty in accessing the monitoring port is magnified in challenging clinical situations such as an obese, prone, or laterally positioned patient. Additionally, the patient's neck, chin or other body part may get in the way of monitoring port access, especially in the case in which a patient is lying on his side.

Figure 2:
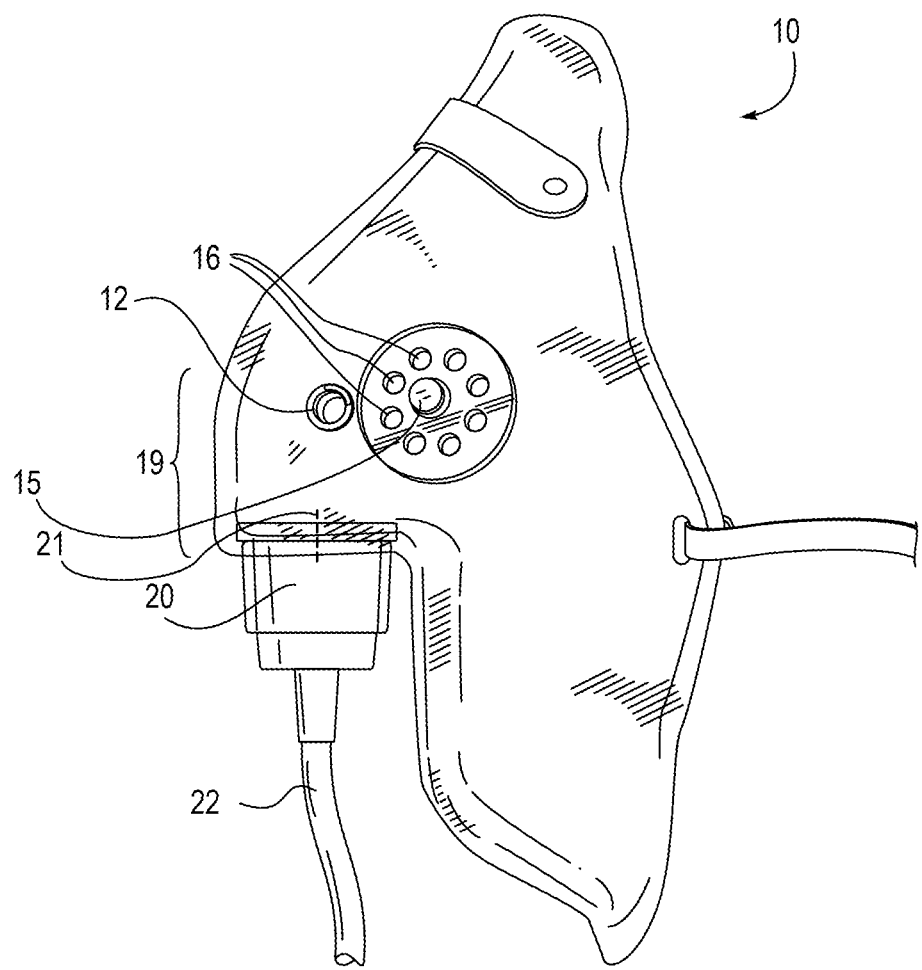
FIG. 2 is a side view of a face mask with a lateral monitoring port according to one embodiment.

The mask design of the disclosure may also achieve the aims of separating the port from the other equipment and from other lines (e.g., an oxygen input port, oxygen conduit, or oxygen bag). This separation prevents or reduces problems with the port interfering with other equipment and lines as well as reducing or preventing problems with other equipment and lines interfering with port access and sampling conduit access. This design also reduces or avoids unnecessary stimulation of the patient by keeping lines and monitors away from the eyes and other sensitive parts of the face. FIGS. 1 and 2 depict left, right lateral ports 12, 14 positioned away from an oxygen inlet port center 21 of oxygen inlet port 20 on face mask 10, and out of the way of oxygen conduit coupler 8, shown coupling oxygen inlet port 20 with oxygen conduit 22. In one example, a center of the lateral port is at least about 20 mm away from oxygen inlet port center 21 of oxygen inlet port 20.

Having two ports available may allow a care provider (e.g., a physician, nurse, or other person) to choose a convenient port. For example, when a patient is lying supine while undergoing a surgical procedure, the care provider performing the respiratory gas monitoring often sits at the patient's head. It is easier for the care provider to access one of the lateral ports and connect a tube or conduit to it for monitoring respiratory gas than it is to access a port that is obscured by the patient's neck and may be underneath the oxygen inlet port/oxygen conduit. Depending on various factors, one specific lateral port may be a better choice for the care provider to use. Ease of attachment may be based on the positions of the care provider or the monitoring equipment to the patient. For example, a lateral side port can be chosen and easily and directly accessed based on ergonomic considerations such as patient position, monitor position, and caregiver position and handedness. In some circumstances, a care provider may not need to reach across the patient's face. As a patient may be conscious during a procedure when wearing an oxygen face mask, this is important. Having a hand close to the eyes may create or worsen a feeling of confinement or claustrophobia in a patient, which are common complaints from oxygen mask users. Passing hands or materials across a patient's face may also put the patient at risk for eye injury.

Having at least two ports on the mask also means that if one of the ports cannot be used, a second monitoring port is still available. This may be the case, for example, when an individual is lying on one side, such as when a surgical procedure is being performed on the other side, and one of the ports is blocked.

In another example, a mask may be used (e.g., to deliver oxygen) without using a sampling port(s) to obtain a sample. In another example, samples could be removed from two (or more than two) sampling ports.

Figure 3:
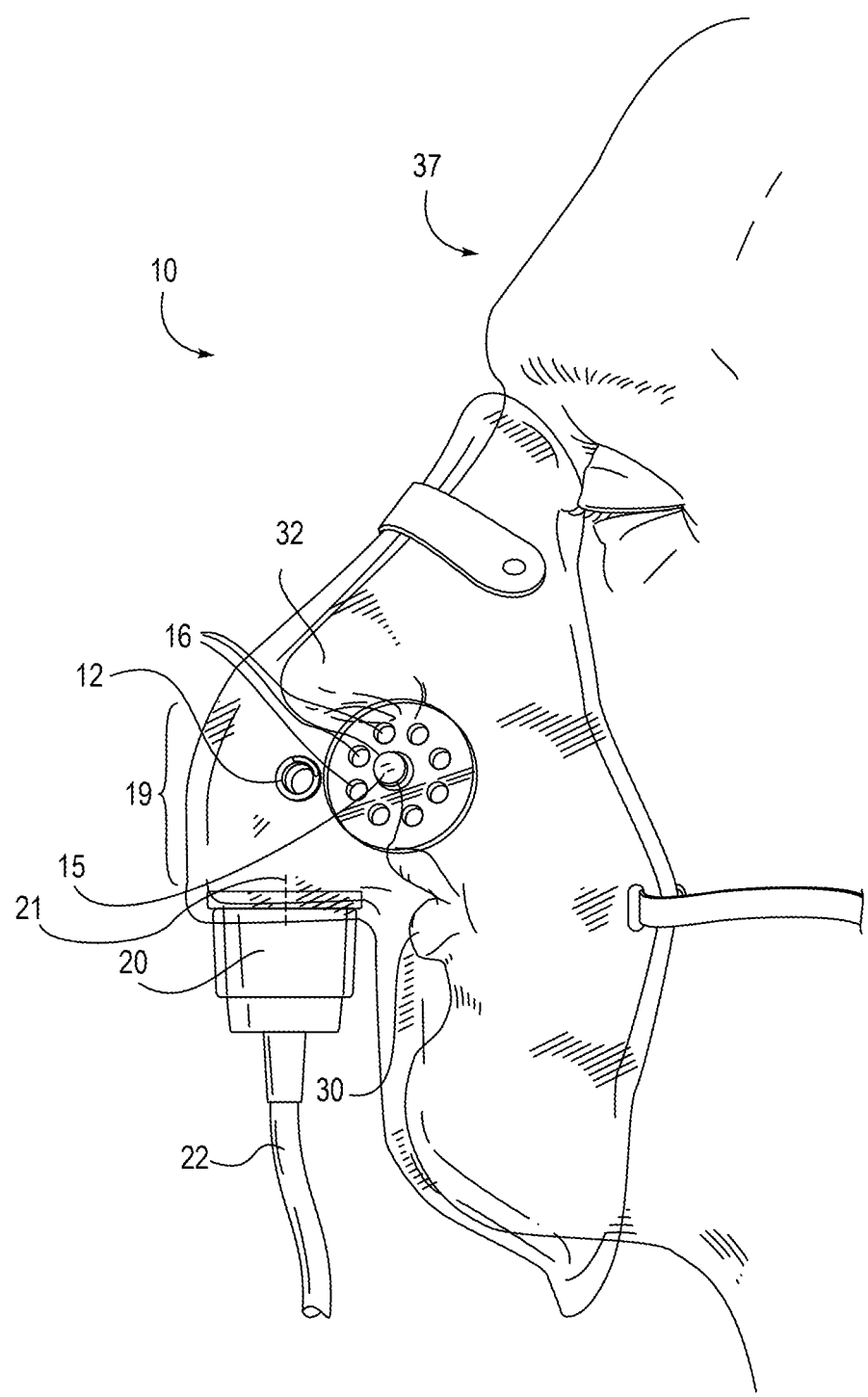
FIG. 3 is a side view of a face mask such as the one shown in FIGS. 1 and 2 in use on a patient.

Ports may be located laterally to the midline of the mask (e.g., on opposing sides of the midline). Ports may be asymmetrically or symmetrically located relative to each other and the midline. The ports may be between a level of the nose and a level of the mouth when the mask is in use. In one example, the ports are at or below the bottom of the nose (e.g., below about a level of the nares) when the mask is in place on a mask user. In another example, the sampling ports are above the level of the lower lip. In another example, the sampling ports are above the level of the upper lip. A sampling port(s) may be positioned in any lateral position relative to the nose and mouth. A port(s) may collect nasal gases, oral gases, or both. The ports may instead or additionally collect other gases (e.g., supplemental oxygen, room air). FIG. 3 shows a side view of patient 37 wearing face mask 10 as described herein. Left lateral sampling port 12 is at a level between mouth 30 and nose 32.

A face mask may have one or more exhalation vents (e.g., exhalation ports). FIGS. 1-3 show left, right exhalation vents 16, 18. An exhalation vent(s) may release or vent gas and other substance(s) from inside to outside the mask. A gas may be an expiratory gas (e.g., carbon dioxide or oxygen). Although called an exhalation vent(s), a vent may additionally allow room air or other materials to move from outside the mask to inside the mask in some embodiments. A vent(s) may move air within the mask and in particular may move air within a reservoir of the mask. A mask may have a vent(s) on a midline of the mask, or on one or both sides of the midline. There may be a plurality of exhalation vents. There may be one, two, or more exhalation vents. In one example there may be 10 or more vents. A lateral sampling port may be located outside an area encompassed by the exhalation vents, as shown in FIGS. 1-3. A lateral sampling port may be located near an exhalation vent. A lateral sampling port may be located as close to one or more exhalation vents as possible, such as left port 12 located near exhalation vents 16 as shown in FIG. 3. In one example, a lateral sampling port may be located about 1 mm away from an exhalation vent. In one example, the distance between a center of a lateral sampling port and a vent is about 15 mm. In another example, a distance between a center of a lateral sampling port and a center of the vents is about 15 mm.

Figure 7:
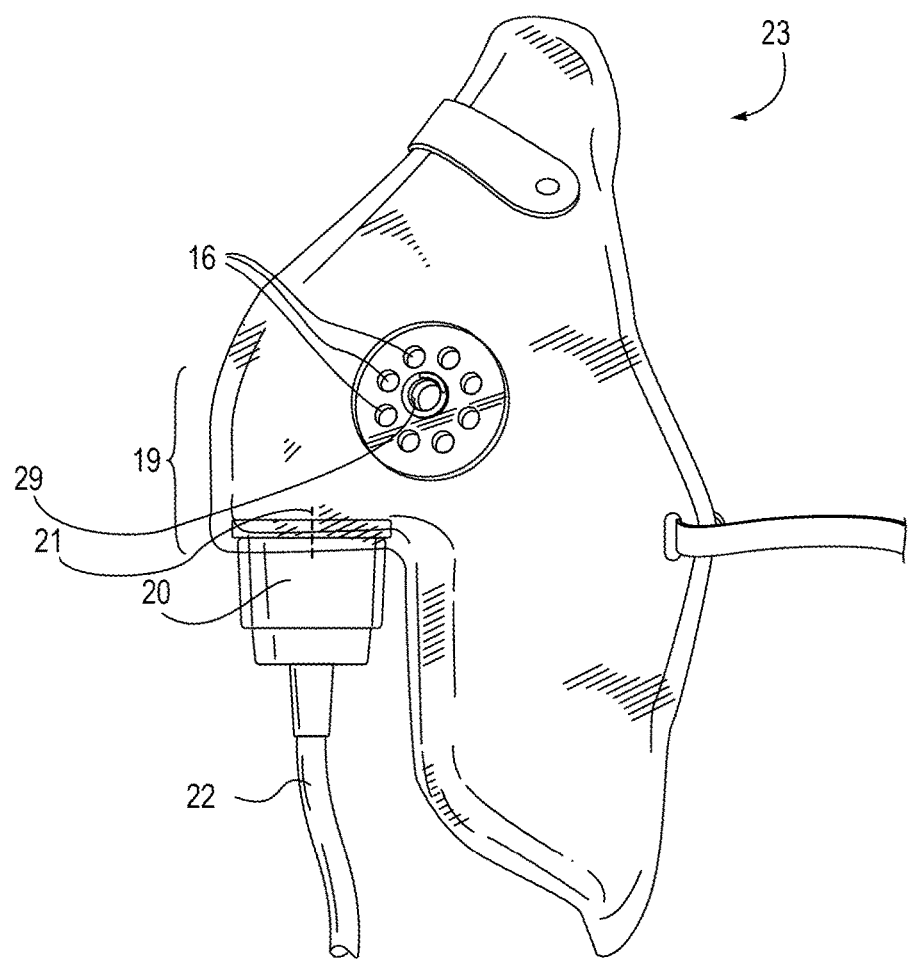
FIG. 7 shows a side view of a face mask with vents arranged around a port.

A plurality of exhalation vents (e.g., perforations) may be arranged around a lateral sampling port. A vent may define a vent center or a plurality of vents may define a vent center 27, as shown on face mask 10 in FIG. 1. A port may be located at or near a vent center, substantially surrounded by exhalation vents. FIG. 7 shows face mask 23 with port 29 surrounded by a plurality of vents 16. In another example, a sampling port is outside an area of the vents and a distance between a center of a sampling port and a center of the vents is about 15 mm.

Figure 8:
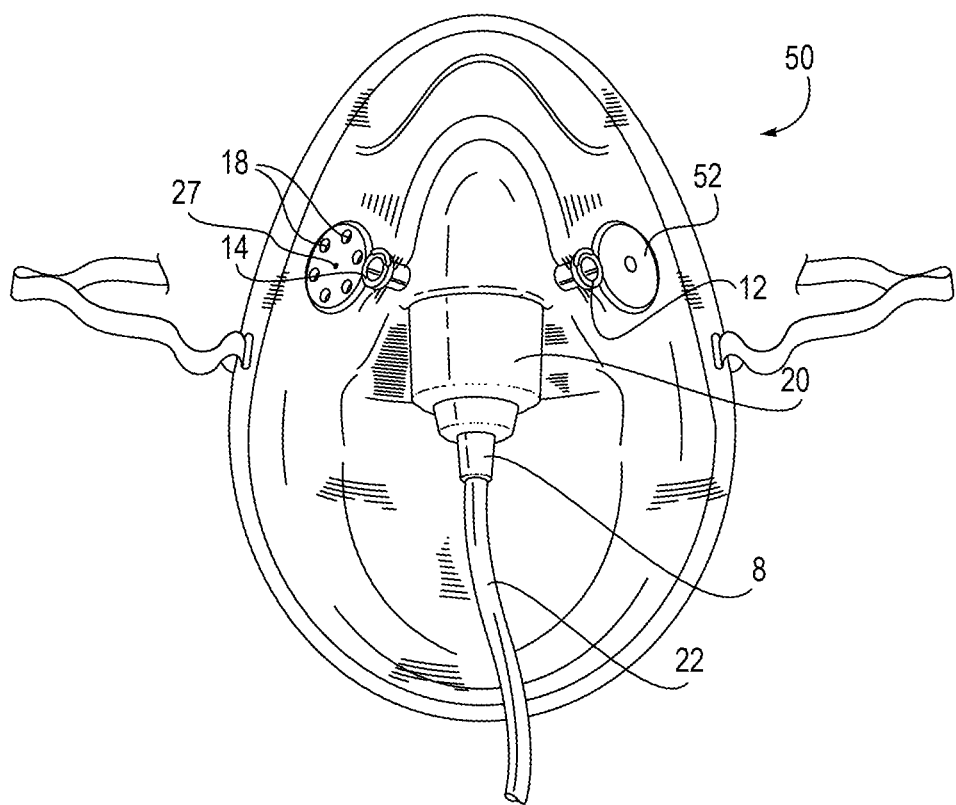
FIG. 8 shows a front view of a face mask with a one-way valve covering a series of vents.

An exhalation vent may have a point of attachment (e.g., a coupling point) 15 near or at a vent center as shown in FIGS. 2 and 3. A flexible diaphragm may be coupled with a point of attachment to create a one way valve (e.g., over the vent(s)). FIG. 8 shows face mask 50 with flexible diaphragm 52 placed over the exhalation vents, creating a face mask with a one way valve. A one way valve may, for example, be used with a non-rebreather apparatus. A one way valve may allow gas inside the mask to move to outside the mask, while substantially not allowing gas outside the mask (e.g., room air) to move inside the mask. Any type of one way valve that allows flow in one direction may be used. For example, a one way valve may be single piece that is placed on or is a part of a face mask.

An exhalation vent may have low resistance to air flow as air flows out of an exhalation hole; locating a lateral port near an exhalation vent may allow more accurate sampling of exhaled gas as the gas is moved past the lateral port. If gas is sampled near an inflow stream of oxygen, the sampling accuracy may be lowered. This may especially be the case in high minute ventilation scenarios in which carbon dioxide levels are low or oxygen flow rates are high.

Mask 10 may have reservoir 19 containing a pocket of gas (e.g., air) as shown in FIGS. 2 and 3. A reservoir may allow gas mixing and provide a space near nose 32 (e.g., near the nostrils) and mouth 30 to facilitate breathing. In one example, a reservoir may extend from a level near the mouth to a level near the nose when the mask is positioned on a user. In another example, a reservoir may extend to about the bottom of the nose when the mask is in use. In one example, the reservoir extends about 50 mm vertically, 50 mm horizontally, and 50 mm in the anterior posterior dimension. A port may be located in a reservoir region of the mask. As shown in FIG. 3, left lateral port 12 exits the mask from reservoir 19.

Positioning a port(s) away from an oxygen inlet port may make it easier (or even possible) for a care provider to change an oxygen conduit (e.g., tubing) leading to an oxygen inlet port or another connector which might not be possible (or might be very difficult) if a port (or conduit connected with a port) is too close to the oxygen delivery port. For example, it may be easier to change a nebulizer device coupled with the oxygen inlet port without having a port nearby that might obstruct access. A port may be positioned far enough away from an oxygen line connector to enable a care provider to attach both a sampling conduit and a specialized apparatus to the mask including a nebulizer, a nonrebreather, an oxygen calibration device (e.g., a Venturi device), or a high flow oxygen source.

A port may have any shape or configuration that allows gas to move through and to connect with a conduit or sampling device. A port may be low profile or may be hardly visible. A port may be e.g., circular, square, hexagonal, or slotted. A port may have a mating part or fitting configured to removably connect with a different mating part or fitting on a conduit, including a sensing conduit. A mating part may be any as known in the art (e.g., threads, slots, pins, lock-and-key mechanism, etc.). In one example, a mating part on the port is a Luer-lock that can couple with a Luer-lock on a port conduit.

Any type of sampling conduit may be used. In one example, sampling conduit is a flexible polyurethane tubing. Sampling conduit may have a narrow diameter; the diameter may be smaller than a diameter of an oxygen conduit. In one example a sampling conduit may have about a ¼ inch inner diameter or ⅜ inch outer diameter.

Figure 4:
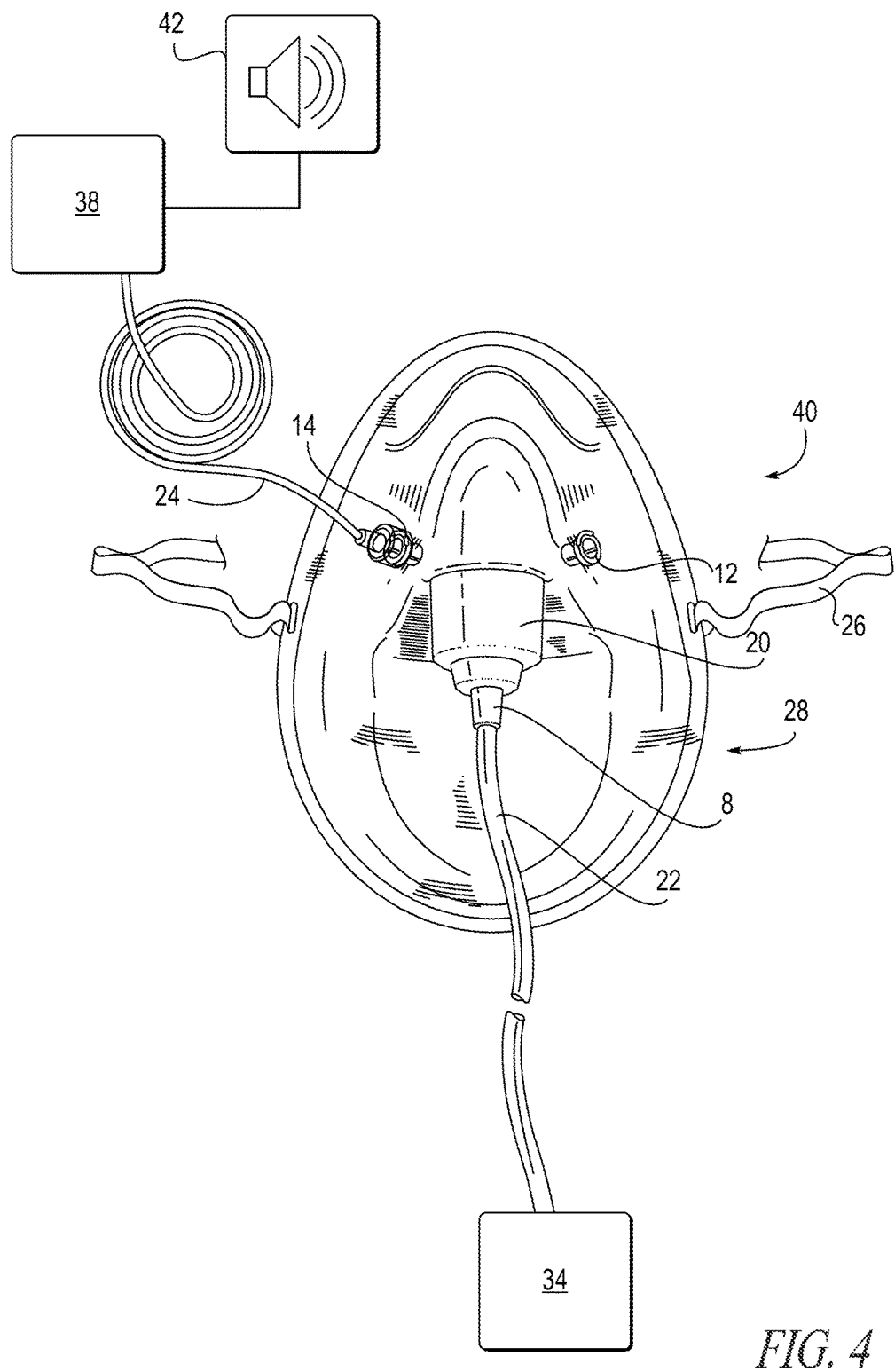
FIG. 4 shows a front view of a face mask with sampling conduit connected to one of the lateral ports.

One method of using an oxygen face mask having two lateral sampling ports or ports according to the current disclosure includes choosing a lateral sampling port or port and coupling a conduit with the lateral sampling port or port. FIG. 4 shows mask 28 with left, right lateral ports 12, 14. Sampling conduit 24 is connected with right lateral port 14 to enable gas (e.g., carbon dioxide) sampling according to a method of the disclosure. The method may further include the step of obtaining a sample from the port. In one example obtaining the sample comprises obtaining a sample without an anesthetic in it (e.g., without an inhaled anesthetic). The method may include the step of coupling an expiratory gas sensor to the conduit; and the expiratory gas sensor may be configured to detect carbon dioxide. The method may include the step of analyzing the sample for a component. The method may include the step of analyzing carbon dioxide (e.g., a partial pressure of carbon dioxide). The method may include the steps of removing the sampling conduit, and reattaching the conduit. The method may include the steps of providing oxygen, venting an expiratory gas, or administering a nebulizer or aerosol agent or treatment.

In some embodiments, the method includes providing at least about 21-100% oxygen. The range includes providing room air (e.g., about 21% oxygen) to providing pure oxygen (e.g., around 100% oxygen), such as deliverable by a nonrebreather or high flow device. In some embodiments, at least about 30%, at least about 40%, at least about 50%, at least about 60% oxygen, at least about 80%, at least about 90%, or more than 90% oxygen is provided. FIG. 4 depicts oxygen source 34 providing oxygen through oxygen conduit 22 to oxygen inlet port 20. An oxygen source can be any as known in the art (e.g., an oxygen tank or a bag connected to an oxygen tank). In one example, monitoring may be performed without providing supplemental oxygen (e.g., only providing room air).

Any material may be sampled from the port. Any characteristic of the material may be analyzed. Gas may be sampled from the port or a component present with the gas may be sampled. A sampled gas may contain other component(s) such a therapeutic nebulized or aerosolized component or agent. A gas may be expired gas. An expired gas may be mixed, in part, with delivered oxygen, or room air before sampling. In one example, a gas may not contain expired air (e.g., if the patient is not breathing). In one example, carbon dioxide is sampled (capnography). In another example, oxygen is sampled. In another example, end tidal partial pressure of the gas (e.g., carbon dioxide) may be measured (or otherwise determined or calculated).

Any device or means (e.g., sensor) may be used to sample a gas. FIG. 4 shows sensor 38 coupled with sampling conduit 24 for analyzing a sample from right lateral port 14. A sensor may be connected to a sampling conduit, or the conduit may be or include the sensor. Any characteristic of a gas may be sensed. An amount of a gas, a change in a level of a gas, or a change in a pressure of a gas may be sensed. A partial pressure of a gas may be assayed. In one example, carbon dioxide is measured and an infrared sensor is used (capnograph). In another case, carbon dioxide may be measured and a colorimetric sensor may be used (see e.g., U.S. Pat. No. 5,857,460 to Popitz).

A system according to the disclosure may include a face mask and one or more components that can be used with the face mask. The system may include a component configured to obtain, move, provide, sense, assay or measure a level of a gas. FIG. 4 shows system 40 with mask 28, sampling conduit 24, sensor 38, oxygen conduit 22, and oxygen source 34. The system may include a mask, a mask sealing agent, a face contact agent (e.g., a lotion), sampling conduit, oxygen conduit, an oxygen reservoir (e.g., partial or full rebreather reservoir), a one way valve or valve cover or an oxygen source (e.g., tank). In one particular example, the system includes a face mask and a sensor configured to detect a characteristic of a gas, such as a carbon dioxide partial pressure. A sensor may be coupled with or configured to be coupled with a lateral port.

Figure 6:
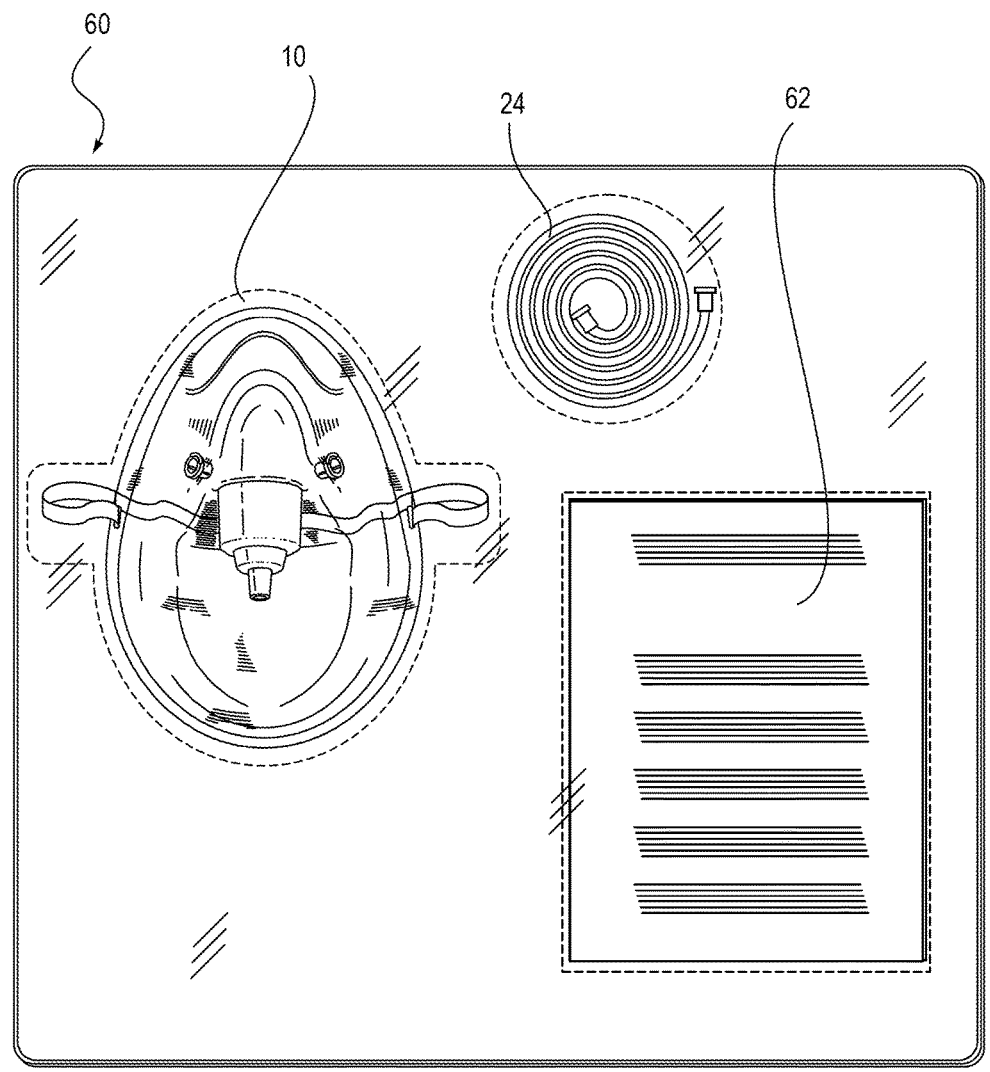
FIG. 6 shows a face mask kit according to one aspect of the disclosure.

A face mask may be packaged into a kit. A kit may have any component configured to be used with the face mask. A kit may include e.g., a face mask, a sampling conduit, a sensor, an oxygen conduit, a rebreather reservoir, a one way valve, or an instruction(s) for use. FIG. 6 shows kit 60 with face mask 10, sampling conduit 24, and instruction for use 62.

A face mask or face mask system or a component used with the face mask may include an alarm, such as alarm 42 shown in FIG. 4. An alarm may provide a signal in response to a result from a component measurement. The alarm may be any (e.g., auditory, vibratory, visual). An alarm may provide a signal when a level of an expiratory gas is at or different from a threshold amount (e.g., is above or below a threshold amount). In one example, the alarm is auditory and provides a signal when a level of carbon dioxide is different from a threshold level (e.g., when a partial pressure of carbon dioxide is below a threshold level).

Any material can be delivered through the mask to the patient that would benefit the individual. Gas (e.g., room air, oxygen, or respired air) may be delivered. Room air, oxygen, or respired air may be delivered with or without also delivering an anesthetic agent and with or without a sample being monitored. Room air may be delivered through vents in the mask, through an oxygen line connector, through another connector, or along an unsealed or open edge of the mask. Room air may be mixed with another gas (e.g., oxygen) and delivered.

In one example, oxygen is delivered through an oxygen inlet port. An amount of oxygen delivered may be any therapeutic amount (e.g., 21-100%). The oxygen may be delivered at any flow (e.g., low, medium, or high flow).

Oxygen may be delivered at a relatively low flow rate. In another example, respired air may be delivered with oxygen. A reservoir or bag configured to supply oxygen and respired air may be coupled with the mask. A mask may have a one way valve on one or more exhalation vents to release expired air to the room (e.g., a rebreather or partial rebreather mask) without substantially allowing room air into the mask.

Oxygen may be delivered to the face mask with little or no exhaled air delivered or remaining in the face mask (e.g., the mask or mask system may be a non-rebreather or partial rebreather mask or mask system). An exhalation vent may include a one-way valve configured to allow the release of gas (e.g., exhaled air) from the mask without allowing intake of room air. In one example, oxygen may be delivered using a reservoir bag. A reservoir bag may be connected with a mask using an oxygen line connector or other connector and may be connected with a source of oxygen (e.g., an oxygen tank). A connection between the reservoir bag and the face mask may include a one way valve that prevents inhaled air from entering the reservoir. Any of the components may be connected with a face mask, or may be separate from a face mask. A system including an oxygen face mask of the disclosure may include one of more components for connecting with or using with a face mask.

Oxygen may be delivered at a relatively high flow or pressure (e.g., 4 to 10 L/min) into the face mask (e.g., a Venturi mask). A high flow may in turn cause a percentage of the oxygen in the face mask to be higher or controlled (e.g., more constant).

Alternatively, a device for creating or delivering a nebulized agent (e.g., a nebulizer) or aerosoled agent may be connected with an oxygen line connector or another connector. Any material may be delivered through a nebulizer device. For example, a bronchodilator or glucocorticoid may be delivered. In one example, albuterol is delivered. In another example, ipratropium may be delivered. This may be especially beneficial for a patient suffering from COPD or asthma.

Figure 15:
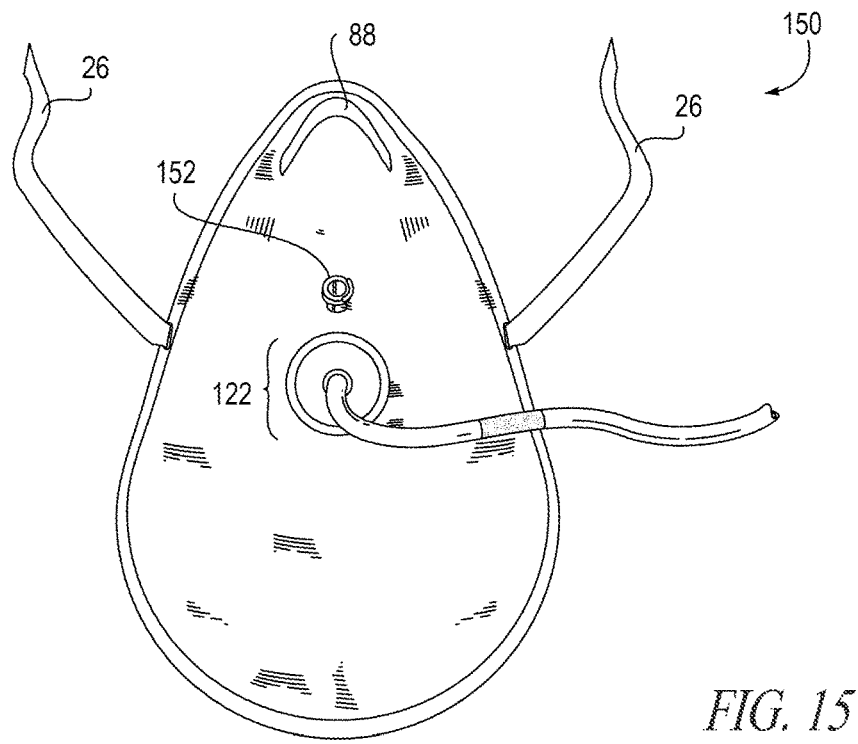
FIG. 15 shows a front view of a face mask with a connector for moving a gas conduit and a single port.
Figure 16:
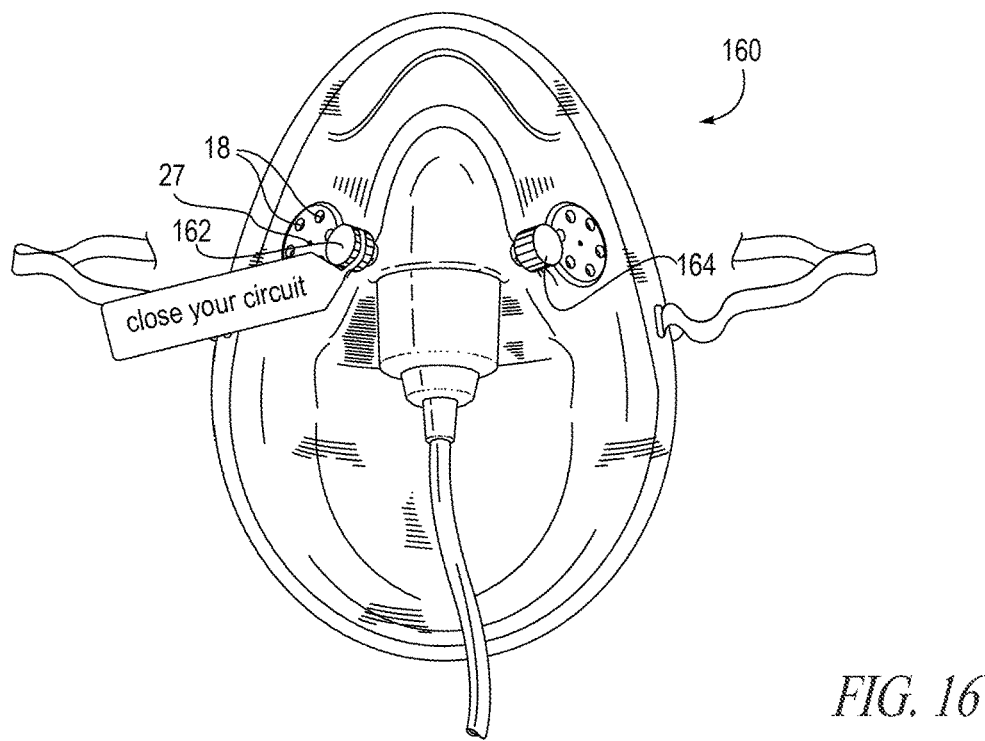
FIG. 16 shows another embodiment of a face mask with a removable cap covering each lateral port.

A face mask could instead have a single sampling port or port 152 located along the midline of the oxygen face mask as shown FIG. 15. A port may be located between the nose and the mouth. A port may be located above and away from a face mask component configured for delivering oxygen. A mask with a low profile port at the midline may be easy to use and minimally obstructive to the patient's view. In one example, the opening of a port may point downwards (e.g., away from the user's eyes).

A face mask may be any shape that fits over a portion of the patient's face to provide oxygen and obtain a gas sample. A face mask may be generally diamond shaped or may be oval. A mask may have features to accommodate contours of the face (e.g., the nose, chin, cheeks). Different masks may have features for different individuals (e.g., large patient, obese patient, pediatric patient). A face mask may be configured to cover the nose and mouth. A mask may cover the nose and part of the mouth. A face mask may cover the nose and all of the mouth. A mask may be configured for use on a mammal (e.g., a human). A face mask may exclude covering the eyes.

Figure 5A:
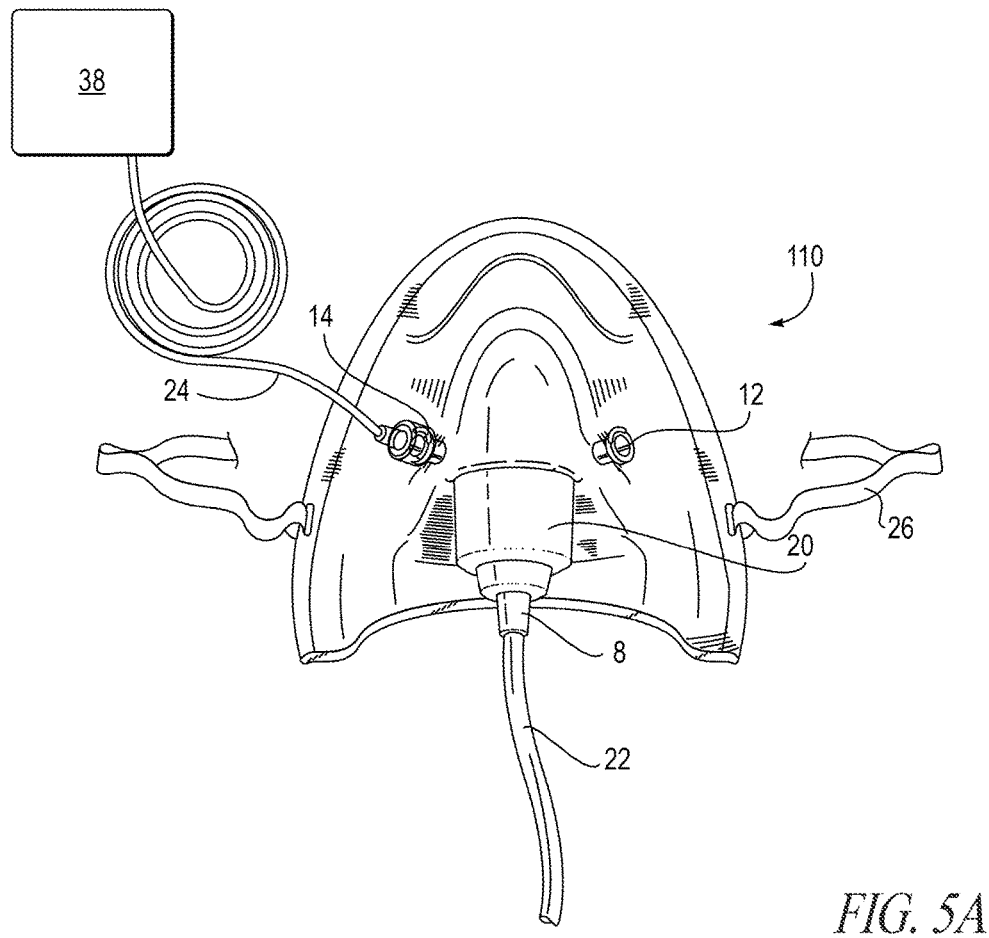
FIG. 5A shows a short face mask to allow access to an individual's mouth and face.
Figure 5B:
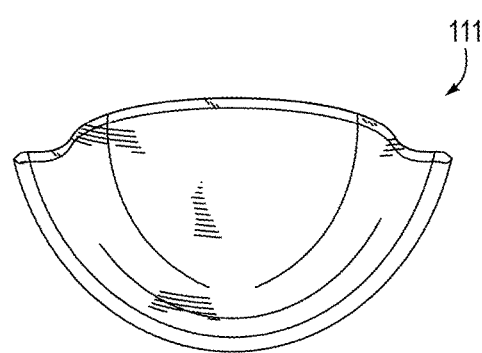
FIG. 5B shows a bottom portion of a face mask removed from a full mask to form the short mask shown in FIG. 5A, according to one aspect of the disclosure.

According to one embodiment, a mask with lateral ports may be a short mask, having a top portion without a bottom portion. A short mask allows access to the lower part of the patient's face (e.g., a patient's mouth). FIG. 5A shows short face mask 110 with various features, including left and right lateral ports 12, 14, strap(s) 26, and oxygen inlet port 20. Right lateral port 14 is connected with sensor 38 through sampling conduit 24 for sampling an expiratory gas. Left lateral port 12 is not being used in this example. A short mask may be directly manufactured, or may be made by cutting a full (e.g., long mask) to remove a bottom portion of the face mask. FIG. 5B shows a bottom portion 111 of a face mask that has been removed from a top portion, to create a face mask such as short face mask 110 shown in FIG. 5A.

In another embodiment, a mask may not have exhalation ports. For example, a mask open at the bottom, such as a short mask shown in FIG. 5 might not need exhalation ports. Masks having a port closer to the bottom of the mask are cumbersome to use in a procedure in which the bottom part of the mask may be removed but expiratory gas(es) still need to be measured. Access to the lower part of the patient's face may be for any reason. A short mask may allow an endotracheal tube, endoscope, or echocardiogram probe to be inserted into the patient's mouth. An endotracheal tube may provide oxygen and anesthesia to the patient. In one example, access to the patient's mouth may allow nourishment or fluids to be provided. In another example, access may allow a procedure to be formed, such as a facial procedure or surgery or dental work.

A mask may be any size to fit an individual. In one example, a mask may be configured to fit onto most average adults. A mask may be configured to fit an especially large or obese individual (e.g., may be larger or may have a different shape). In another example, a mask may be configured to fit a child. In another example, a mask may be configured to fit a baby.

A mask may have a sealing portion to removably seal or connect with the user's face. A sealing portion may retain gas in the mask; a sealing portion may reduce or prevent expiratory gas or oxygen from escaping from a mask. A sealing portion may be an edge portion of the mask. A mask may have special features (e.g., silicone edges, a sealing air pocket, lubricant, etc.) to improve the connection or removal of a mask relative to the face or to make a mask more comfortable when in use.

A mask may have any type of fastener or holder to hold the mask in place (e.g., an elastic loop to go behind the head, loops to go around the ears, etc.).

One aspect of the disclosure is a face mask to deliver oxygen to a user, including a superior mask portion having two opposing lateral sides and a bottom side, wherein the superior mask portion is adapted to cover the user's nose and the bottom side is adapted to be superior to the user's mouth when the face mask is in position on the user, and an inferior mask frame portion connected with the superior mask portion and surrounding a generally central open portion, wherein the central open portion is adapted to be over the user's mouth when the face mask is in use on the user, and an oxygen port for delivering oxygen to the user. A face mask with an open portion may provide better access to a user's face, mouth, or nose for diagnostic equipment, medical devices, surgical equipment, or a caregiver's hands. A face mask with an open portion may provide better visibility to a caregiver for performing a procedure. A face mask with an open portion may be especially useful for performing a procedure on or near the user's face or through the face mask, such as a dental procedure, an esophageal procedure, a facial procedure, or another oral procedure. In a particular example, endoscopy may be performed.

Figure 9:
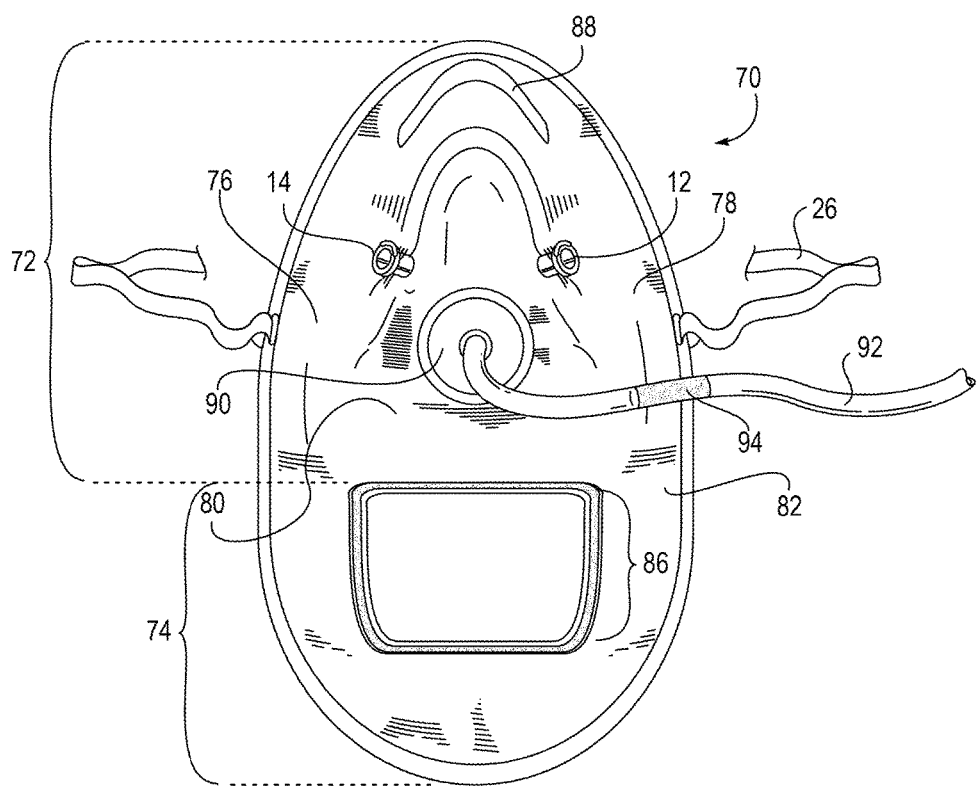
FIG. 9 shows a front view of another face mask with an opening in the front.
Figure 12:
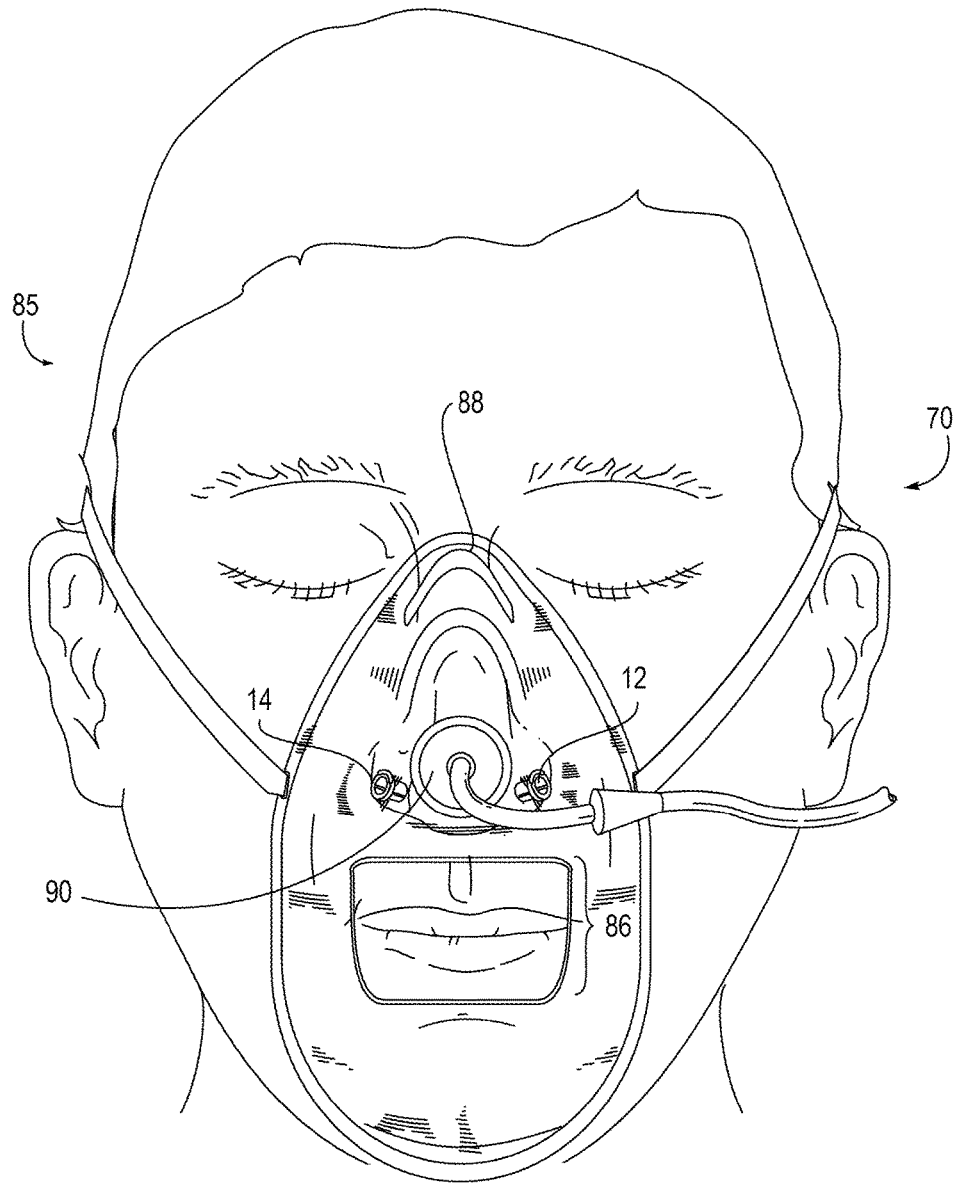
FIG. 12 shows a face mask such as the one shown in FIG. 10 on a user.

FIGS. 9, 10, and 12 show face masks with a generally central open portion. FIG. 9 shows a front view of a mask with a central open portion, and FIGS. 10 and 12 show front and side views of a mask with a central open portion in position on a user. Mask 70 has a superior mask portion 72 and an inferior mask frame portion 74 with an opening 86. Superior mask portion 72 includes first lateral side 76 and second lateral side 78 on an opposing side of the midline from the first lateral side, and bottom side 80. Superior mask portion 72 is superior to a user's mouth when the face mask is in position on a user. Superior mask portion 72 has reservoir 99, a space that may provide a gas and comfort and ease of breathing. Superior mask portion may be contoured or shaped to contact or encompass a user's face when the mask is in use on the user. In a particular example, the opposing lateral sides are contoured or shaped to contact or encompass a user's face when the mask is in use on the user.

Inferior mask frame portion 74 may also be contoured or shaped to contact or encompass a portion of a user's face when the mask is in use on the user. Inferior mask frame portion may be configured to allow a user to open his mouth while the mask is in position on the user and while keeping the superior mask portion in position (e.g., the inferior mask frame portion may accommodate movement of the jaw of the user without moving the superior mask portion out of position). In some embodiments, an inferior mask frame portion may provide additional space near the user's chin to allow movement.

Inferior mask frame portion 74 is inferior to the superior mask portion and forms frame 82 around the bottom and lateral sides of the opening. Although the opening is shown as a generally rectangular shape in these figures, the opening can be any shape as long as it allows access to an area larger than the mouth, so that it can be a circular, an elliptical, a hexagonal, an oval, a rounded rectangular, a rounded square, a square or another shape, and the frame can be any corresponding shape to encompass bottom and lateral portions of the opening. An opening may be generally symmetrical about the midline of the face mask (e.g., in a generally central location), but could instead be off-center or irregularly shaped. The opening may be in any location inferior to the superior mask portion.

An opening in a face mask may be any size that can accommodate a surgical, diagnostic, or other device or a caregiver's hands. In some embodiments, an opening is larger than a user's mouth (e.g., a user's open mouth). In some other embodiments, an opening is larger than an endoscope. In some other embodiments, an opening is larger than an echocardiogram probe. There may be different sizes of face masks or different size openings for different users. A face mask may be sized to fit a face of an infant, a child, or an adult and an opening may be sized accordingly. A face mask or its associated opening may be sized to accommodate a particularly large person or an obese person. An opening may be larger than a user's mouth. An opening may be larger than a user's open mouth when a scope or other device is inserted into the user's mouth (or nose). An opening may be larger than a scope or other device when a scope or other device is inserted into the user's mouth or nose. An opening may be sized to not contact a scope when a scope is in place in a user's mouth (or nose). An opening may be sufficiently large to allow a surgical or diagnostic procedure to be performed on part of a user's face. An opening may be sufficiently large to allow a physician's hands or other caregiver hand's to manipulate a scope or other devices into a user's mouth. An opening may be larger than about 4 cm$^2$, larger than about 5 cm$^2$, or larger than about 6 cm$^2$. An opening may be smaller than about 6 cm$^2$. An opening that is in the shape of a circle (or a square) may have a diameter (or a side) larger than 2 cm, larger than about 3 cm, larger than about 4 cm, larger than about 5 cm, or larger than about 6 cm. A diameter of a circle or a side of a square may be smaller than about 6 cm.

Another aspect of the disclosure provides method of using a face mask, the face mask comprising a superior mask portion having two opposing lateral sides and a bottom side, wherein the superior mask portion is adapted to cover the user's nose and the bottom side is adapted to be superior to the user's mouth when the face mask is in position on the user, and an inferior mask frame portion connected with the superior mask portion, comprising a mask frame around a generally central open portion, wherein the generally central open portion is adapted to be over the user's mouth when the face mask is in use on the user and has an initial size and an initial shape, the method including the steps of positioning the face mask on a user, and inserting a device through the generally central open portion while maintaining the initial size and the initial shape of the generally central open portion.

A mask with a generally central opening may be made of any biocompatible material (or materials) suitable for placing on a user. Superior mask portion and inferior mask frame portion of the face mask may be made of the same materials or may be made of different materials.

An inferior mask frame portion contacting a generally central opening may be configured to hold a shape (e.g., to remain open or hold an initial shape). It may be configured to maintain a size (e.g., to hold an initial size). It may be configured to hold a shape or hold a size in the absence of any applied force (such as an applied opposing force from a scope or other device). An inferior frame portion contacting a generally central opening may be inflexible, non-compliant, rigid, or stiff. FIG. 10 shows a face mask with rim 83 around generally central opening 86. A rim may go all the way around or partway around a generally central opening. In some embodiments, a rim may be inflexible, non-compliant, resilient, rigid, or stiff. In some embodiments, a rim may be compliant or flexible and may be configured to form a seal with a face of a user (e.g., be a gasket).

Having an opening in a face mask may allow a face mask, or part of a face mask (e.g., an inferior mask frame portion), to bend, pull up (e.g., pull superiorly), twist or otherwise move, especially in response to handling or face movement. Portions of the inferior mask frame portion may include a material with a stiffness greater than a stiffness of a portion of the superior mask portion. In particular, the inferior mask frame portion (or a portion thereof) may include a reinforced material that is a reinforced version of a material used elsewhere in the face mask, such as in the superior mask portion. A reinforced material may be reinforced in any way and using any material that produces a stronger or more resilient material that is safe for use on a user, such as using a thicker material or including a fabric or a plurality of fibers, particles, or threads. A reinforcement material may be, for example, a cloth, metal, or a polymer. A stiff material may extend to the generally central opening, and may generally surround the opening. A stiff material may extend throughout the inferior mask frame portion.

A face mask may have other features to help hold the face mask in place on a user. FIG. 9 shows strap(s) 26 coupled with first lateral side 76 and second lateral side 78 and configured to wrap behind a user's head and hold a face mask in place when in use on user 85. A face mask may have one or more straps. Two straps may meet and join, or two or more straps may be generally parallel or crisscross. A face mask to hold a face mask to a user's face may have an adhesive material partway or all around an outside edge of a face mask or may have an adhesive material partway or all around the opening or around another part of the face mask. An adhesive material may removably attach a part of a face mask to a user's face. In a particular example, an adhesive material on a face mask is configured to removably attach an outer portion of the mask to a user. A face mask may include a material (e.g., a foam; shape-memory foam) that can conform to the user's face and may help hold the mask in place, or otherwise provide support or comfort. FIGS. 9, 10, and 12 show shapeable bridge 88 configured to conform to a portion of a user's face and help hold a face mask in place.

A face mask with a generally central opening may have none, one, two, or more than two sampling ports or ports. FIGS. 9 and 12 show a face mask with left lateral sampling port 12 and right lateral sampling port 14 on opposing sides of a midline. A port may be located anywhere on the mask and may have any of the characteristic(s) as described elsewhere in the disclosure.

A face mask with a generally central opening may have a gas port extending through the face mask. FIGS. 9, 10, and 12 show gas port 90 in the superior mask portion. FIGS. 11A-B show different views of a gas port and elbow. A gas port may have an internal end in a mask reservoir and may be partially, totally, or not at all directly above the nares when in place on a user. A gas port may be superior to, inferior to, or at the same level as the nares when the face mask is in place on a user. FIGS. 9-12 show different views of gas port 90 configured to receive a gas (e.g., oxygen) and to deliver the gas (oxygen) through or to a face mask. Oxygen is delivered through an oxygen conduit, through tubing 92, through elbow connector 94, elbow 96, channel 98, and through gas port 90. Elbow 96 is formed of a material stiffer than another portion of the gas conduit (such as tubing). An elbow may be made of a sufficiently stiff material to be held a bent position while in use. An elbow may be sufficiently stiff to not change its shape during use, or it may be configured to be bent from a first shape into a second shape and maintain the bent configuration while in use. In some embodiments, an elbow may define an angle between about 80 degrees and about 180 degrees, between about 90 and 180 degrees, or between about 90 and 135 degrees. In some particular embodiments, an elbow may define an angle of about 90 degrees. In some embodiments, all or part of a stiff ("elbow") portion may be located within about 2 inches, within about 1.5 inches, within about 1 inch, or within about 0.5 inches from the port.

Elbow 96 is further configured to move (rotate or swivel), along with another part(s) of the conduit, and may be configured to move while the face mask is in place on a user and when the elbow connected with the face mask. Elbow 96 may be rotated in order to move tubing 92. As indicated by arrow 100, an elbow (and part of the conduit) may rotate (swivel) any amount. In some embodiments, an elbow may rotate up to (and including) 90 degrees, up to (and including) 180 degrees, or up to (and including) 360 degrees. Elbow and tubing may be moved for any reason, such as to prevent them from interfering with a procedure that is performed through the opening or a procedure being performed close to the mask, or to increase the comfort of the user, to increase the convenience of a caregiver, or for any another reason.

One aspect of the disclosure is a face mask to deliver oxygen to a user, including a superior mask portion having two opposing lateral sides and a bottom side, wherein the superior mask portion is adapted to cover the user's nose and the bottom side is adapted to be superior to the user's mouth when the face mask is in position on the user, and an inferior mask portion connected with the superior mask portion and surrounding a generally central membrane wherein the membrane is adapted to be over the user's mouth when the face mask is in use on the user, and an oxygen port for delivering oxygen to the user. A generally central membrane may be configured to allow a device (e.g., a scope) or fingers to move from outside a face mask to inside a face mask (e.g., it may have a perforation). In some embodiments, it may be configured to form a seal with a device or scope to thereby reduce or prevent a gas from moving from inside to outside a face mask. In some embodiments, a membrane may be removable from a face mask. In a method of using a membrane, a membrane may be placed around an object, at least a portion of an object placed through an opening in a face mask, and a membrane may be connected with the face mask.

Another aspect of the disclosure includes a face mask to deliver oxygen to a user, the face mask including a connector for connecting a gas conduit with a port on the face mask, wherein the connector is configured to move with at least two degrees of freedom relative to a point on the port. The face mask may be connected to an anesthesia machine, a nebulizer, or may be further configured to deliver other agents, including, but not limited to an aerosol, an anesthesia agent, or a nebulized agent to the user. A face mask with a connector configured to move with at least two degrees of freedom may be used for any purpose, but may be especially useful for performing a surgical or diagnostic procedure on an upper portion of a user, in particular superior to the T5 dermatome of the user. The face mask may include additional features that are useful in performing such a surgical or diagnostic procedure.

FIGS. 13 A-C and 14A-C show embodiments of face masks and movable gas inlets, including reservoir 125 and joint 122 in different configurations. The joint includes first mating piece 124 and second mating piece 126 which are configured to mate with one another, such as in a ball-in-socket mechanism. The first mating piece, or connector, is configured to move with at least two degrees of freedom. The first mating piece, or connector, may be configured to move with at least two degrees of freedom relative to a point 129 on gas port 123. It may connect with the second mating piece and with a gas conduit. Gas conduit includes joining member 128 and tubing 130. A joining member or tubing may be configured to move with at least two degrees of freedom. In some embodiments, a joining member or tubing may be configured to move with at least two degrees of freedom relative to a point on the gas port. In some embodiments, gas port 123 is continuous with reservoir 125 so that a gas may be moved through the port and into the reservoir. A joining member may include a region of stiffness that is stiffer than another portion of the gas conduit. A joining member may hold a tubing in a position. A joining member may include an elbow as described above. An elbow may be formed of a material stiffer than another portion of the gas conduit, such as tubing. An elbow may be made of a sufficiently stiff material to hold a bent shape while in use. It may be sufficiently stiff to not change its shape during use, or it may sufficiently flexible or resilient be able to be changed into a shape, and then maintain that shape while in use. In some embodiments, it may be in or made into an elbow defining an angle between about 80 degrees and about 150 degrees. In some particular embodiments, it may be at or made into an elbow defining an angle of about 90 degrees. In some embodiments, all or part of a stiff ("elbow") portion may be within about 2 inches, within about 1.5 inches, within about 1 inch, or within about 0.5 inches from the port.

A connector (and tubing) configured to move with multiple degrees of freedom allows the connector and tubing to be conveniently moved out of the way of a surgical procedure or moved to a more convenient location or moved to a more accessible location. A face mask with a movable connector or gas conduit may be useful for any type of surgery, but may be especially useful for surgery in a superior part of a body, especially above the level of the fifth thoracic dermatome (e.g., approximately the nipple line), in which the position of the patient or the location of a procedure on the body may interfere with connection or the location of the gas (oxygen) conduit, or may create safety concerns. A movable connector allows the gas conduit to be moved out of the way body habitus of a patient such as a prone or obese patient. A connector may be moved to a position without conduit attached to it, or a connector and tubing may be moved together. In some embodiments, a connector or tubing may be configured to move with one, two, three, four, five, or six degrees of freedom. A connector or tubing may be configured to rotate with one, two, or three degrees of freedom (see FIG. 13D). A first or second mating piece (or both pieces) may be shaped (e.g., such as being oval shaped) so as to limit the degrees of freedom. The first mating piece may have or may be acted upon by a hold mechanism in order to prevent (further) movement, such as after being placed in a preferred location. A hold mechanism may be any mechanism that prevents or reduces movement, such as a tab that locks the first mating piece in place or a clip that holds the gas conduit in position. In another embodiment, a first mating piece may move relative to a point on a gas port independent of any rotational movement. In some other embodiments, a first mating piece may be positioned close to, but not in line with an edge of a face mask. It may be connected with the port through a short conduit (e.g., tubing or pipe).

Figure 13A:
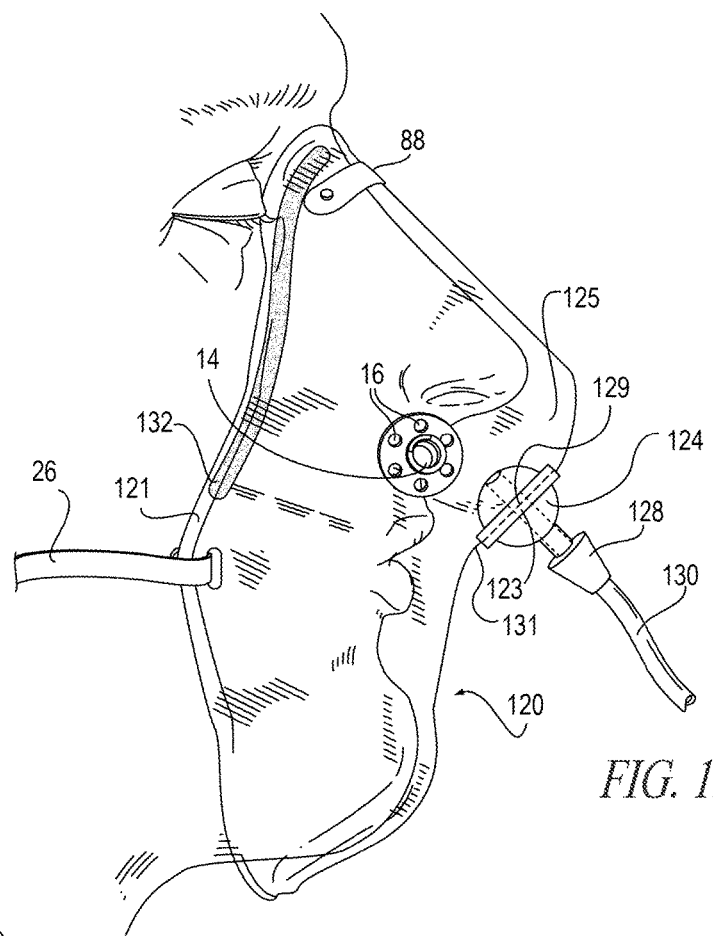
FIG. 13A shows an embodiment of a face mask with a connector for moving a gas conduit.

A face mask, joint, and conduit may be joined or formed together in any way. In one embodiment, a connector (first mating piece) may be connected with a second mating piece on a face mask (e.g., forming a joint) and then a conduit attached with the connector (first mating piece). In another embodiment, a conduit may be connected with a connector (first mating piece), and then the connector (first mating piece) attached with a second mating piece on face mask to form a joint. In another embodiment, a first mating piece may first be connected with a second mating piece and with a gas conduit, and then connected with a port on a face mask. As can be seen from FIGS. 13 A, B, and C first mating piece 124 has channel 127 to allow a gas to pass therethrough, such as from a conduit to a face mask and into reservoir 125. Different orientations of the reservoir and joint are shown in FIG. 13A and FIGS. 14A-C. As shown in FIG. 13A, the second mating piece attaches to an inferior surface of the mask at reservoir 125. An inferior surface of the mask defines an angle with a transverse plane of a user. In can be seen from FIG. 13A and FIG. 13C, the inferior surface and a transverse plane of a user when the mask is in place on a user form an angle. An inferior surface may define an angle from 0 degrees to about 90 degrees (e.g., an acute angle) relative to a frontal plan of a user when a mask is on a user.

Figure 13B:
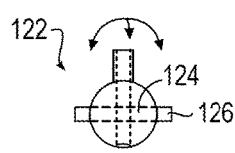
FIGS. 13B-C show a connector such as the one shown in FIG. 13.
Figure 13C:
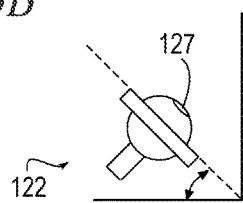
Figure 13D:
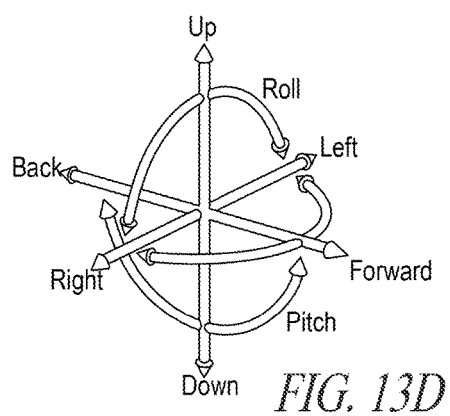
FIG. 13D shows the degrees of freedom that a connector may have.
Figure 14A:
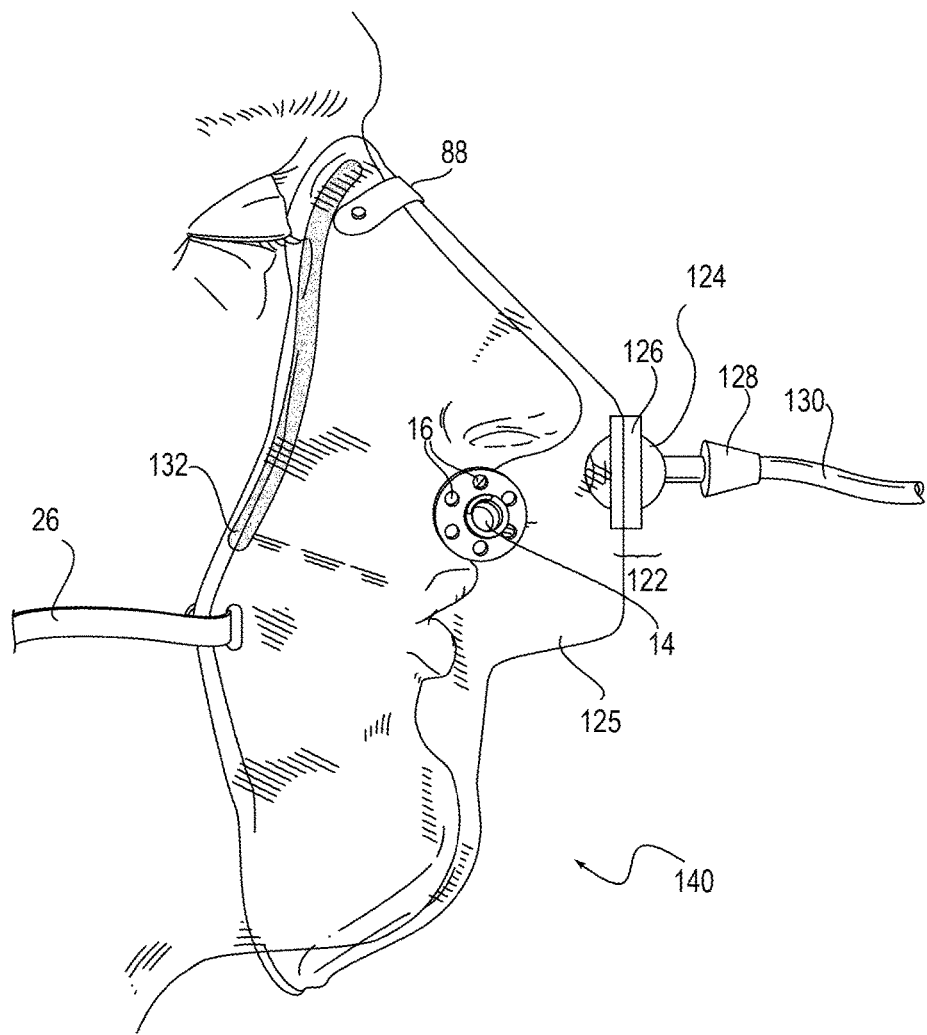
FIGS. 14A-C shows other embodiments of face masks and connectors for moving gas conduits.
Figure 14B:
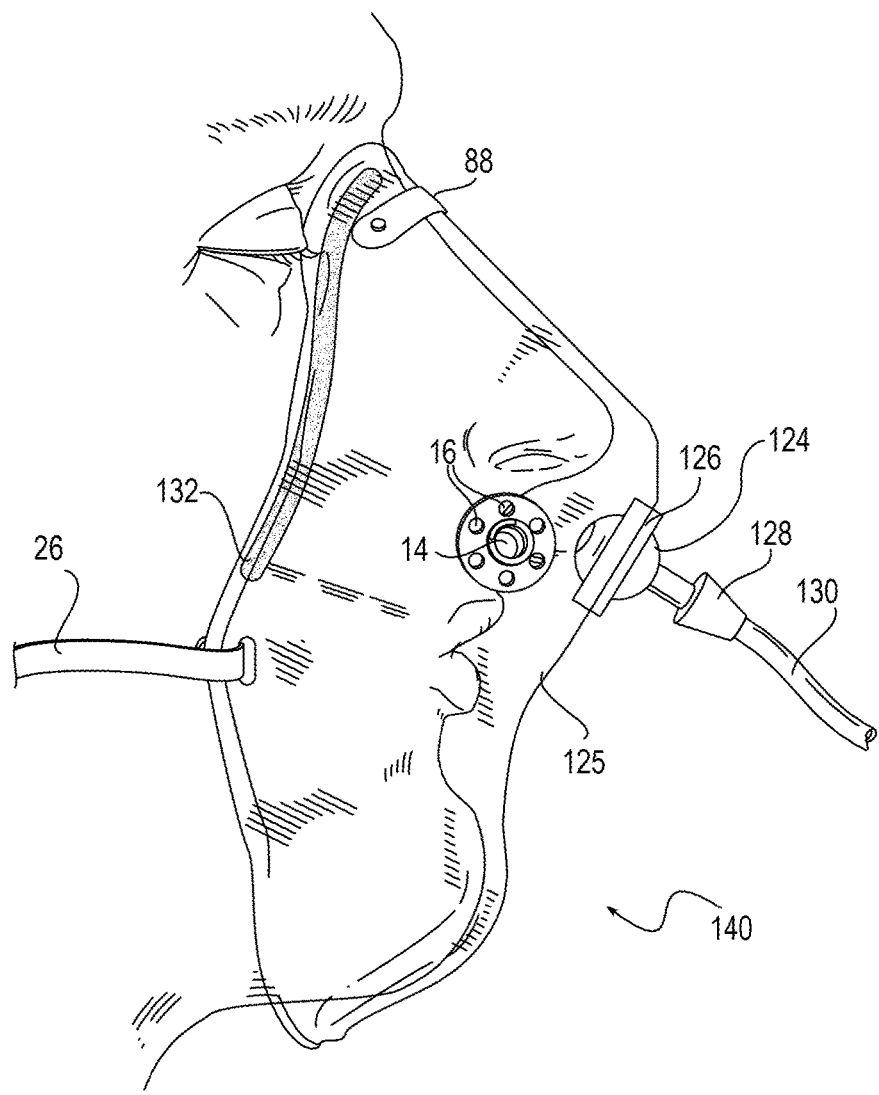
Figure 14C:
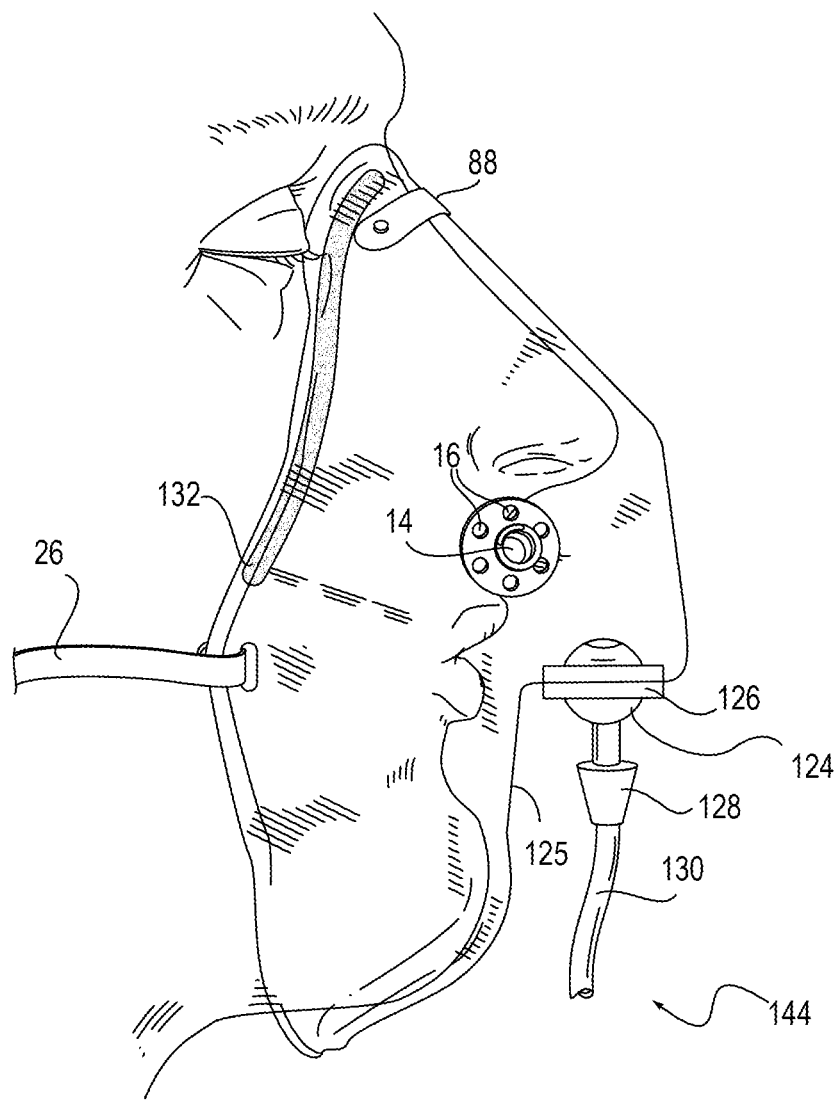

The first and second mating pieces may fit together in any way that allows movement with at least two degrees of freedom. A first mating piece 124 may have a rounded portion (e.g., a ball or ball-shaped end) that articulates with a collar-shaped second mating piece 126, as shown in FIGS. 13B, C. A second mating piece, such as a collar, may be in any position that allows gas flow and ease of face mask use. A second mating piece may define an angle from about 0 degree angle to about a 90 degree angle relative to a transverse plan of a user when the mask is on the user, as shown in FIGS. 14A-C. In one particular example, the second mating piece defines about a 45 degree angle with a transverse plane of a user when the mask is on the user.

A face mask with a movable connector or movable gas conduit may include any of the features or characteristics described elsewhere. In some embodiments, it may be configured to cover a user's nose and at least partially cover a user's mouth. In other embodiments, it may include at least one port, at least one lateral port, at least two ports, or at least two lateral ports on opposite sides of a midline of the face mask. These may be for ventilation or sampling ports used for sampling gas.

FIGS. 13A and 14 show a removable, biocompatible adhesive material 132 along an edge of face mask 120 and face mask 140 for holding a face mask to a user's face. An adhesive material may be used in addition to, or instead of a head strap. An adhesive material may be especially useful when performing a diagnostic, surgical, or other procedure in which a head strap interferes or is otherwise difficult to use.

A face mask with a movable connector may be made with an inexpensive, comfortable, malleable, non-reactive material, such as silicone. However, a face mask may instead be made from another material(s), and these materials may be more expensive, less comfortable, less malleable, or may have other drawbacks. Use of such another material may however be beneficial, such as while performing a diagnostic, surgical or other procedure on a user above about the T5 dermatome level of the user, in order to reduce or prevent patient injury. Procedures performed with surgical or other equipment in close proximity to a source of oxygen, which is highly flammable, have a higher risk of causing a fire. Fires, started by a spark or heat from a piece of equipment igniting oxygen gas, can melt face masks on patients, causing patient injury and scarring, as well as creating dangerous situations physicians, and other caregivers. In some embodiments, a face mask may be made from a heat resistant material, flame resistant material, or fireproof material such as a heat or flame resistant or fireproof polyvinyl fluoride or polyvinyl chloride or other heat resistant material. In some embodiments Teknor APEX® 3800 or Teknor DEHP free APEX 3801 (60, 65, 70, 75, 80, 85, or 90 shore (Shore A, 15 sec) may be used.

A face mask, and in particular, a face mask with a movable connector may have additional features that may be useful while performing a surgical or other procedure or may encourage safer practices. A face mask or tubing for supplying oxygen (or another gas) may be partially or entirely a warning color, such as red, orange, or yellow, or bright yellow-green, to provide warning that a higher-than-normal risk for fire is present. A mask may further have other visual cues, such as a downwardly pointing arrow, to warn a physician(s) and other caregiver(s) to reduce the flow of oxygen to reduce risk of fire. A sign may be placed on or near a tubing for oxygen use, e.g., at the distal end of the oxygen inflow tubing near the oxygen inflow source, with a warning, such as "Use Low Flows!"

Figure 17A:
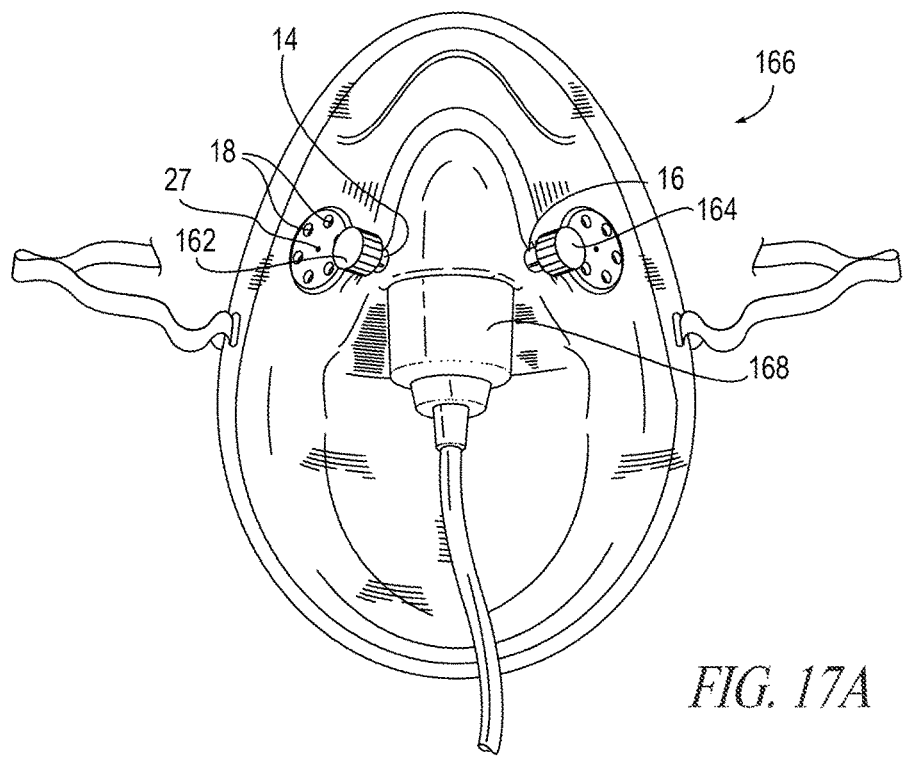
FIGS. 17A-F show face masks, systems, and methods for setting up and using a face mask and an anesthesia breathing circuit.
Figure 17B:
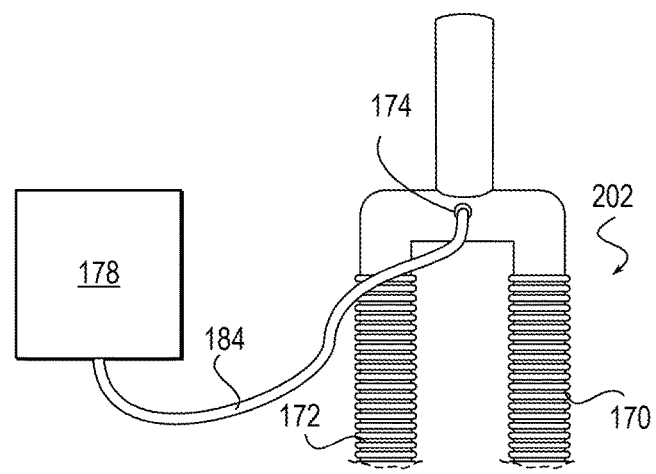

Another aspect of the disclosure includes a method of using a face mask and an anesthesia breathing circuit, the face mask including at least one port to sample an expiratory gas from a user and the anesthesia breathing circuit configured to provide an anesthetic agent and positive pressure ventilation to the user, the method including the steps of: removing a cap from a port on the face mask, removing a sampling conduit from a sensor port on the anesthesia breathing circuit to thereby expose an opening on the sensor port, coupling the cap to the sensor port to thereby close the opening on the sensor port, and coupling the sampling conduit to the port on the face mask. FIGS. 17A-B show devices, systems, and methods that may be used, for example, to provide oxygen and to provide an anesthesia agent, to remove carbon dioxide and to remove an anesthesia agent, and to monitor a gas(es) (e.g., an exhaled gas) for a user undergoing a diagnostic, exploratory, surgical or other procedure. The devices, systems and methods may, with a face mask, a gas sensor, and an anesthesia breathing circuit and methods of using the devices and systems. The devices, systems, and methods provide for monitoring a gas from an anesthesia breathing circuit or an expiratory gas.

FIG. 17B shows sensor port 174 on anesthesia breathing circuit 202 to use for assaying a breathing circuit gas. As shown in FIG. 17B, a first end of sampling conduit 184 has been connected with gas sensor 178 of an anesthesia apparatus and a second end of sampling conduit 184 has been connected with sensor port 174 on anesthesia breathing circuit 202, allowing a breathing circuit gas to flow to gas sensor 178 and be analyzed.

FIG. 17A shows face mask 166 with left cap 164 on left lateral port 16 and right cap 162 on right lateral port 14. Although both ports are shown with a cap, a face mask could have a left lateral port covered with a cap, a right lateral port covered with a cap, or both lateral ports covered with caps. If there are more than two ports, each port may have a cap. The caps are removable from the face mask. The caps may be identical to one another or may be different from one another. A cap may cover or be connected with a port in any way (e.g., they may be fitted together, screwed together, connected via a luer lock connection). A cap may be near a port, but not connected with it. For example, a cap may be placed separately from a port or separately from a face mask in a face mask kit, such as a kit shown in FIG. 6, or a removable cap may be connected (such as by a removable adhesive material) to another portion of a face mask. A cap may labeled, such as with a warning ("Close Your Circuit!"). A face mask with one or more removable caps may be placed on a user before a cap is removed.

Figure 17C:
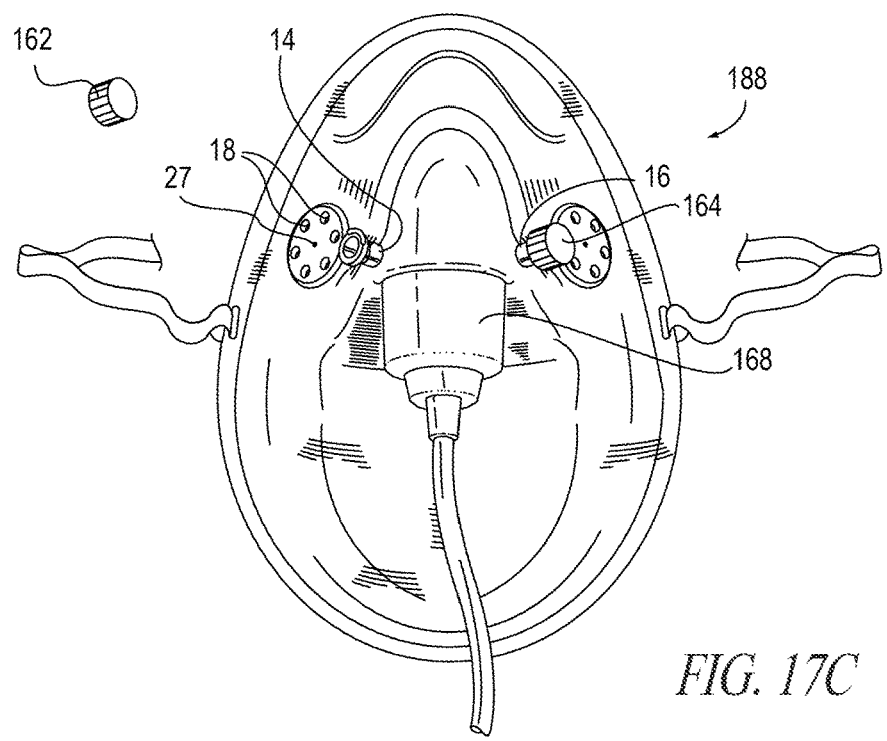
Figure 17D:
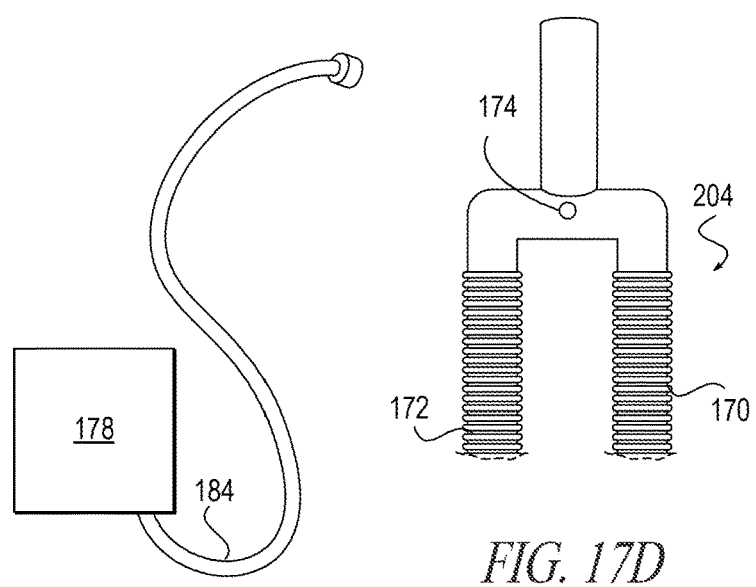

FIG. 17D shows sampling conduit 184 being removed from the anesthesia breathing circuit, exposing sensor port 174. Anesthesia breathing circuit 204 is "open" and (temporarily) unable to provide positive pressure ventilation.

FIG. 17C shows right cap 162 being removed from a right lateral port on face mask 188, exposing right lateral port 14. Left cap 164 remains in place.

Figure 17E:
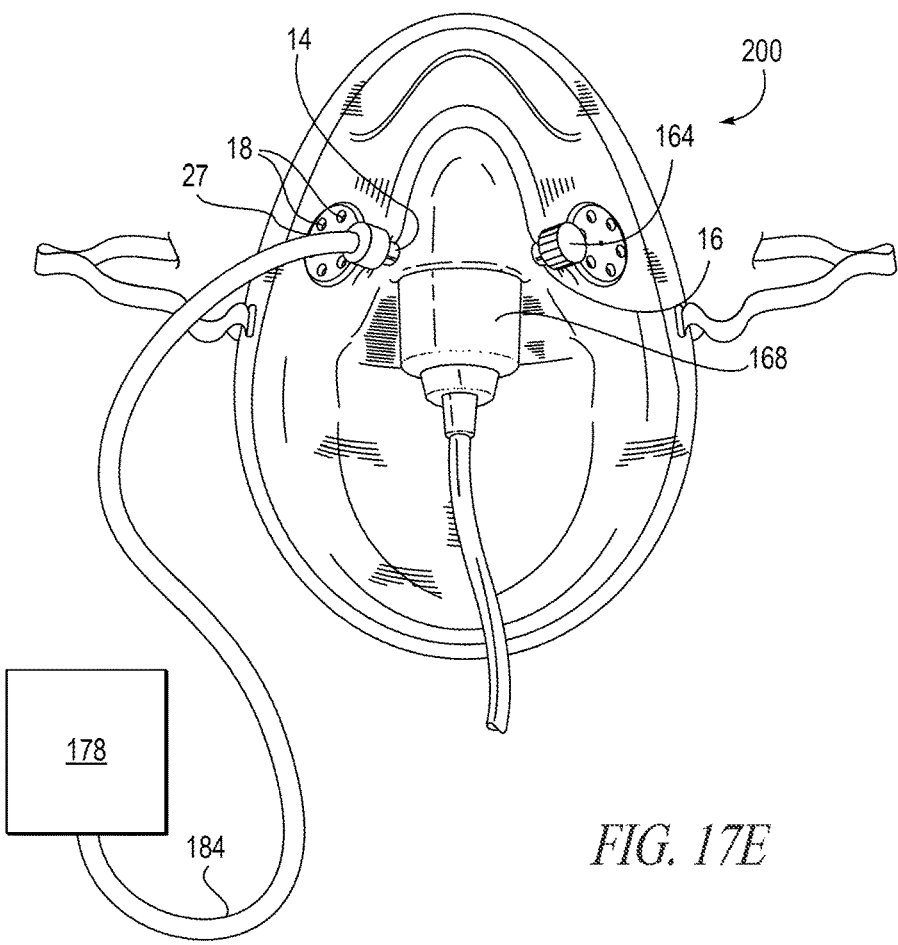
Figure 17F:
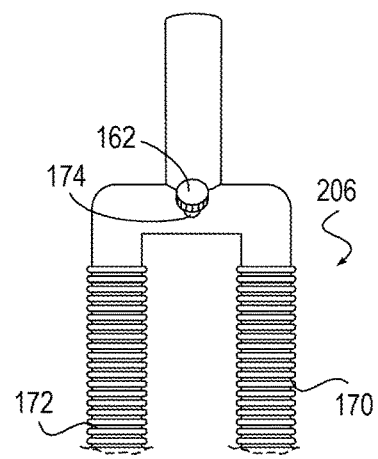

FIG. 17F shows right cap 162 coupled with anesthesia breathing circuit sensor port 174, closing the sensor port, and allowing (the now closed) anesthesia breathing circuit 206 to provide positive pressure ventilation.

FIG. 17E shows sampling conduit 184 coupled with right lateral port 14 on face mask 200, allowing gas from inside face mask 200 to flow through sampling conduit 184 to gas sensor 178, where a level of a gas may be sensed, analyzed, communicated, or displayed.

Any characteristic of a gas (e.g., a breathing circuit gas or an expiratory gas) may be analyzed by a gas sensor and a gas sensor may have any format or composition for assaying (e.g., chemical, light, other energy) as long as it can sense a gas. It may further analyze a component(s) of a gas or provide an indication of a level or amount of a gas (e.g., an audible or visual display). It may be connected with an alarm configured to provide a signal, for example if a threshold level of a gas is different from a desired amount of gas. In one example, carbon dioxide may be analyzed.

Connectors, face masks, face mask assemblies, and methods of making such face mask assemblies are described herein. Connectors for attaching to an object having an external region and a narrower port are described herein. The connectors may be especially useful for attaching to a port on an oxygen face mask for sampling an expiratory gas.

Figure 18:
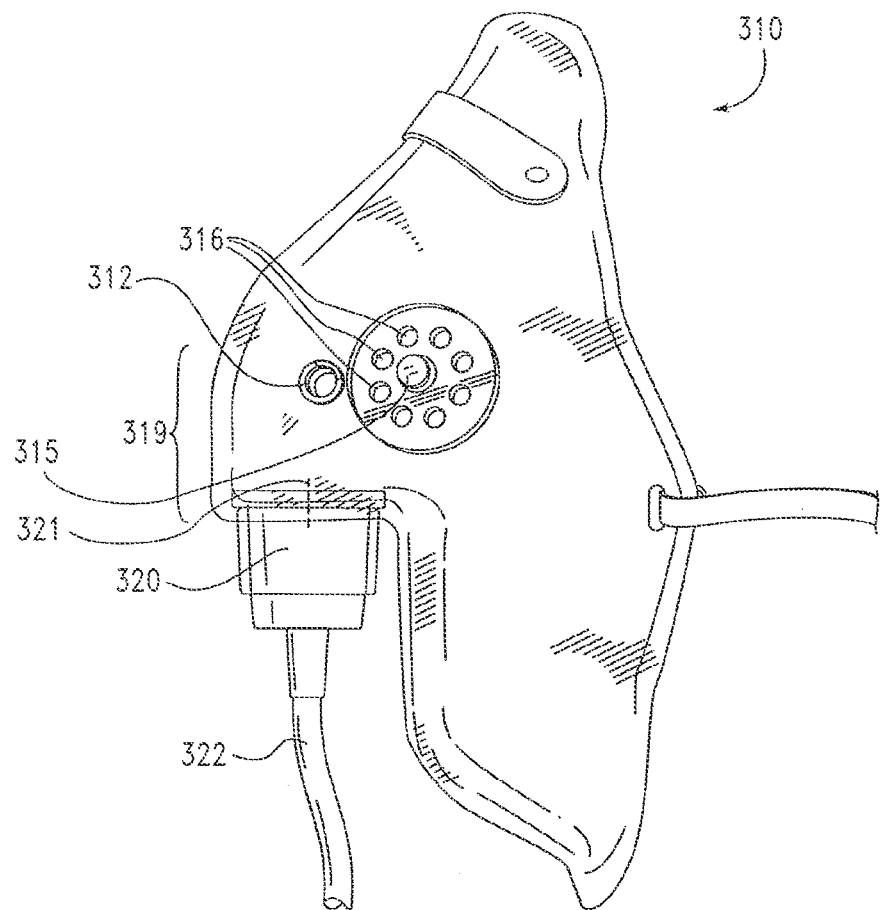
FIG. 18 shows a face mask with a lateral connector.

Another aspect of the disclosure provides a face mask assembly including a face mask and a face mask connector. The assembly is useful for delivering oxygen to a patient and sampling an expiratory gas (e.g., carbon dioxide) from the patient to determine if the patient is breathing. FIG. 18 shows face mask assembly 310, including mask connector 312. The face mask may have various additional features, such as, but not limited to, those shown in FIG. 18. By way of example, the face mask assembly may have, in addition to the mask connector, oxygen inlet port 320 with an oxygen conduit 322 for connecting to a gas source (e.g., oxygen source, not shown) and delivering the gas into the mask along an inflow pathway 321. A mask portion of a mask assembly may further have reservoir 319 for collecting or mixing gases. A mask portion may have one or more vents 316 for moving gas. The vents may allow gas inflow from outside the mask or may move gas, including expiratory gas, from inside the mask to outside the mask. The mask may have coupling point 315 to which a flexible diaphragm may be attached to control (e.g., limit, prevent, or direct) gas passage. As shown, the mask connector is on a lateral side of the face mask. The mask connector may instead be in within the vent region, more laterally, at or near the midline, lower, or higher. One or more (two, three, four or more than four) mask connectors may be on the mask. One or more mask connectors may be utilized when the mask is in use. For example, one mask connector may be used because it is in a preferred position as described elsewhere. More than one mask connector may be used to allow sampling from more than one area of the mask, such as, for example, to increase sampling accuracy or to better capture mouth and nose breathing. In one embodiment, the mask has a first port connected with a first mating connector and a second port connected with a second mask connector, the second mask connector configured to connect with a second mating connector, wherein the second port (and the second mask connector) are on an opposing side of a midline of the face mask from the first port (and first mask connector). The face mask may have any other features as known in the art or as shown or described elsewhere in this disclosure.

Figure 19:
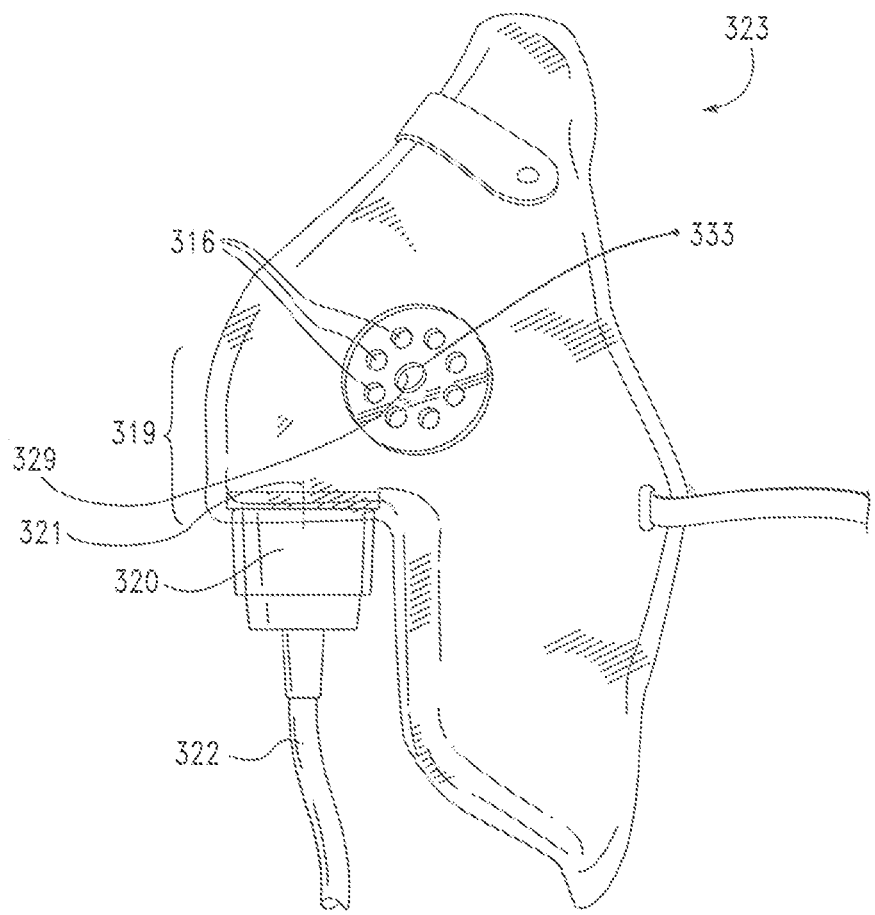
FIG. 19 shows a face mask with an oval shaped port.
Figure 20:
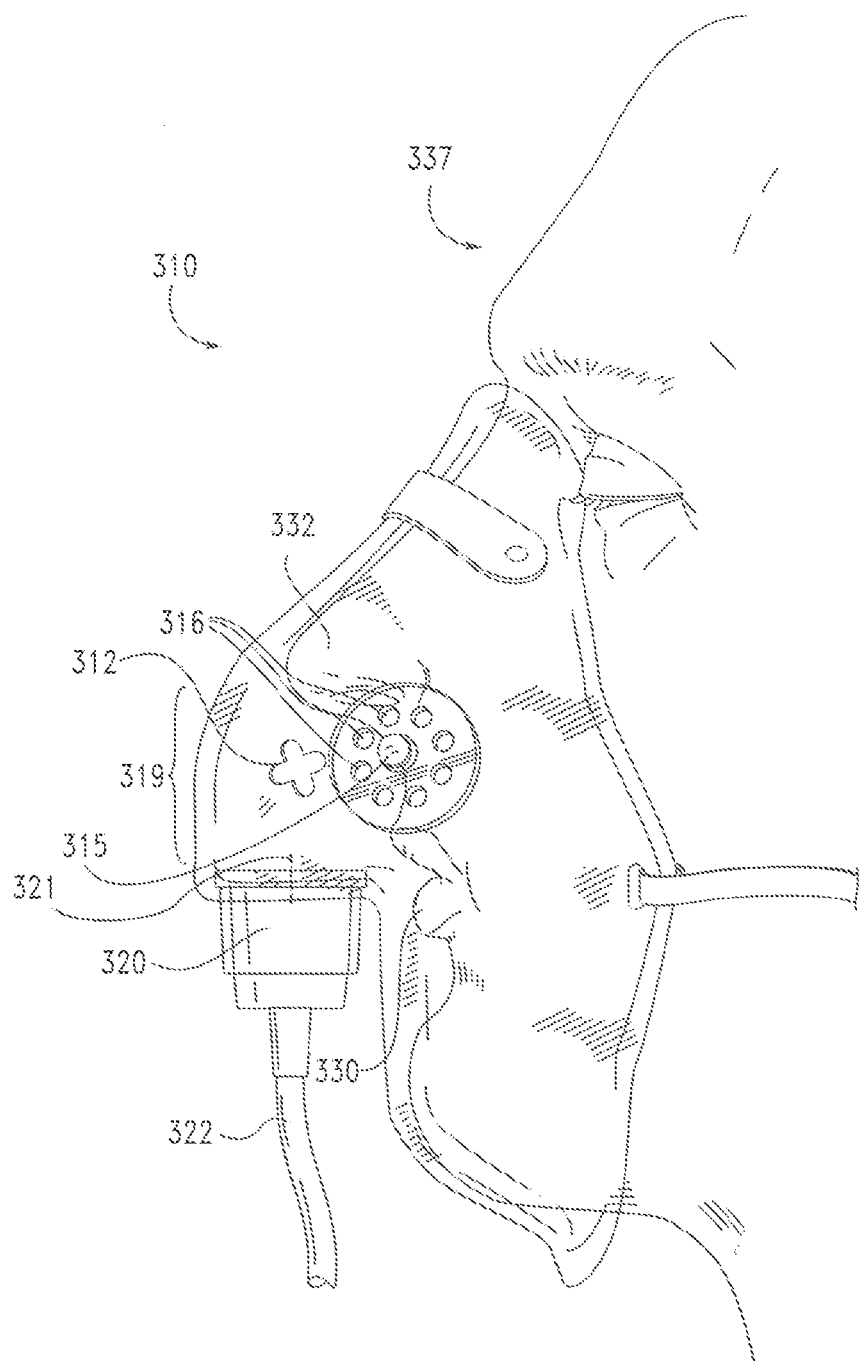
FIG. 20 shows a face mask with a "T" shaped port.

FIG. 19 shows face mask 323 with port 329 (e.g., an opening or hole) surrounded by vents 316 without a mask connector in place. Such a face mask may be made into part of a face mask assembly, face mask system, or face mask kit. Port 329 is encircled or surrounded by engagement surface 333. Engagement surface 333 may be a cutaway portion of a face mask (e.g., it may be an edge of a wall of a face mask). An engagement surface may be smoothed or may be roughed. An engagement surface may include an adhesive, a bead, a coating, a covering, a gasket or a gasket-like material. The engagement surface may aid in moving a mask connector through the port or may aid in holding a mask connector in position. FIG. 19 shows an elongated port with an elongated shaped engagement surface. FIG. 20 shows a port with a roughly cross-sectional "T" shape with a longer arm, a medium-length arm across from the longer arm and two shorter arms. A port may generally be the same size and shape from the inside opening to the outside opening of the mask. A port may instead be beveled or otherwise vary in cross-sectional profile. A port may be circular or may be non-circular (e.g., in cross-section or cross-sectional profile) . A circular (round) port may readily allow a circular connector including any known in the art to be attached to the port or moved (placed) across (through) the port. In other cases, a port may be other than round, e.g., may be non-circular or not round (e.g., in cross-section or cross-sectional profile) or otherwise asymmetrical. Having an asymmetrical or non-circular port may be advantageous and may be chosen for any reason. It may, for example, help to hold an asymmetrical or non-round connector and may therefore prevent the connector from moving or rotating relative to the face mask. This may be advantageous, for example, when a mating connector (e.g., a sampling tubing) is being attached to the mask connector. It may be difficult to grab a mask connector with a mating connector if the mask connector can move (e.g., is able to rotate). A non-rotating mating connector may manufacture or mating connector attachment easier (e.g., for example, by holding the connector immobile or lining up a marked point on the mask connector with a marked connector on a mating connector). A port may be any size that is able to provide a gas for sampling. For example, in some embodiments, a port may be from 1 mm to 30 mm. In some embodiments, a port may be from 3 mm to 10 mm in a dimension, such as a longest dimension, or a port may be from 1 mm up to and including 3 mm, from 3 mm up to an including 5 mm, from 5 mm up to and including 7 mm, from 7 mm up to and including 10 mm in a dimension, such as longest in a longest dimension.

The ports may be of same thickness as the mask wall and serve to allow passage of the end of a component, such as a gas sample line, and hold that component in place through their geometry without a connector system such as a luer. The ports may of greater or lesser thickness that the mask wall and be created at the time of the manufacturing of the mask such as during an injection molding process.

A particular shape of a port (and engagement surface) may be chosen for any reason, such as for ease of manufacturability, cost of manufacturing (e.g., cost savings), the ease with which a connector is attached, quality of gas sampling or ease of gas sampling. A port may be substantially ellipsoidally shaped (e.g., egg-shaped, ellipse, oval, racetrack, etc.), a port may by roughly circular (or another shape) with one surface feature, two surface features, three surface features, or more than three surface features (e.g., such as indents, legs or prongs). A port may be star shaped, half-moon shaped, or any other shape. A port may have none, one, two, three, four, five, or more than five axes of symmetry.

As mentioned above, according to one aspect of the disclosure, a face mask assembly may include a face mask and a mask connector. In particular, a face mask of a face mask assembly may cover a user's nose and at least partially cover a user's mouth and configured to deliver oxygen to a user, the face mask comprising a port having a non-circular cross-sectional shape, the face mask further comprising an engagement portion surrounding the port in a wall of the mask. The face mask may also have a connector configured to connect with a mating connector and having a first end, an external flange distal to the first end, a neck region distal to the external flange, and a second end distal to the neck region, and a first longitudinal channel continuous from the first end to the second end, wherein the first end is external to the mask, the external flange apposes an outer surface of the wall of the mask, and the neck region passes through the port and apposes the engagement portion.

Figure 21A:
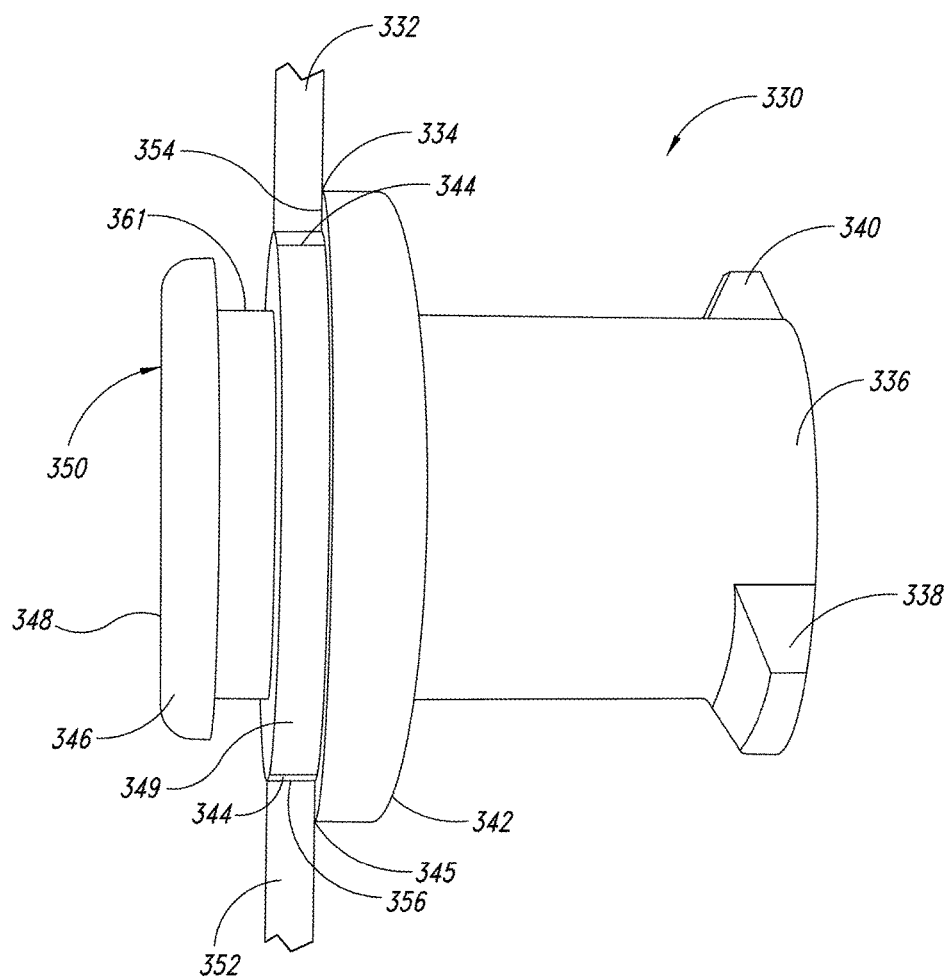
FIGS. 21A-E show various views of a mask connector with rotated flanges and anti-rotation aspect according to one aspect of the disclosure.

FIGS. 21A-D show different views of a face mask connector according to one aspect of the disclosure with a rotating or twist aspect. FIG. 21A shows a side view through a mask connector 330 in place in a face mask in a face mask assembly, such as the face mask shown in FIG. 19. The connector includes several parts (or functional regions). The inside of the mask is to the left and the outside of the mask is to the right in the figure. Part of the connector sits inside the mask, part of the connector sits within the wall of the mask, and part of the connector sits outside the mask. For illustration purposes, only a portion of the face mask (e.g., 332 and 352) is shown. Mask connector 330 has first end 336 configured to connect with a mating connector with first feature 338 and second feature 340. A feature may be, e.g., a rib useful for connecting (attaching) the mask connector to a mating connector, which may have a sampling conduit or sampling tubing connected thereto. A first end of a connector may have any feature(s) as known in the art, such as one ribs, two ribs, more than 2 ribs, one thread, more than one threads, etc. or may be configured to make a friction-fit, a slip-fit, a snap-fit, or other connection with a mating connector. A first end of a mask connector may be curved or tapered as in a luer fitting or a luer connector or may be substantially straight. In one embodiment, a first end may be a female luer end configured to fit with a male luer connector. In another embodiment, a first end may be a male luer end configured to fit with a female luer connector. A luer connector may be any size, but in some embodiments may have a maximum dimension (e.g., such as a maximum cross-sectional dimension in a longest dimension if the shape is not circular) of less than 5 mm, from 5 mm to 10 mm, from 10 mm to 15 mm, from 15 mm to 20 mm, from 20 mm to 30 mm, from 30 mm to 40 mm, or greater than 40 mm.

FIG. 21A also shows external flange 342 distal to first end 336 on mask connector 330. External flange 342 has first face 334 and second face 345, which abut or appose a portion of a first outer surface 354 and a second outer surface 356 respectively, of an external wall of a face mask. First face 334 and second face 345 of the external flange may be one continuous piece or may be discontinuous from each other. An external flange may partially cover the port, or may abut the surface radially outward from the port, or there may be a gap between an edge of the port (e.g., an engagement surface) and an edge of a face of an external flange. A face may be substantially flat in order to maximize contact between the face and the mask wall and hold the connector in place relative to the face mask. For example, a face may have adhesive, surface roughness or small grooves or other features and still be substantially flat. A portion of an otherwise flat flange face may include a feature such as a leg or a pin that grabs or penetrates the face mask wall. A leg or pin may be flat, sharpened, tapered, etc. A flange may instead be not flat, and may make a limited amount of contact with the wall surface, for example, a flange may be discontinuous relative to the wall by having legs or pins or surface indentations. The external flange may prevent inward, longitudinal movement of the connector relative to the face mask when the connector is in position. The external flange defines a footprint size against the mask portion. In one embodiment, the external flange footprint may be larger than the footprint of the port (e.g., the footprint of the engagement surface or hole).

Mask connector 330 also has an ellipsoid-shaped (outer footprint) neck region 349 which apposes (e.g., fits against) ellipsoid-shaped (footprint) engagement portion 344 of face mask 332. In some embodiments, a face mask comprises a smaller region, such as that shown as 332 and may not directly abut the inner flange. In some embodiments, a face mask thickness spans the region from the contact surface (first face) of the outer flange to the contact surface of the inner flange surface. (See FIG. 21E). The neck region fits in the port and minimizes or prevents rotational movement of the neck region (and the rest of the connector) relative to the mask. Neck region 349 may have the same shape as the port.

Although shown with the neck region, port, and internal flange having essentially the same size and having oval shapes, any size and shape may be useful and may be chosen based on, for example, manufacturing costs, ease of assembly, ease with which a mating connector may be attached, ease with which a mating connector may be removed, etc. For example, it may be easier to attach a mating connector to a connector that is fixedly held. A sampling of possibly shapes for any connector region (e.g., internal flange, neck region, external flange, first end, second end, etc.) or port is shown in FIGS. 22A-J. The neck region could be about the same size as the port (e.g., just small enough to fit inside) or it could be smaller than the port. In some other embodiments, it could also be larger than the port. In some embodiments, a neck region non-circular total cross-sectional area is within 1%, within 10%, within 20%, within 30%, within 40%, within 50%, or within 100% of an external flange total cross-sectional area. The neck region (or other parts of the mask connector) or the engagement portion of the mask could be compressible (including resiliently compressible) to enable the neck portion to fit inside the port in spite of its larger initial size. This may be advantageous, for example, in order to create a tight seal. In some embodiments, the neck region is about the same size as the port such that it fits into the port. The neck region may fit into the port in such a way as to minimize or prevent movement of the neck region (and the rest of the connector) relative to the face mask. For example, the fit between the port and the neck region may prevent rotation of the neck region (and the rest of the connector) relative to the face mask. The neck region may minimize or prevent movement (e.g., rotation) for example, because it provides a friction fit or because it provides a shape-fit. In particular, a neck region with a non-circular profile or cross-sectional area may reduce, minimize or prevent rotation of the neck region relative to the face mask.

Mask connector 330 also has a first longitudinal channel 350 continuous from first end 336 to the second end 348; the portions (e.g., first end, external flange, neck region, internal flange, second end) of the connector may each include a channel region which connect to make a continuous channel. The continuous channel allows gas to flow from inside the mask to outside the mask. A gas may be analyzed in any way, such as described elsewhere in the disclosure or as known in the art. In some embodiments, a respiratory gas (such as carbon dioxide) may be measured. In some embodiments, a force from inside the mask (such as from respiration) may make the gas flow through the continuous channel. In some embodiments, a vacuum source may be applied (such as from a vacuum source) to move air from inside to outside the mask.

Mask connector 330 is shown with spacer 361 distal to the neck region and internal flange 346 distal to the spacer and neck region. Internal flange 346 is in a rotated position relative to neck region 349 (e.g., a long axis of a cross-sectional shape of the flange is rotated or oblique relative to a long axis of a cross-sectional shape (footprint) of the neck region). The neck region and internal flange may be in a rotated position relative to one another by less than 10° (but greater than 0°), from 10° to 45°, from 45° to 90°; the degree of rotation may be based, for example, on the longest axes of each shape. Ellipsoid-shaped internal flange 346 may be placed through an ellipsoid-shaped shaped port on a face mask, and the connector rotated (e.g., twisted) to align the ellipsoid shaped neck region within the ellipsoid shaped port. The connector may be rotated by than 10° (but greater than 0°), from 10° to 45° or from 45° to 90°.

A mask connector may have none, one or both of a spacer and an internal flange. Spacer 361 has a circular footprint and is able pass through the port in various positions during face mask assembly. In some embodiments, spacer 361 could be configured in any shape (including any of the shapes described herein) and any size as long as it is able to pass through the port in at least two different positions.

Any or all of the parts (such as the external flange, neck region, internal flange) of the connector may be held in place on the mask using any means, such as adhesion (using a glue, a magnet) or may be held in place by mechanical means. In some embodiments, a port on a mask, and a neck region and the internal flange of a connector are configured (sized and shaped) such that the internal flange could pass through the port and the neck region is prevented from substantially rotating relative to the mask when in place in the port.

Figure 21B:
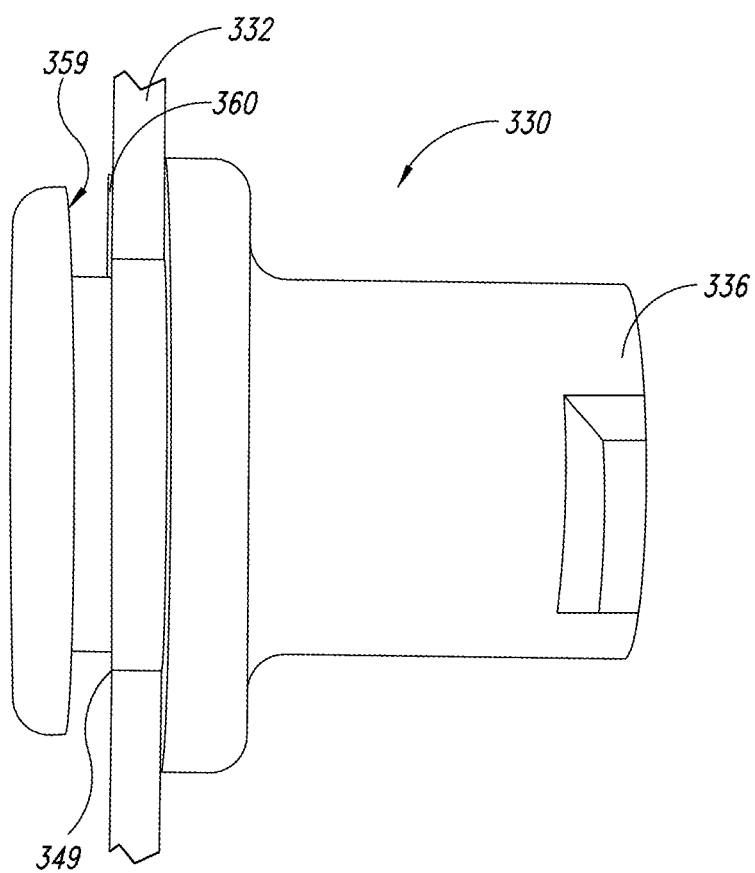
Figure 21C:
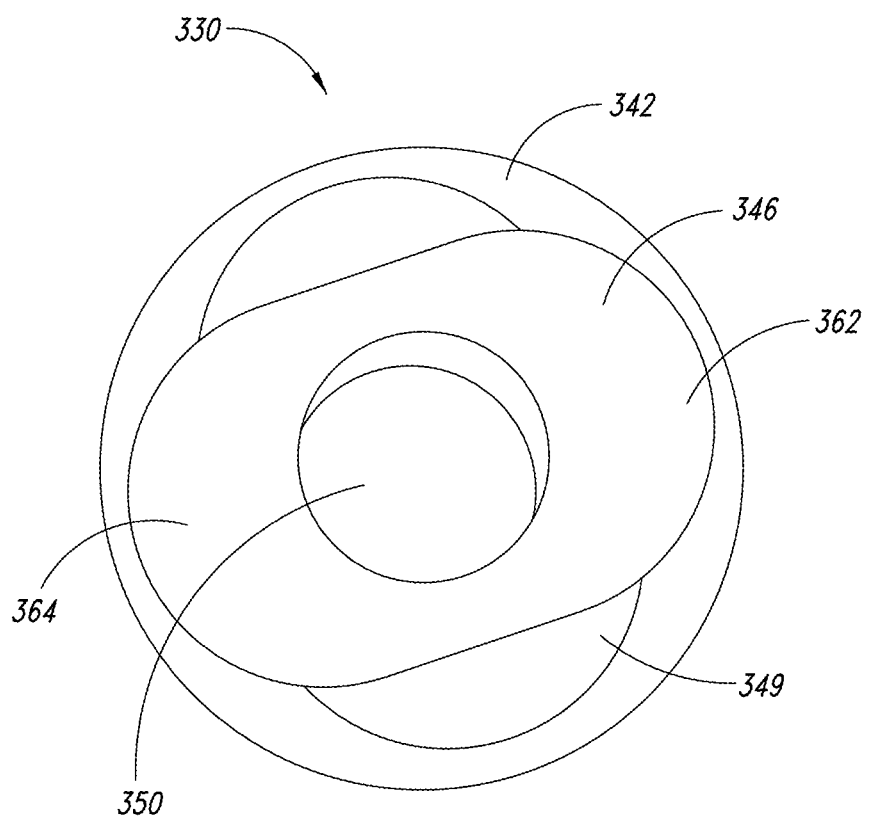

FIG. 21B shows the mask connector and face mask of FIG. 21A in a rotated view. The internal flange, which has a non-circular cross-sectional footprint, has an internal flange surface 359 that apposes an inside wall portion 360 of the mask wall and limits (minimizes or prevents) outward longitudinal movement of the connector relative to the face mask, such as through first "wing" 362 and second "wing" 364 (see FIG. 21C). In some embodiments, mask wall 332 may be relatively narrow and a small amount of outward longitudinal movement relative to the face mask may be allowed before internal flange surface 359 abuts inside wall portion 360 and prevents further movement. In some embodiments, the mask wall thickness spans from inner flange surface 359 to inner surface 344 of outer flange 342; the mask wall is flush with the opposing flange surfaces. FIG. 21E shows a view of a connector similar to that shown in FIG. 21B with a wider face mask. Mask wall 332a opposes both internal flange surface 360b and external flange first face 334. In some embodiments, an additive (such as an adhesive) connects the internal flange surface to the mask wall and prevents outward longitudinal movement of the connector relative to the face mask. FIG. 21C shows the mask connector shown in FIG. 21A (but without the mask) from inside the mask (a bottom view). The rotated position of neck region 349 relative to the position of internal flange 346 is visible.

Figure 21D:
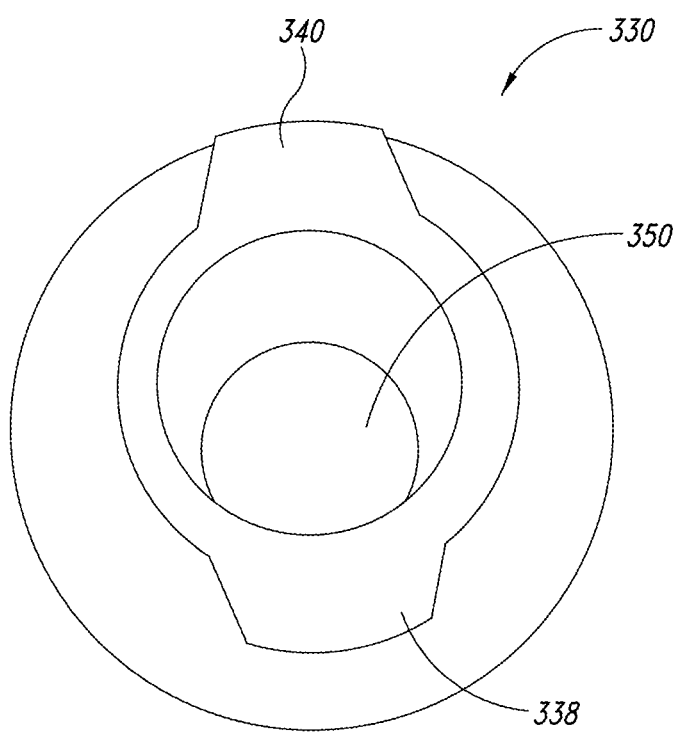
Figure 21E:
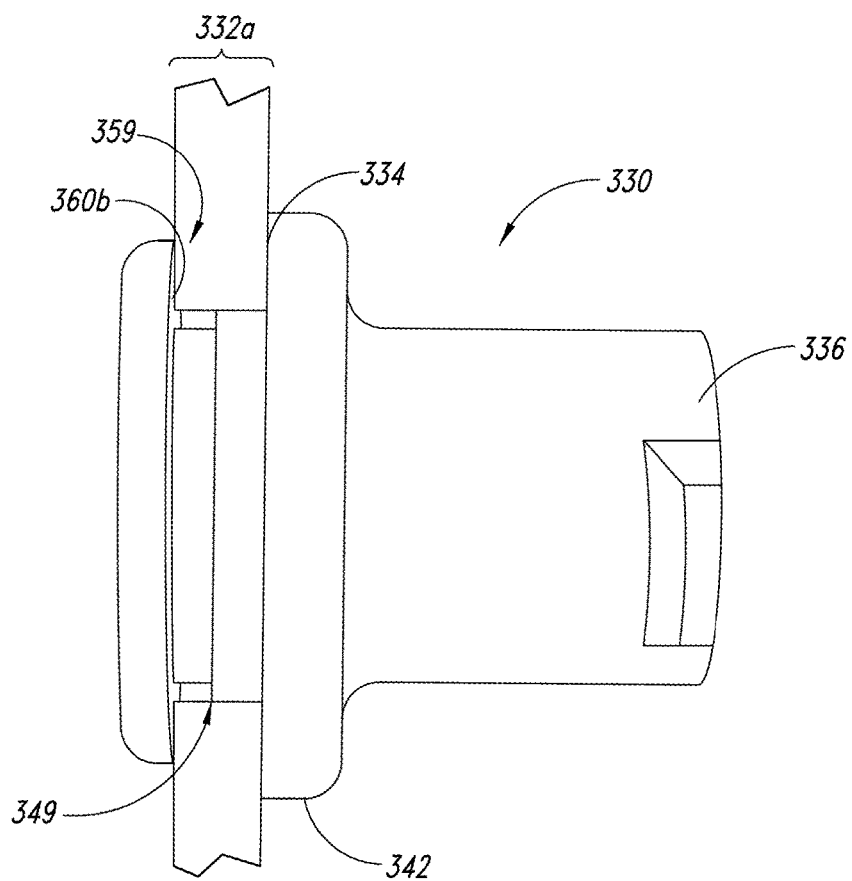
Figure 22A:
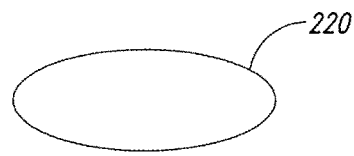
FIGS. 22A-J show various embodiments of connector and port shapes.
Figure 22B:
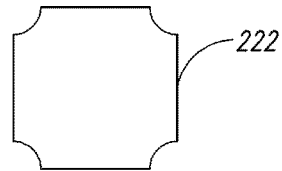
Figure 22C:
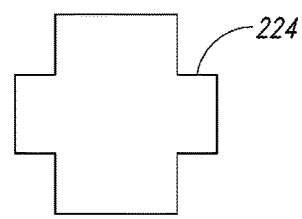
Figure 22D:
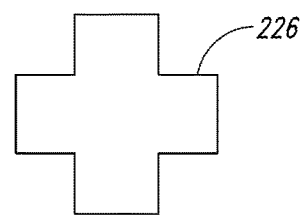
Figure 22E:
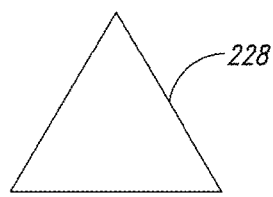
Figure 22F:
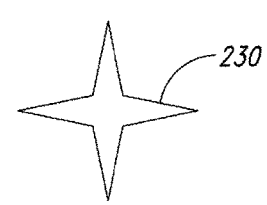
Figure 22G:
Figures 22H, 22I:
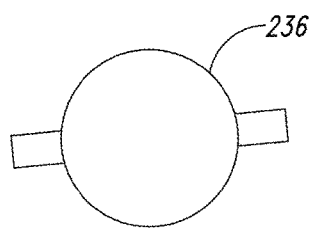
Figure 22J:
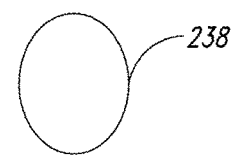

FIG. 21D shows a top view of the mask connector shown in FIGS. 21A-C, including longitudinal channel 350 for sampling a gas.

An internal (external) flange may have any of the attributes, features, shapes, etc. described elsewhere herein with regards to the external (internal) flange.

An internal flange may partially cover the port or may abut the surface radially outward from the port, or there may be a space between an edge of the port and an internal edge (e.g., the edge defining the internal channel) of a face of the internal flange. A face of an internal flange may be one continuous piece or may have discontinuities. A face may be substantially flat in order to maximize contact between the face and the mask wall and hold the connector in place relative to the face mask. For example, a face may have adhesive, surface roughness or small grooves or other features and still be substantially flat. A portion of an otherwise flat flange face may include a leg or pin that grabs or penetrates the face mask wall. A leg or pin may be flat, sharpened, tapered, etc. A flange may instead be not flat, and may make a limited amount of contact with the wall surface, for example, a flange may be discontinuous relative to the wall by having legs or pins. An internal flange may prevent outward, longitudinal movement of the connector relative to the face mask. An internal flange may minimize or prevent rotational movement of the connector relative to the face mask, such as, for example, by adhesion (e.g., an adhesive, a glue, a magnet, etc.) or by mechanical means (e.g., such as friction, pins, etc.) The internal flange defines an outer footprint (e.g., an outer perimeter or outer shape). It also has an internal channel footprint. When the internal flange outer footprint is compared with a port (e.g., a hole) and a proximal internal wall of the face mask (which it may appose or abut), the footprint may encompass (or encircle) the entire port (including being larger than the port) or may be the same size as the port. The footprint may instead only encompass or encircle only part of the port. In particular, the external mask footprint may be larger than the port (hole) in some dimensions (or axes) or areas and may be the same size or smaller than the port in other dimensions (axes) or areas.

An internal flange may generally be the same size and shape from its proximal extent (e.g., closest to the neck) to its distal extent (e.g., closest to the second end) or may be different. An internal flange may vary in cross-sectional profile and an outside (e.g., outer shape or outer footprint) may have the same or different shape as it's inside channel footprint. An internal flange outer footprint may be circular or may be non-circular or asymmetric (e.g., in cross-section or cross-sectional profile). A circular (round) flange may be easier or less expensive to manufacture, may fit with other pieces, etc. Having an asymmetrical or non-circular internal flange may be advantageous and may be chosen for any reason, such as for to make mask assembly easier.

Another aspect of the disclosure provides a method of attaching a mask connector to a face mask including the steps of: passing an internal flange of a mask connecter through a port in a wall of the face mask wherein the connector comprises a first end, an external flange distal to the first end, a neck region distal to the external flange, the internal flange distal to the neck region, a second end distal to the internal flange, and a longitudinal channel continuous from the first end to the second end and configured to provide flow of respiratory gases when the mask is in place on the user, the face mask further including an engagement portion surrounding the port and having a non-circular cross-sectional shape; rotating the connector to thereby appose the internal flange with an inside wall portion of the face mask and thereby limit outward longitudinal movement of the connector relative to the face mask; apposing the neck region to the engagement portion to thereby limit rotational movement of the connector relative to the face mask; and apposing the external flange with an outside wall portion of the face mask to thereby limit inward longitudinal movement of the connector relative to the face mask.

The method may further include the step of creating a port in the wall of the face mask, prior to the passing step. The port may be created by any means, such as cutting, injection molding, punching, etc. One port may be created or a plurality of ports may be created. In a particular embodiment, two lateral ports may be created on opposites sides of midline of the mask. A port(s) may be created in a vent center, and may be surrounded by a plurality of vents (e.g., exhalation vents). One or more ports may be created from an-off-the shelf mask; a mask may have more than two ports. The ports may or may not be substantially identical.

Figure 23A:
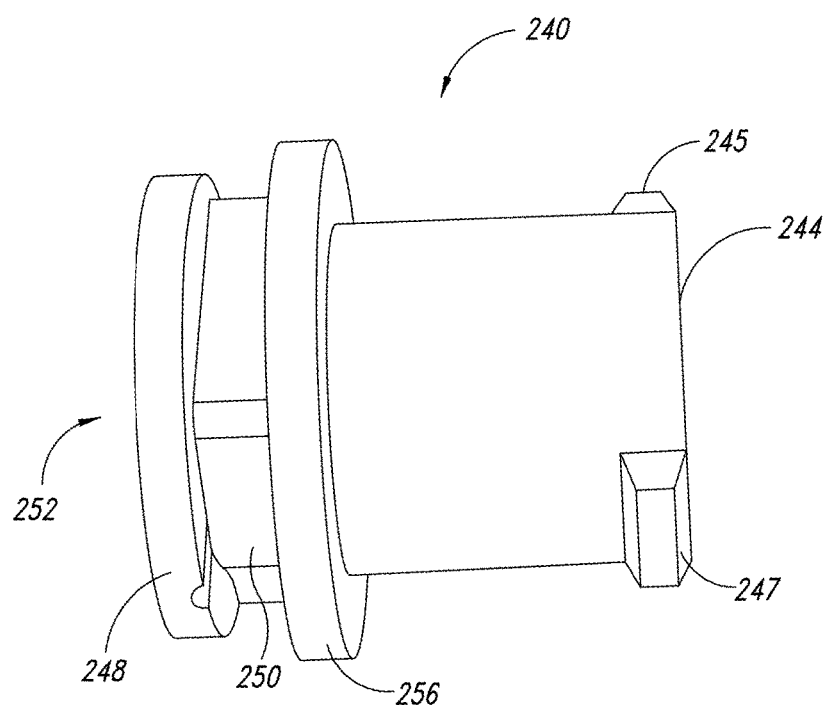
FIGS. 23A-C show another embodiment of a face mask connector with an anti-rotation aspect.
Figure 23B:
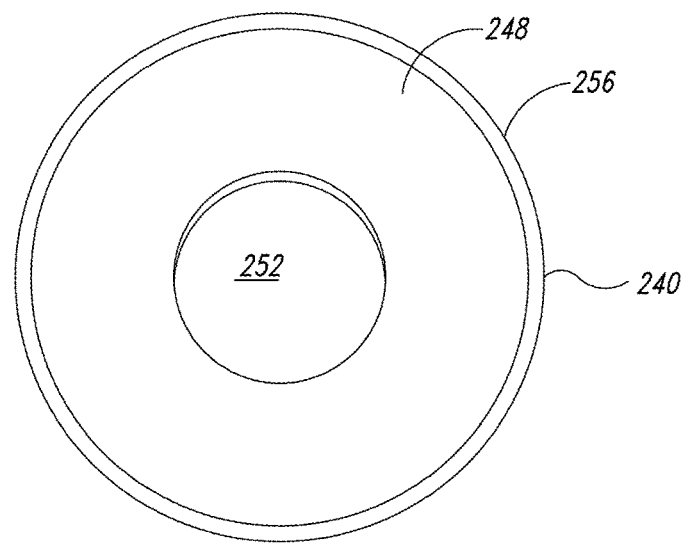
Figure 23C:
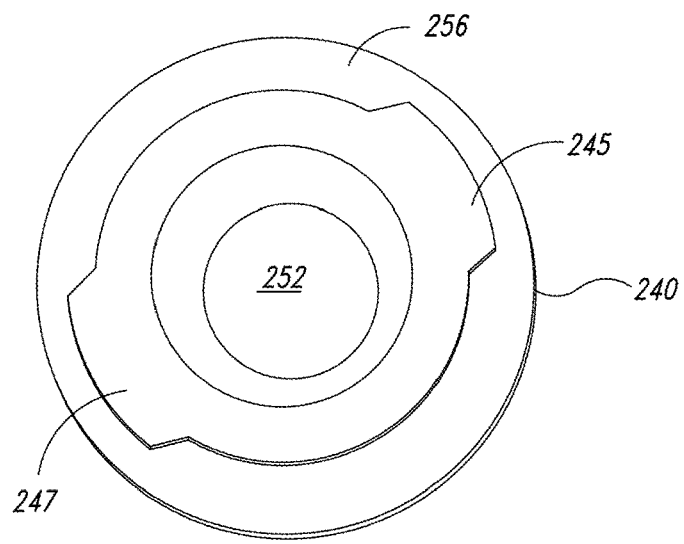

FIGS. 23A-C show another embodiment of a connector (e.g., such as a mask connector). Connector 240 includes first end 244 with first features 245 and second feature 247 that can be useful for attaching the connector to a mating connector (such as a mating luer). Internal flange 248 and external flange 256 are cylindrical and have circular cross-sectional shapes. Connector 240 can be attached to a face mask having a star-shaped port, such as by moving internal flange 248 through the star-shaped port and allowing star-shaped neck region 250 to fit into the star-shaped port and appose an engagement portion in the port on the mask. As described above, the footprint of the internal flange may be larger than the footprint of the port. At least one of the internal flange and the engagement surface of the port may be deformable (resiliently deformable) to allow the internal flange to pass through the port. Internal flange or the engagement portion or (another) part of the mask wall may have a first shape and may configured to deform to a second shape to allow the internal flange to pass through the port. An internal flange size may be the same or different from an external flange size. The internal flange, engagement portion, or another part of the mask wall may resume a first shape after deforming. When in place in the port, the neck region minimizes or prevents rotation of the connector relative to the face mask.

FIGS. 24A-D show different views of another embodiment of a mask connector which may be especially useful for attaching to a mask used for delivering inhaled medications, such as in an aerosol mask. Such a mask may have a larger port, for example, a port may a port may be from 3 mm to 30 mm in a dimension, such as a longest dimension, or a port may be from 1 mm up to and including 3 mm, from 3 mm up to an including 5 mm, from 5 mm up to and including 7 mm, from 7 mm up to and including 10 mm, from 10 mm to 20 mm, or from 20 mm to 30 mm in a dimension, such as longest in a longest dimension.

Figure 24A:
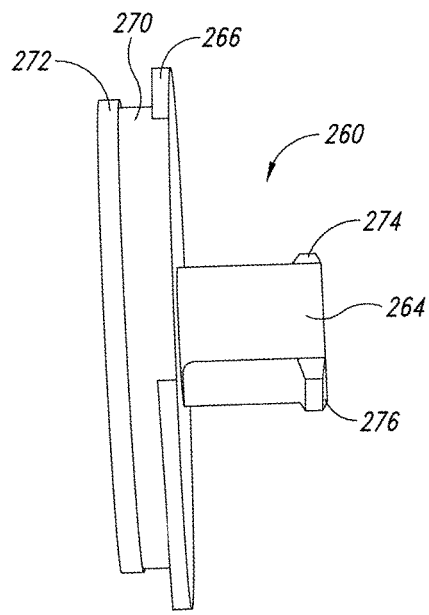
FIGS. 24A-D shows another embodiment of a face mask connector that can be used with an aerosol mask.

FIG. 24A shows mask connector 260 with first end 264 with first feature 274 and second feature 276 (as described elsewhere herein) for attaching to a mating connector. External flange 266 and internal flange 272 are racetrack shaped, and external flange 266 is in a rotated position relative to the internal flange 272. Neck region 270 is generally cylindrically shaped (e.g., with a circular footprint). Internal flange 272 can be placed through a port in a face mask, such as a similarly racetrack shaped port and neck region 270 can be apposed to an engagement surface of a port. External flange 266 can appose (e.g., abut) an external face mask wall and prevent internal longitudinal movement of the connector relative to the face mask. Internal flange 272 can appose (e.g., abut) an internal face mask wall and prevent external longitudinal movement of the connector relative to the face mask. At least one of the internal flange and the engagement surface of the port may be deformable (e.g., resiliently deformable) to allow a flange that has a larger footprint than the engagement surface to pass through the port to the inside of the mask. Another aspect of the disclosure provides a method of attaching a mask connector to a face mask comprising: passing an internal flange of a mask connecter through a port in a wall of the face mask wherein the connector comprises a first end, an external flange distal to the first end, a neck region distal to the external flange, the internal flange distal to the neck region, a second end distal to the internal flange, and a longitudinal channel continuous from the first end to the second end and configured to sample an expiratory gas when the mask is in place on the user, the face mask further comprising an engagement portion surrounding the port wherein passing comprises elastically deforming at least one of the internal flange and the engagement surface; apposing the internal flange with an inside wall portion of the face mask to thereby limit outward longitudinal movement of the connector relative to the face mask; and apposing the external flange with an outside wall portion of the face mask to thereby limit inward longitudinal movement of the connector relative to the face mask.

Figure 24B:
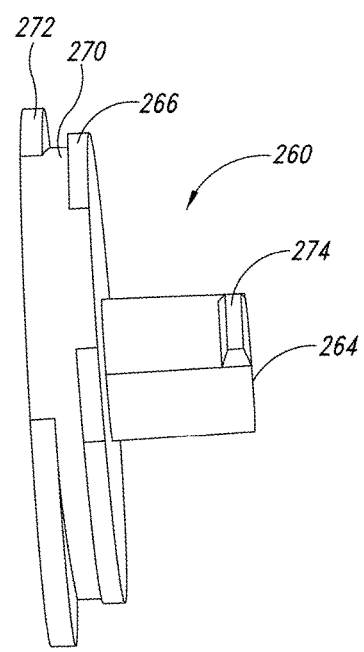
Figure 24C:
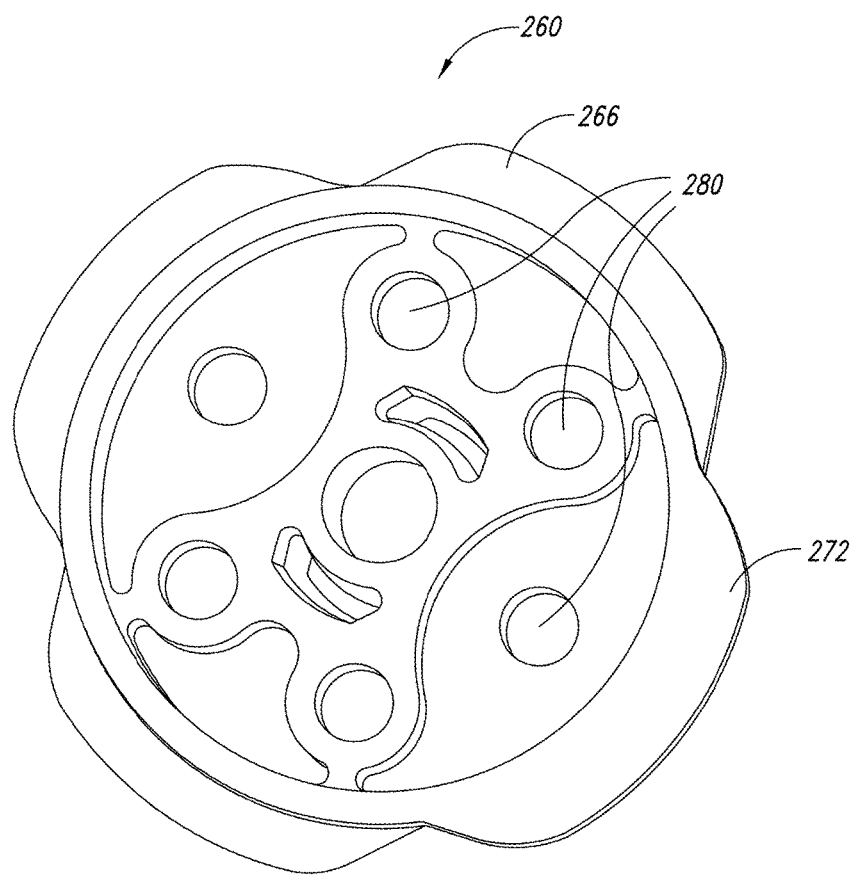
Figure 24D:
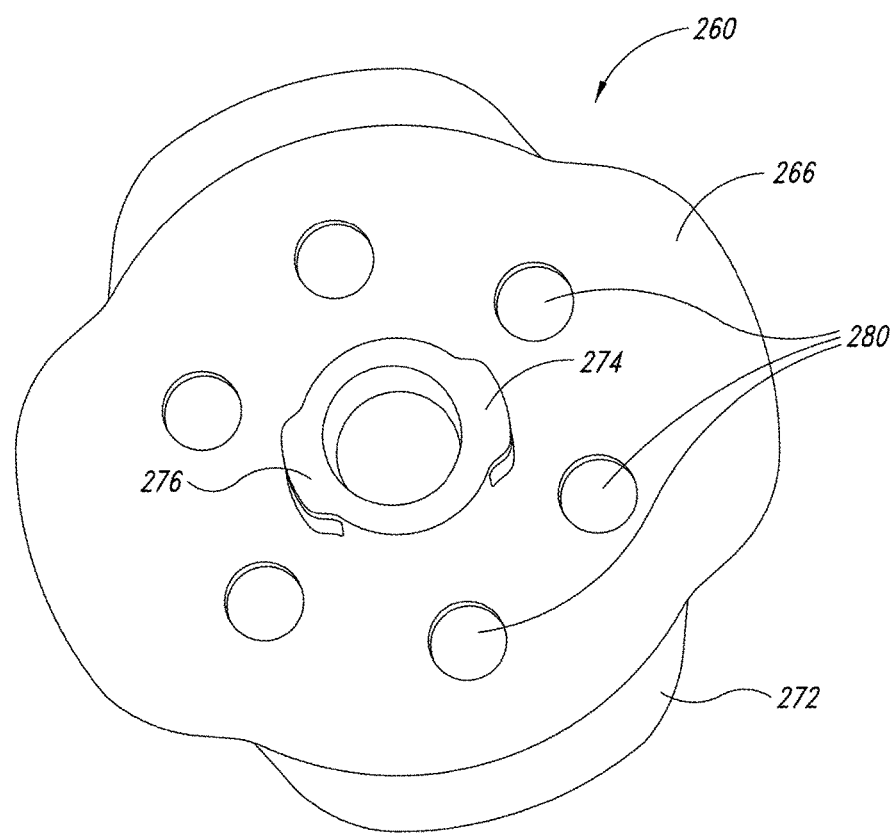

FIG. 24B shows another side view rotated relative to FIG. 24A; note that the internal flange is in a rotated position relative to the internal flange. FIG. 24C and FIG. 24C shows a bottom view and a top view, respectively, of the connector from FIG. 24A and FIG. 24B. Perforations 280 allow air to pass into (or out of) the mask.

Once a connector is in place in a mask, any part of the connector (e.g., the internal flange, the neck region, the external flange) may be held in place on the mask using adhesive means or mechanical means as described elsewhere. A mechanical hold may serve as a back-up should an adhesive not be used or if an adhesive fails during use in order to maintain the connector in the face mask.

Another aspect of the disclosure provides a first luer connector comprising: a first proximal end including a mating portion configured to mate with a second luer connector; an external flange distal to the first proximal end and configured to encircle a port and oppose a portion of an external face mask wall proximal to the port in an oxygen face mask when the first luer connector is in place on the mask and to thereby limit inward longitudinal movement of the connector relative to the face mask; a neck region distal to the external flange, the neck region having a non-circular cross-sectional shape and configured to appose an engagement surface of the port when the luer is in place on the mask and the neck region spans the port, the neck region configured to limit rotational movement of the connector relative to the face mask; an internal flange distal to the neck region wherein the internal flange is configured to oppose an internal portion of a face mask wall in proximity to the port to thereby limit outward longitudinal movement of the connector relative to the face mask; a second end distal to the internal flange; and a longitudinal channel continuous from the first end to the second end.

Some embodiments of a mask assembly further include a mating connector (e.g., a mating luer connector) having a second longitudinal channel, wherein a first luer connector and mating luer connector are connected to form a continuous longitudinal channel from the first longitudinal channel to the second longitudinal channel. Some embodiments of a face mask assembly include a sampling tubing(s). Some embodiments further include a sampling cap(s).

A mask connector may include all of the regions described above or may include only some of the regions. A mask connector may be manufactured as a single piece or as two, three, four, or more than four pieces and then assembled together.

Alternatively, a connector may be manufactured as one or more separate pieces and subsequently assembled together to create part of a connector or a whole connector. For example, a first piece may include a neck region and an internal flange and a second piece may include an external flange and a feature(s) for connecting with a mating connecter. A method of assembling a connector on a face mask may include the steps of: placing a neck region through a port; and attaching a flange to the neck region.

A face mask, assembly, kit, luer, system, or method of making or using any face mask, assembly, kit, luer, system, or method according to the disclosure may have or be combined with any one or more of the other characteristics, features, or methods described herein. Examples of the foregoing and further aspects of the present disclosure are described below in conjunction with FIGS. 25-37.

Components for the Oxygen Face Mask
Colorimetric $CO_2$ Detector

Figure 25A:
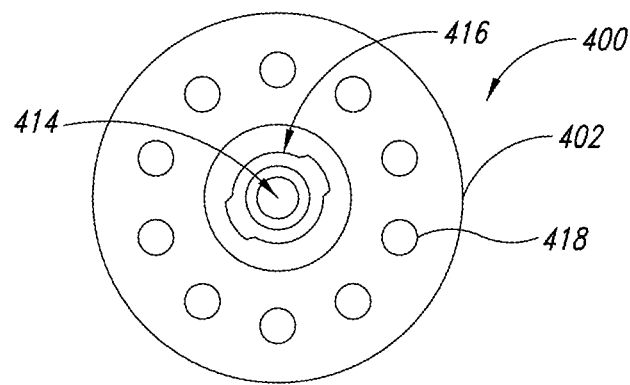
FIGS. 25A-B are top and isometric views, respectively, illustrating a colorimetric $CO_2$ detector for the face mask of the present disclosure.
Figure 25B:
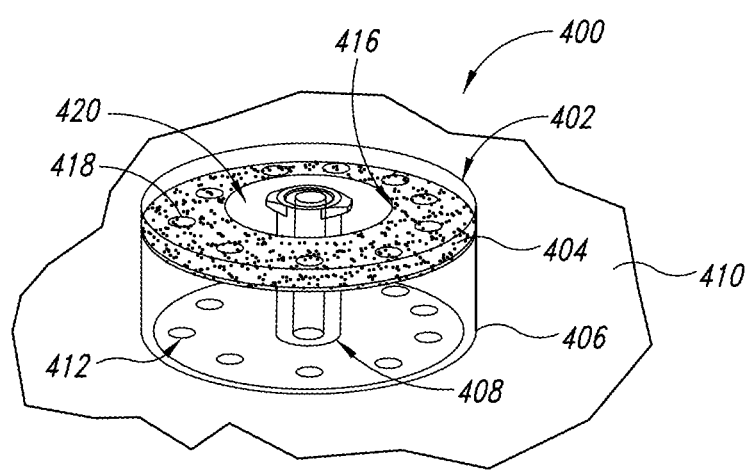

Referring first to FIGS. 25A-B, shown therein is a colorimetric $CO_2$ detector 400 configured to attach to an oxygen face mask such as described above and to detect $CO_2$ present in gas passing through a gas exhalation vent in the face mask.

$CO_2$ monitoring of patients at risk for inadequate breathing has been shown to increase safety. Patients at risk for respiratory complication who are breathing oxygen through a face mask, have periods of medical care when $CO_2$ monitoring is not readily available such as during transport and during recovery from anesthesia. $CO_2$ monitoring is not readily available for these patients because $CO_2$ monitors are not sufficiently affordable and portable and colorimetric $CO_2$ detectors are not available for oxygen face masks. Available colorimetric $CO_2$ detectors do not address safety for patients using oxygen masks who are at risk of inadequate breathing.

The detector 400 of the present disclosure is a portable and inexpensive colorimetric $CO_2$ detector that securely attaches to a patient's oxygen face mask in a position over a gas vent or port assembly as described above. The detector changes color when exposed to $CO_2$ passing through the gas vent during exhalation and provides a clear visual signal that gas exchange is occurring. The detector functions for a period of time sufficient for the patient to reach additional respiratory monitoring or resume a normal, low risk respiratory state.

The illustrated design is the first colorimetric $CO_2$ detector designed for attachment to an oxygen face mask. Currently, colorimetric $CO_2$ detectors are only available for use with invasive oxygen sources such as endotracheal tubes.

The device 400 includes a disc-shaped, hollow Colorimetric $CO_2$ housing 402 that contains a Colorimetric $CO_2$ detector-indicator 404, which may be mobile and free floating. The indicator 404 may be made of paper or other indicator material. The housing 402 is sealed with an oxygen face mask via a gas sealing barrier 406, which extends from the outer perimeter of the housing 402 to a surface 410 of the oxygen mask surrounding all or a portion of a mask gas vent 412. The device 400 is attached to the face mask by means that may include without limitation a male Luer fitting. The attachment point, in this example male Luer fitting 408, may be connected by a continuous central channel 414 to the surface of the device. In this example the superficial surface of the channel 414 is embodied by a female Luer 416. The housing 402 has multiple housing gas vents 418 on the inner and outer surfaces that allow for gas to flow freely from inside to outside the mask and vice versa. The central part of the device 400 may be composed of a gas filter 420 that filters the gas traveling through the central channel 414 of the device 400, in this case from female Luer fitting 408 to the male Luer fitting 416.

All elements of the device 400 are utilized for $CO_2$ detection of respiratory gas by a colorimetric method except for the central channel 414, female luer 416, and central channel gas filter 420. $CO_2$ analysis by capnography while utilizing the device 400 requires the presence of the central channel 414 and an outer surface connection point such as a female luer. $CO_2$ analysis by capnography while filtering respiratory gases would require the presence of the gas filter 420.

In operation, during the respiratory cycle in a patient wearing an oxygen face mask, gas flows freely through mask gas vents. During inhalation, gas flows into the mask and during exhalation, gas flows out of the mask. The device 400 attaches to the outer surface 410 of the oxygen mask and is sealed over the gas vent(s) 412. Gas flows through the device 400 during inhalation and exhalation. Inhaled gas does not contain $CO_2$ while exhaled gas does contain $CO_2$. The colorimetric $CO_2$ detector-indicator 404 within the housing 402 changes color in the presence of $CO_2$ and reverts back to another color in the absence of $CO_2$. Color change of the detector-indicator 404 may be created by a change in pH due to the presence of $CO_2$.

The device 400 thus provides visual information of rising and falling $CO_2$ levels passing through the gas vent(s) 412, which correspond to ongoing respiration and device color changes. If the color change stops, gas exchange has ceased and the health care provider can take immediate appropriate intervention. The central channel 414 allows for analysis of gas within the mask by attachment of a $CO_2$ monitor or capnograph. The capnography uses a vacuum to pull gas from inside the mask to the gas analysis unit to provide a continuous $CO_2$ reading which corresponds to rising and falling $CO_2$ levels with respiration. If filtering of the capnography gas sample is desired, our device may incorporate a central filter that filters gas flowing through the central channel.

The construction of the colorimetric device 400 can utilize plastic and other materials. The plastic components of the device include all device components except for the $CO_2$ detector-indicator 404 and the central channel filter 420. All plastic components can be created by techniques such as injection molding, which are well-known in the art and are not described in detail herein. The $CO_2$ detector-indicator 404 and the central channel filter 420 are also constructed of known materials using known technique.

The device 400 can be reconfigured in a variety of fashions while still accomplishing its key functionality. The final configuration depends on the type of attachment to a face mask, the structure and location of face mask gas vents, and the necessity of utilizing or not utilizing a capnograph and filtering respiratory gases.

Use of the device 400 is now described in a medical setting. It is to be understood that the features of the present disclosure can be applied to other face masks used outside of the medical setting. A patient who requires $CO_2$ monitoring while breathing oxygen through face mask is identified. The device 400 is removed from sterile packaging and oriented to attach to the surface 410 of the mask over the gas vent(s) 412. (The mask would be required to provide an attachment point for the device; in this example the mask would have a female luer surrounded by gas vents 412.) The provider would attach the device 400 to the mask by engaging the Luer 408 and turning in a clockwise direction until the gas sealing barrier 406 is flush with the mask surface 410 and surrounds the mask gas vent(s) 412. The provider would confirm device patency by observing gas flow through the housing 402 of the device 400. The provider would observe the color change of the detector-indicator 404, in conjunction with other clinical monitoring techniques, to ensure adequate respiration was occurring.

The device 400 is a portable and inexpensive solution to monitoring patient breathing for the presence of $CO_2$ when less mobile and more expensive monitors, such as capnographs, are not available. In the event that capnography were used in addition to the colorimetric $CO_2$ indicator, the capnograph would be attached to the device via the outer attachment point, in this example a Luer fitting 416. The capnograph would then analyze gas within the mask for the presence of $CO_2$.

The device 400 could enable automated patient monitoring based on device color changes or through the combination of color changes and capnograph readings. The device use is not limited to humans or medical use. Any conceivable application that involves $CO_2$ detection is a possible indication for use.

The lateral surface gas port assemblies or "ports" described for the devices above may serve as attachment points to removably couple a variety of other components to the mask to expand device function and form various operating systems. In some embodiments the ports do not serve for purposes of gas sampling but function solely as attachment fittings for components to be used with the face mask. Below is a description of several additional components and systems that expand the functionality of the masks described above.

Cap

Figure 26A:
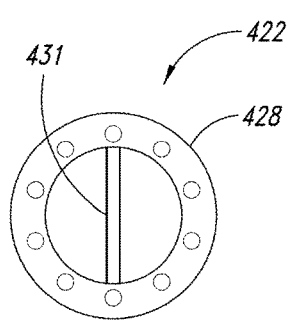
FIGS. 26A-F are top and side views, respectively, illustrating a sealing cap adapted for use with the face mask of the present disclosure and side, top, and two cross-section views of a variation of the cap of FIGS. 26A-B.
Figure 26B:
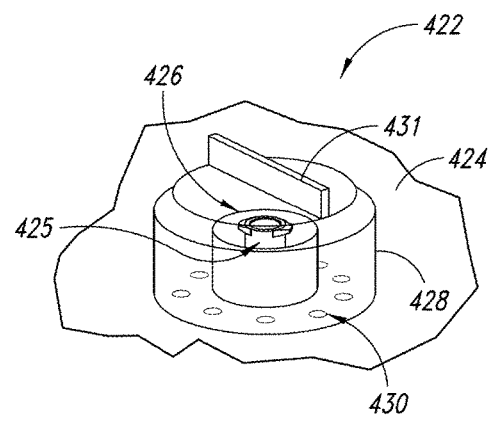

It may be determined that a gas vent or port on the oxygen mask should be closed. For this purpose, a first embodiment of a sealing cap 422 as shown in FIGS. 26A-B is provided. The sealing cap 422 is configured to utilize the gas sampling port on the face mask as a mask attachment fitting to attach to the lateral surface 424 of the mask as shown in FIGS. 26A-B. The gas sealing cap 422 is attached to the oxygen mask surface 424 (shown in FIG. 26B) by using a cap fitting 426, such as a male Luer lock fitting, to attach to the mask fitting, in this case the female Luer lock fitting 425. The cap 422 includes a housing interface 428 that creates a seal with the mask surface 424, preferably a solid device interface 428 that is sized and shaped to cover the mask gas vents 430. A handle or torque flange 431 is formed on the outside of the cap 422 to provide a point of contact for the user's fingers to twist the cap 422 onto and off the mask fitting.

Figure 26C:
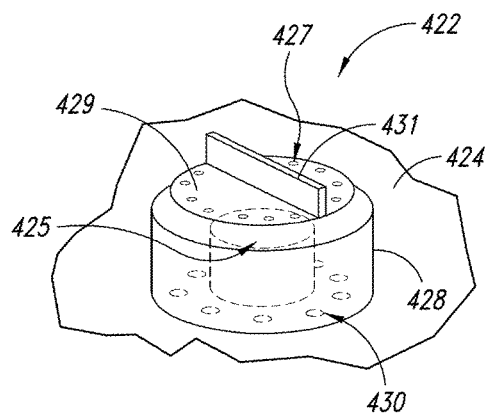
Figure 26D:
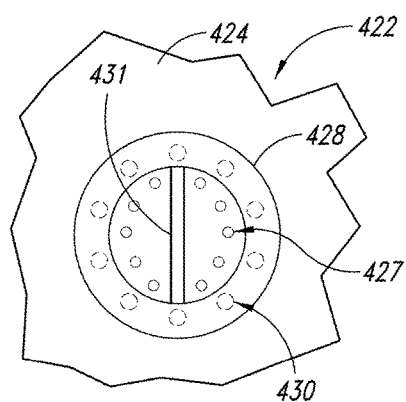
Figures 26E, 26F:
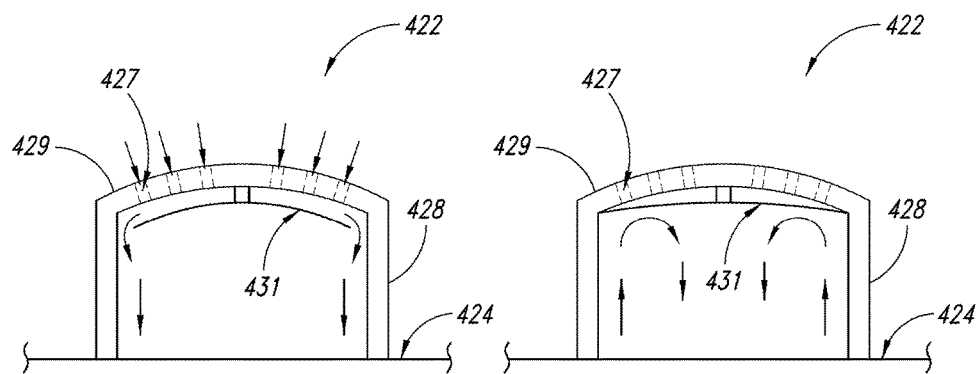

FIGS. 26C-D illustrate a variation of the cap 422 in which a plurality of openings 427 are formed in the housing top wall 429 that allow gas to be drawn into the face mask. However, a resilient valve member 431 mounted inside the housing adjacent the top wall 429 is biased to seal the openings 427 when the patient exhales, preventing gas from leaving the face mask. As will be readily appreciated from the foregoing, this cap allows for gas flow into the mask through a lateral gas vent but prevents gas from leaving through a gas vent. It would be used on one side of the mask while a uni-lateral gas scavenging system was in place on the opposite side. The unidirectional flow from the cap prevents the patient from exhaling anesthetic gas into the room during recovery from anesthesia. The cap allows the patient to inhale gas through the cap in the event that their tidal volume exceeds the volume of gas available in the mask gas pocket. The flexible interior membrane 431 would open with negative inspiratory force and close with positive pressure during exhalation.

Capnography Gas Analysis Unit

Figures 27, 28:
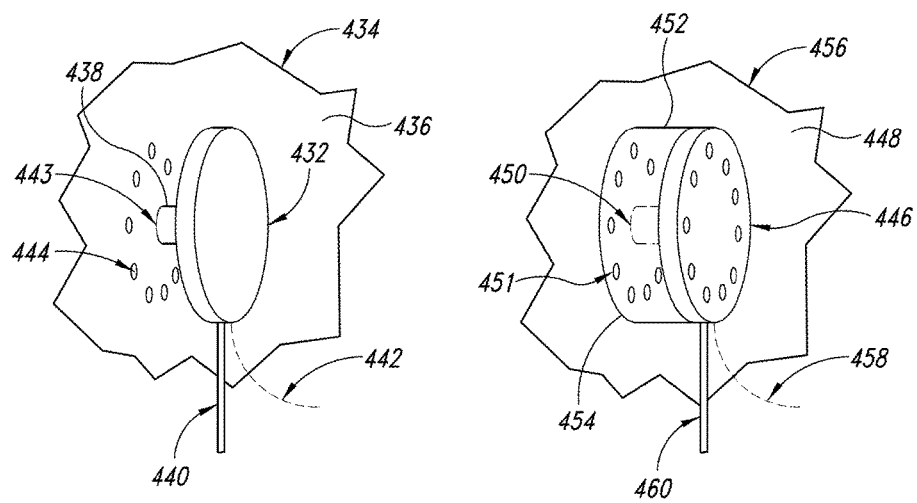
FIG. 27 is an isometric view of a capnography unit configured for attachment to the face mask of the present disclosure.
FIG. 28 is an isometric view of a pulmonary function module configured for attachment to the face mask of the present disclosure.

Referring next to FIG. 27, a mainstream capnography gas analysis unit 432 may also be used with the gas sampling oxygen mask 434. The capnography gas analysis unit 432 houses the gas analysis hardware and attaches to the lateral surface 436 of the mask 434 using a device fitting 438. The gas analysis unit 432 may be wired or wireless, and may be configured to analyze $CO_2$ plus additional gases. It may have a gas sample line 440 attached along with a monitor wire 442 that couple to an analyzing unit (not shown) where the analysis of the gases collected by the unit 432 is further process and displayed or printed out or both. In this embodiment the analysis unit 432 is capable of analyzing gas that passes through a central pore or opening 443 in the mask attachment fitting. In this embodiment, the existing gas vents 444 remain open to the ambient air.

Pulmonary Function Module

A pulmonary function module 446 may also be attached to the mask 456 using an attachment fitting 450 as depicted in FIG. 28. The module 446 attaches to the mask surface 448 using an interface coupling or fitting 450, such as previously described herein. The module 446 includes a housing 452 with a solid interface 454 with the surface 448 of the mask 456. The pulmonary function module 446 may contain a variety of analysis instruments. It may contain a flow meter to measure expiratory volume through the gas vent. It may contain gas analysis hardware such as a mainstream capnography unit or other gas analysis capability. The module 446 may be hardwired via a monitor wire 458 or configured for wireless communication. It may also be attached to a gas sample line 460.

Non-Rebreather Valve

Figure 29:
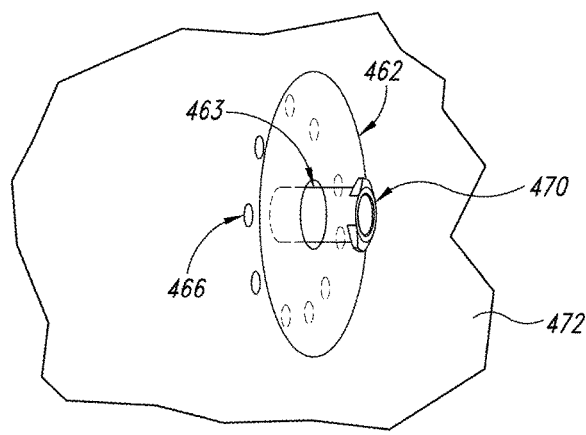
FIG. 29 is an isometric view of a non-rebreather valve configured for attachment to the face mask of the present disclosure.

A non-rebreather valve 462 shown in FIG. 29 may be created to use with this mask type. The valve 462 may be a flexible piece of plastic that attaches to the mask fitting 470 and covers the exhalation vents 466 of the mask 468. During exhalation the gas exiting the vents 466 pushes the valve 462 away from the mask surface 472, uncovering the vents 466. During inhalation the valve 462 closes or is pulled tight over the vents 466 by the vacuum created during inhalation, closing off the vents. This makes it appropriate for use with a non-rebreather oxygen mask. The valve 462 has a central opening 463 sized and shaped to slide over and surround the mask attachment fitting or gas sampling port 470 without interfering with its function.

Nebulizer

Figure 30:
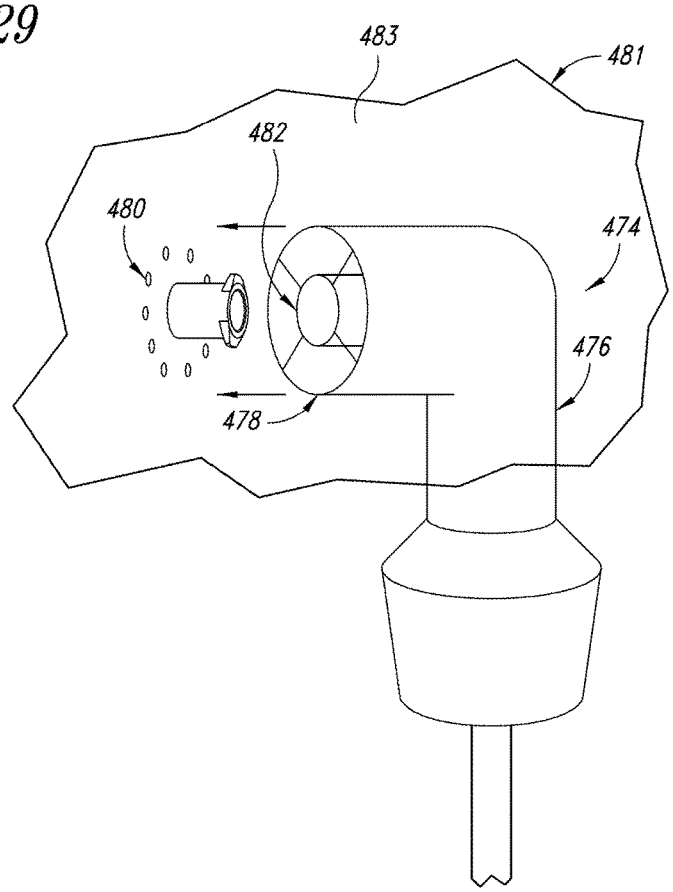
FIG. 30 is an isometric view of a nebulizer configured for attachment to the face mask of the present disclosure.

A nebulizer 474 is configured for use with the mask attachment fittings as shown in FIG. 30. The nebulizer 474 includes a housing 476 having solid device interface 478 to create a seal around gas vents 480 by engaging the surface 483 of the mask 481. The nebulizer 478 uses an attachment fitting 482 to connect to the lateral mask surface 483 via the mask attachment fitting 482. The nebulizer 474 is configured to deliver medication or other substance to the patient through the gas exhalation vents 480 of the mask 481.

Gas Scavenging System

Figure 31A:
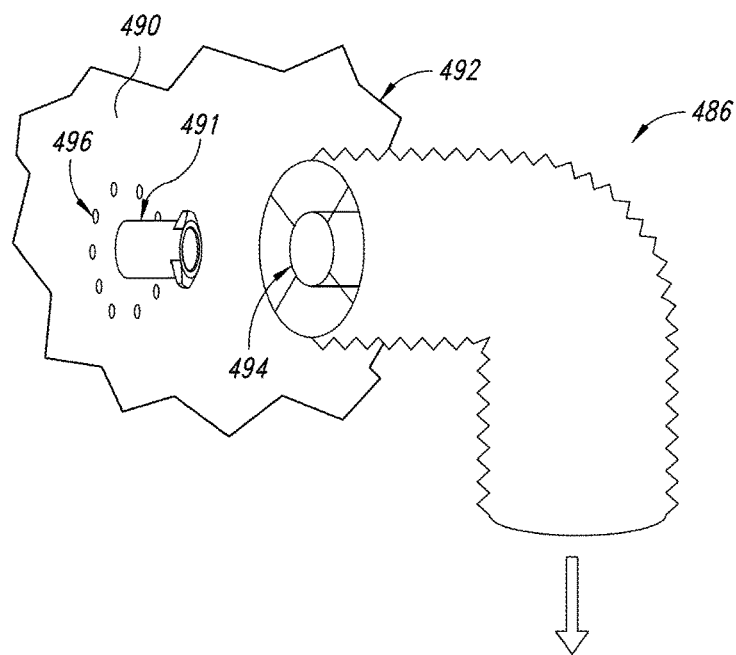
FIGS. 31A-B are isometric views of gas scavenging systems configured for attachment to the face mask of the present disclosure.
Figure 31B:
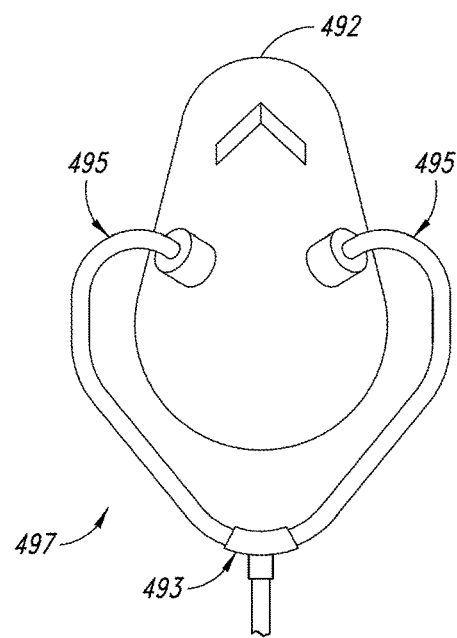

A gas scavenging system 486 may be created to remove exhaled gas out of the mask 492 using one or both port assemblies as shown in FIG. 31A. The scavenging system 486 is configured to attach to the lateral surface 490 of the mask 492 using a device fitting 494, such as described previously herein, to couple to the Luer lock or other fitting 491 on the face mask 492. The system 486 creates a seal with the surface 490 of the mask 492 and covers the gas exhalation vents 496. This system may be advantageous if a patient was at risk for spreading a pulmonary infection through exhaled gas or was continuing to eliminate inhaled anesthetics through breathing. The scavenging system 486 may have a port for monitoring scavenged gases including $CO_2$. FIG. 31B shows a bilateral gas scavenging system 497 in which there are two scavenging tubes 495 attached on each side of the mask 492 and joined together in fluid communication through a Y-shaped connector 493.

Gas Reservoir System

Figure 32A:
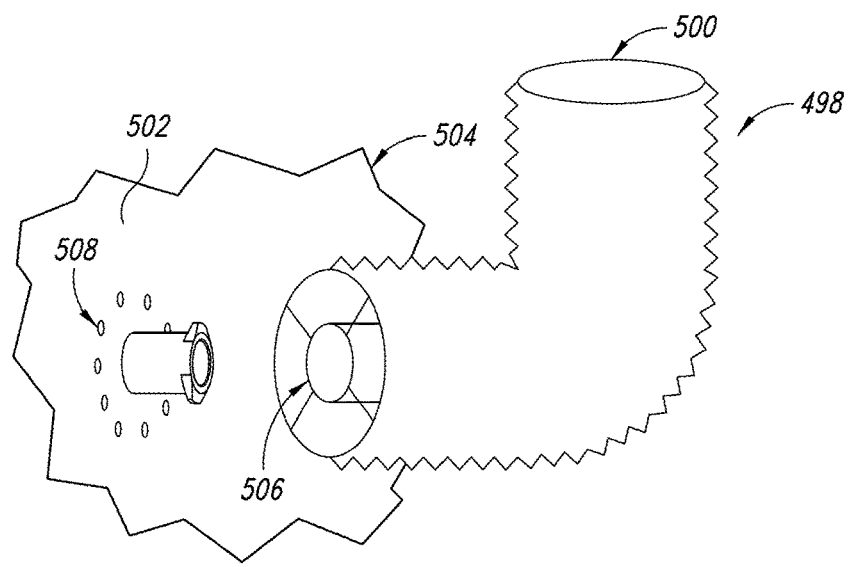
FIG. 32A-B are isometric views of gas reservoir systems configured for attachment to the face mask of the present disclosure.
Figure 32B:
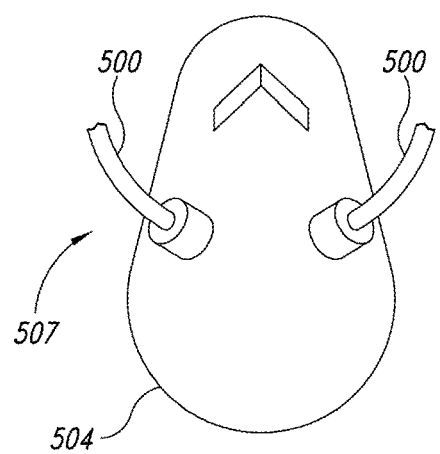

A gas reservoir system 498 could be created by attaching one or more gas reservoir tubes 500 to one or both sides of the mask as in FIG. 32A. The tubing 500 attaches to lateral surface 502 of the mask 504 using a device attachment fitting 506 to create a seal over the gas exhalation vents 508 as described above with the gas scavenging system 486. The reservoir tube 500 fills with oxygen or other inhaled gas during periods of apnea or when gas flow rates exceed minute ventilation. When a patient inhales in the presence of the tube 500 and the tidal volume exceeds the volume contained within the gas pocket of the mask, the gas within the tube 500 will be entrained and serve as inhaled gas. The tubes 500 may be flexible and allow positioning pointing up to maintain a reservoir of gas and or other agents that may flow down by gravity. The tubes could also be positioned down to collect gas that may flow up with gravity. The gas reservoirs may have a port for monitoring gases including exhaled $CO_2$. FIG. 32B shows a bilateral gas reservoir tube system 507 in which two tubes 500 are coupled to each side of the mask 504.

Gas Filter

Figure 33:
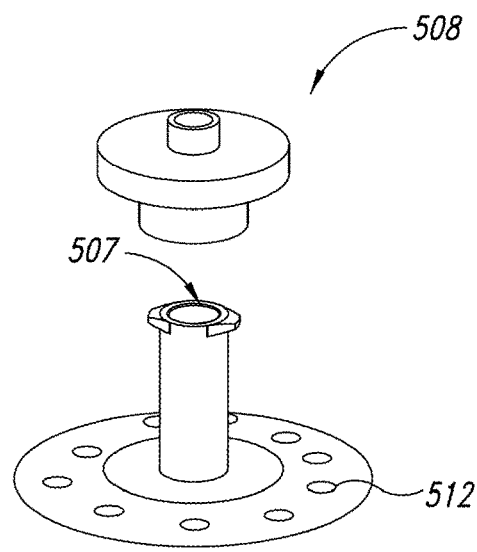
FIG. 33 is an isometric view of a gas filter configured for attachment to the face mask of the present disclosure.

Gas filters 508 may be used with the masks as shown in FIG. 33. The filter 508 is an off-the shelf commercially available filter and will not be described in detail herein. Briefly, the filter 508 is comprised of a plastic housing containing a filter and two attachment fittings for interface with the face mask surface and with a gas sample line. In this example the filter 508 would attach to the mask fitting with the central channel that allows gas to pass from inside the mask, through the filter, and into a gas analysis sample line that could be attached to the filter. All gas passing through the luer port would actually pass through the filter. The filters are available off the shelf. The filter would attach to the mask surface attachment fitting, e.g., a Luer fitting, and filter all the gas passing from that Luer fitting through the gas sample tubing and fitting into the monitoring unit. The filter material inside the plastic housing is a disc and does not have a central opening.

Figure 34:
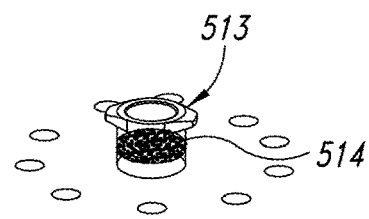
FIG. 34 is an isometric view of an integrated gas filter configured for attachment to the face mask of the present disclosure.
Figures 35A, 35B:
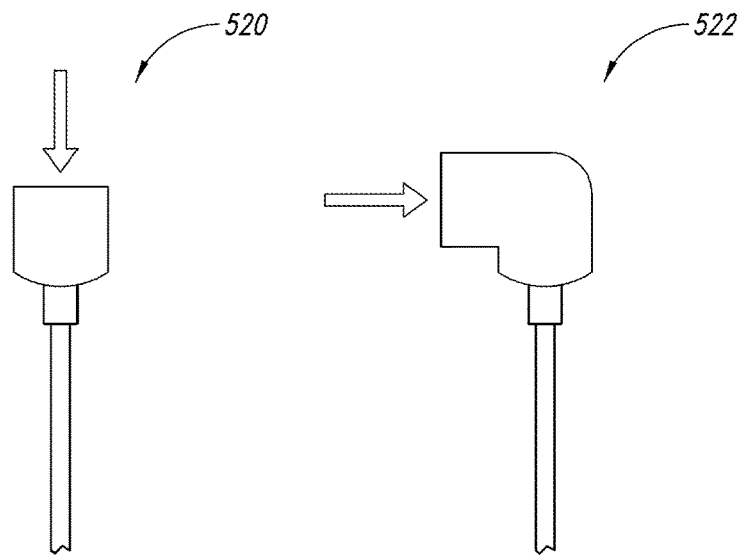
FIGS. 35A-B are side views of straight and 90 degree sample line fittings for attachment to the face mask of the present disclosure.
Figures 36A, 36B:
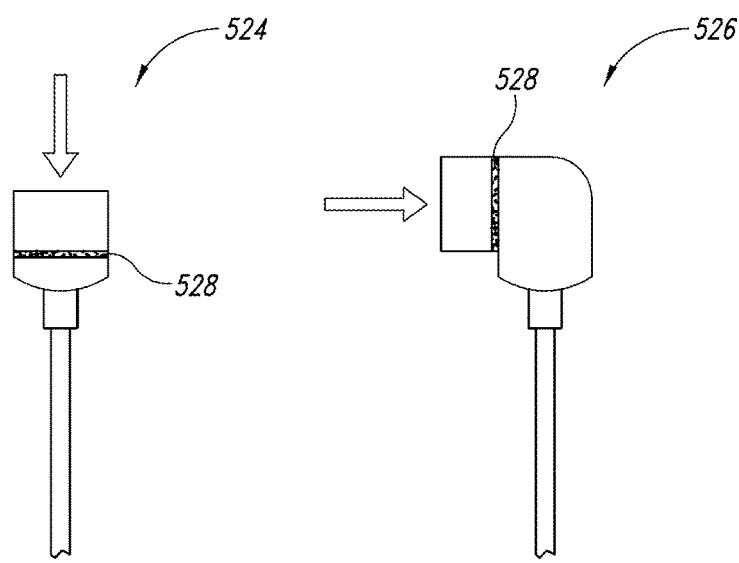
FIGS. 36A-B are side views of straight and 90 degree integrated filter fittings for attachment to the face mask of the present disclosure.

Alternatively, as shown in FIG. 34, the mask fittings 513 could be produced with integrated gas filters 514 present in the centers of the attachment fittings 513 or sample ports. In this example, a gas sample line could attach to the mask attachment fitting 513 and aspirate filtered patient gas without the need to attach a separate gas filter in the monitoring apparatus.

Sample Lines

FIGS. 35A-B and 36A-B show sample lines 520, 522, 524, and 526, respectively, that may be used with the masks described above by attaching to the lateral surface attachment fittings. The lines 520, 524 may have a straight connection with a 0 degree angle from the device attachment fitting and the sample line itself. The lines 522, 526 may also have an angle, such as 90 degrees as shown, or other angels, such as without limitation 20, 33, 45, 66 degrees, between the device attachment fitting and the sample line. The sample line may be added separately to the mask in use or be assembled and delivered with the mask as a single unit. The sample lines may also have integrated filters 528 to process patient gas as it is aspirated to the patient monitor.

The mask attachment fitting may or may not be used to sample gases and may have a mechanism to open only with use. In this example a valve present in the mask attachment fitting is closed until it engages with a device attachment fitting which pushes the valve open. The valve may or may not have gas filtering properties.

Mask Fitting with Membrane or Flaps

Figure 37A:
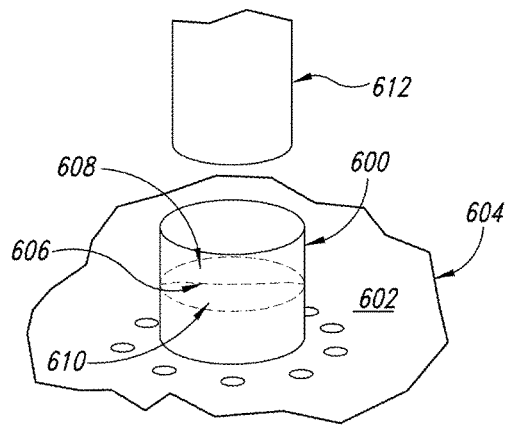
FIGS. 37A-B are isometric views of an openable and closable mask fitting for attachment to the face mask of the present disclosure.
Figure 37B:
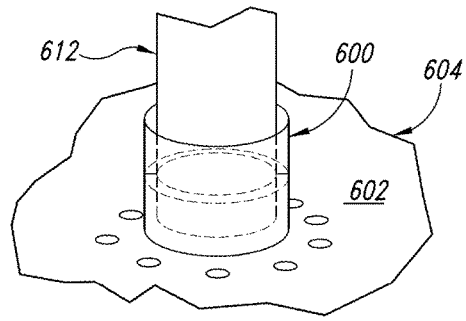

FIGS. 37A-B illustrate another aspect of the present disclosure in which a fitting 600 extending from the surface 602 of a mask having vent openings 604 is closed with a membrane that is opened only when in use. For example, the membrane can be pierced or, as shown, a split membrane 606. In essence the split membrane 606 is formed of two flaps 608, 610 that in a relaxed condition are coplanar and effectively close off the fitting 600, and in a pierced condition in which the membrane is separated so the flaps maintain a seal around a second device 612 inserted into the fitting 600. In use, the second device is inserted with sufficient force into the fitting 600 that it will forced the membrane 606 to open by separating the flaps 608, 610, as shown in FIG. 37B. It is to be understood that the membrane 606 may be configured to separate into more than two flaps or open through other undisclosed mechanisms. For example, multiple linear weakened areas, such as scored, perforated, or linear areas of thinner material may be formed that are configured to form the sealing membrane 606 across the inside diameter of the fitting 600 and to separate into multiple flaps of equal size that bear against and provide a seal between the exterior of the second device 612 and the interior of the fitting 600.

Aerosol Mask Platform Insert

Figure 38A:
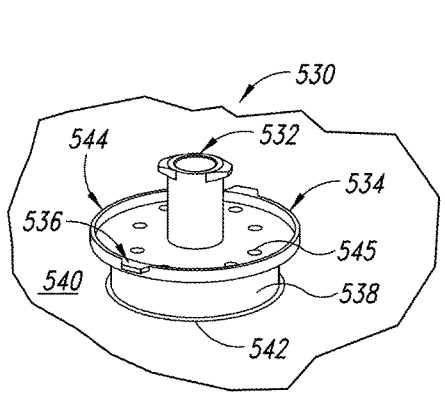
FIGS. 38A-B are an isometric and top view, respectively, of an aerosol mask platform insert for attachment to the face mask in accordance with the present disclosure.
Figure 38B:
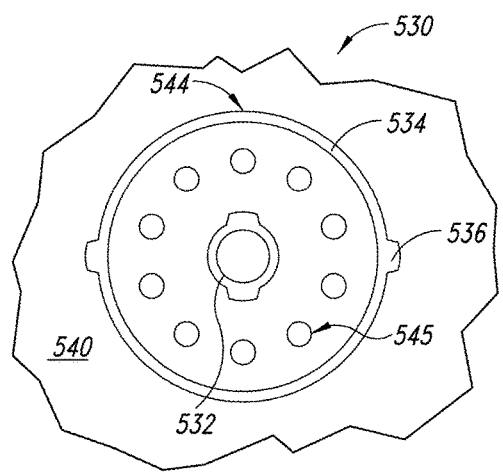

FIGS. 38A-B illustrate an aerosol mask platform insert 530, which includes a female Luer fitting 532 and also includes a second attachment fitting for the mask components described above. This new insert is related most closely to the described above in conjunction with FIGS. 24A-D. The component 260 illustrated in FIGS. 24A-D is a Luer insert designed to be used with an aerosol mask or any mask equipped with a sufficiently large port or opening. The insert 530 of FIGS. 37A-B differs from the component 260 in FIGS. 24A-D in three ways:

The presence of a raised edge 534. The presence of attachment phalanges 536 on the raised edge 534. And a cylindrical penetrating section 538 of the insert 530 that spans from the mask surface 540 to the interior of the mask. The penetrating section 538 "pops" into place by pressing through a securing edge 542 that is circular around the penetrating section 538.

This round aerosol mask insert 534 pushes through a circular opening in an oxygen mask. This size mask opening is found most commonly in off the shelf aerosol masks but can be created in any size through any manufacturing or post manufacturing process. The insert and mask opening could be circular or any non-circular shape that would prevent rotation when engaged. The narrowed central penetrating section 538 that spans from the outer to inner surface of the mask has an inner portion with the securing edge 542 that pops across the mask wall and holds the insert in place.

The base part 544 of the insert 530 on the outside of the mask is wider than the mask opening and wider than the penetrating section 538, thus preventing it from falling inside the mask. A bonding agent or solvent may be used in between the mask surface and the portion of the insert contacting the outer surface and prevent movement and or rotation.

Figure 39B:
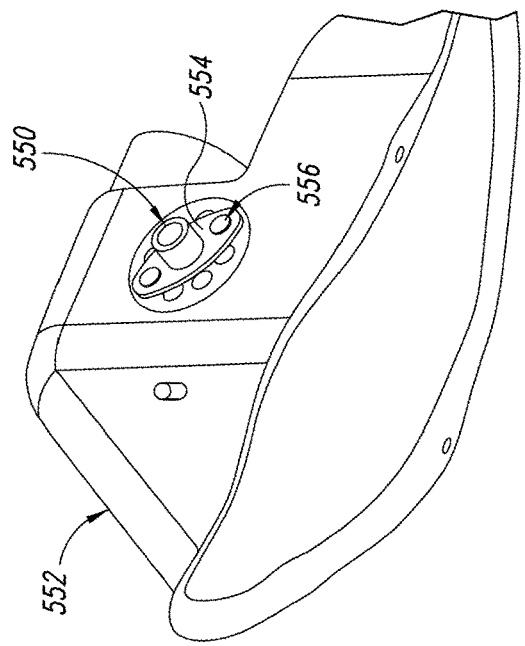
FIGS. 39A-D illustrate an alternative method of attaching the female Luer fitting to the face mask in accordance with the present disclosure.
Figure 39A:
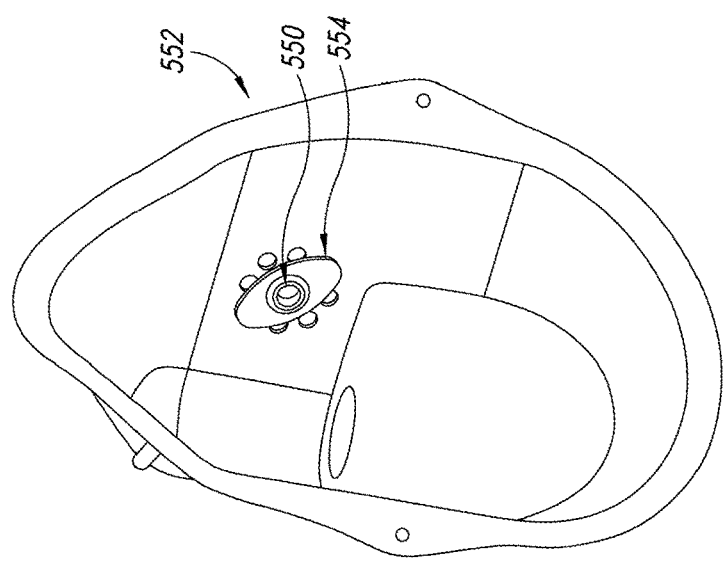
Figure 39D:
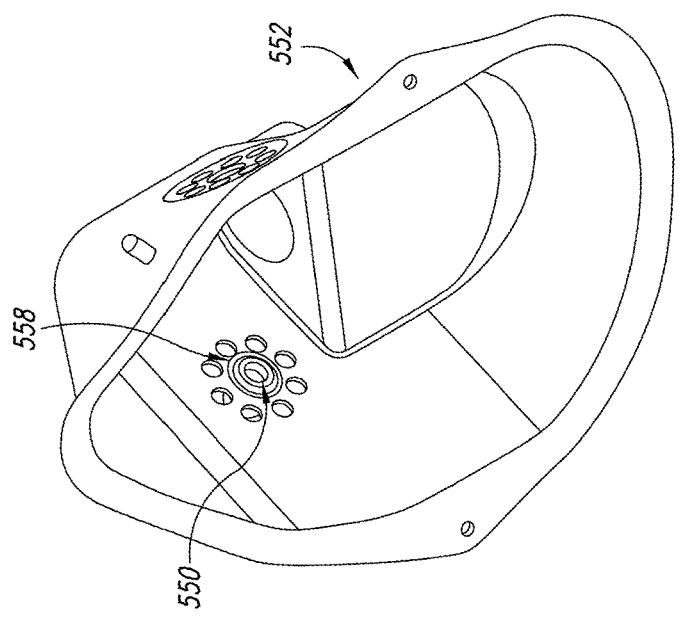
Figure 39C:
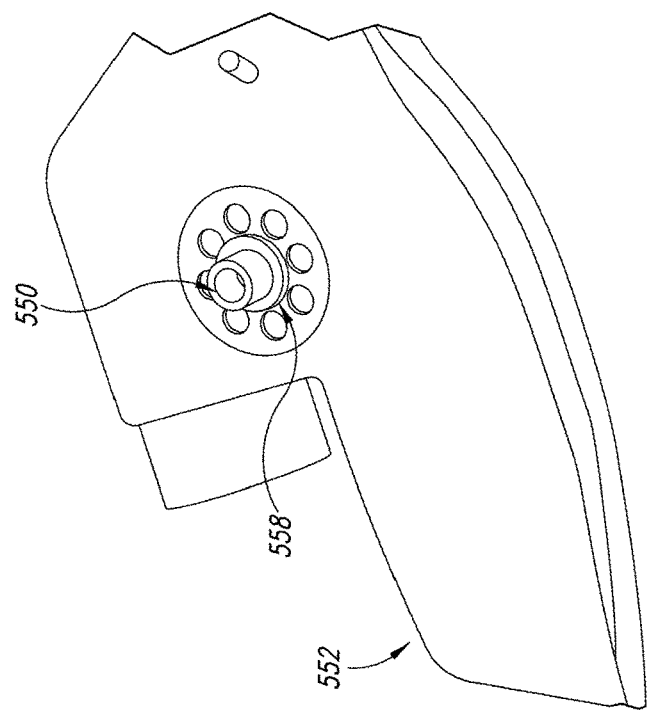

The central female luer 532 or other attachment fitting is in the center of the insert 530, which is surrounded by gas vents 545, which are surrounded by the raised edge 534. The raised edge 534 has one or more attachment flanges 536 that are used to interface with device components (CO2 colorimetric detector, gas reservoir tubes, gas scavenging system, nebulizer, etc.) and hold them in place securely and reversibly As for additional details pertinent to the present disclosure, materials and manufacturing techniques may be employed as within the level of those with skill in the relevant art. The same may hold true with respect to method-based aspects of the disclosure in terms of additional acts commonly or logically employed. Also, it is contemplated that any optional feature of the inventive variations described may be set forth and claimed independently, or in combination with any one or more of the features described herein. For example, FIGS. 39A-D illustrate an alternative method of attaching or affixing the female Luer fitting 550 to the face mask 552 in accordance with the present disclosure. In particular, FIGS. 39A-B show a pair of oval-shaped retaining members 554 applied to the inside and outside of the face mask 552 and in slidable engagement with the Luer fitting 550 and secured in place with known methods, such as adhesive, to hold the Luer fitting in place. Alternatively, fasteners 556 can be used alone or in conjunction with adhesive to hold the two retaining members 554 in engagement with each other. Similarly, FIGS. 39C-D show a pair of circular retaining members 558 holding the Luer fitting 550 in place on the mask 552.

Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this disclosure belongs. The breadth of the present disclosure is not to be limited by the subject specification, but rather only by the plain meaning of the claim terms employed.

What is claimed is:

1. A face mask assembly comprising:
 a face mask to cover a user's nose and at least partially cover a user's mouth and configured to deliver oxygen to a user, the face mask including:
  a wall;
  a non-circular first port formed in the wall;
  a non-circular engagement portion surrounding the port in the wall of the mask; and
  a single-piece first mask connector configured to connect to the port, the first mask connector having:
   a first end configured to connect to a mating connector and to be external to the mask;
   an external flange distal to the first end and configured to appose an outer surface of the wall of the mask;
   a non-circular neck region distal to the external flange and configured to appose the engagement portion to prevent rotation of the first mask connector relative to the face mask;
   a second end distal to the neck region; and
   a first longitudinal channel continuous from the first end to the second end;
  a non-circular second port configured to connect to a single-piece second mask connector, the second mask connector configured to connect to a second mating connector, wherein the second port and second mask connector are on an opposing side of a midline of the face mask from the first port and first mask connector; the second mask connector having:
   a first end configured to connect to the second mating connector and to be external to the face mask;
   an external flange distal to the first end and configured to appose an outer surface of the wall of the mask;
   a non-circular neck region distal to the external flange and configured to appose a second engagement portion to prevent rotation of the second mask connector relative to the face mask;
   a second end distal to the neck region; and
   a first longitudinal channel continuous from the first end to the second end; and
  the first and second ports are co-located with a plurality of exhalation vents.

2. The face mask assembly of claim 1 wherein the first mask connector includes an internal flange distal to the neck region of the first mask connector and configured to appose a portion of an inside of the mask wall and is configured to minimize outward longitudinal movement of the first mask connector relative to the rest of the mask.

3. The face mask assembly of claim 2 wherein the internal flange comprises a non-circular cross-sectional shape.

4. The face mask of claim 3 wherein the port, the neck region and the internal flange comprise substantially ellipsoid cross-sectional shapes.

5. The face mask of claim 3 wherein an outer footprint of the internal flange is smaller than an outer footprint of the port and wherein the neck region does not substantially rotate relative to the mask when the first mask connector is in place in the port.

6. The face mask assembly of claim 1 further comprising an adhesive material configured to hold the external flange of the first mask connector and an outer wall portion of the mask together.

7. A single-piece connector for use with a luer connector and with a face mask having a non-circular port and non-circular engagement portion, the connector comprising:
   a first end with a mating portion configured to mate with the luer connector;
   an external flange distal to the first end having a substantially flat distal surface and defining an external flange footprint;
   a neck region distal to the external flange having a non-circular cross-sectional shape and a neck region footprint wherein the external flange footprint is larger than the neck region footprint, the neck region configured to appose the non-circular engagement portion to prevent rotation of the connector relative to the face mask;
   an internal flange distal to the neck region and having a substantially flat proximal surface;
   a second end distal to the internal flange; and
   a longitudinal channel continuous from the first end to the second end.

8. The single piece connector of claim 7 wherein the neck region cross-sectional shape defines a first ellipsoidal shape and a cross-sectional shape of the internal flange defines a second ellipsoidal shape and the first ellipsoidal shape is in a rotated position relative to the second ellipsoidal shape.

9. The single piece connector of claim 8 wherein a neck region non-circular total cross-sectional area is within 10% of an external flange total cross-sectional area.

10. The single piece connector of claim 7, comprising a gas filter placed within the longitudinal channel.

11. A face mask to cover a user's nose and at least partially cover a user's mouth and configured to deliver oxygen to a user, the face mask comprising:
   a wall;
   a port in the wall;
   an engagement portion around the port; and
   a first mask connector configured to connect to the port, the first mask connector having:
      a first end configured to connect to a mating connector and to be external to the mask;
      an external flange distal to the first end and configured to appose an outer surface of the wall of the mask;
      a non-circular neck region distal to the external flange and configured to appose the engagement portion to prevent rotation of the first mask connector relative to the face mask;
      a second end distal to the neck region; and
      a first longitudinal channel continuous from the first end to the second end;
      an internal flange distal to the neck region and configured to appose a portion of an inside of the wall and to minimize outward longitudinal movement of the first mask connector relative to the rest of the mask, the internal flange having a non-circular cross-sectional shape and an outer footprint that is smaller than an outer footprint of the port.

12. The face mask of claim 11 wherein the port comprises a first port, the face mask further comprising a second port having a non-circular cross-sectional shape, wherein the first and second ports are on opposing sides of a midline of the face mask.

13. A face mask assembly comprising:
   a face mask to cover a user's nose and at least partially cover a user's mouth and configured to deliver oxygen to a user, the face mask including:
      a wall;
      a non-circular port formed in the wall;
      a non-circular engagement portion surrounding the port in the wall of the mask; and
      a single-piece first mask connector configured to connect to the port, the first mask connector having:
         a first end configured to connect to a mating connector and to be external to the mask;
         an external flange distal to the first end and configured to appose an outer surface of the wall of the mask;
         a non-circular neck region distal to the external flange and configured to appose the engagement portion to prevent rotation of the first mask connector relative to the face mask, the neck region configured to not substantially rotate relative to the mask when the first mask connector is in place in the port;
         a second end distal to the neck region;
         a first longitudinal channel continuous from the first end to the second end;
         an internal flange distal to the neck region and configured to appose a portion of an inside of the mask wall and configured to minimize outward longitudinal movement of the first mask connector relative to the rest of the mask, the internal flange having a non-circular cross-sectional shape, and an outer footprint of the internal flange is smaller than an outer footprint of the port.

* * * * *